US007101695B2

(12) United States Patent
Chou

(10) Patent No.: US 7,101,695 B2
(45) Date of Patent: Sep. 5, 2006

(54) METHOD OF PRODUCING TRANSGLUTAMINASE HAVING BROAD SUBSTRATE ACTIVITY

(76) Inventor: Szu-Yi Chou, 468 S. Taaffe St., Sunnyvale, CA (US) 94087

( * ) Notice: Subject to any disclaimer, the term of this patent is extended or adjusted under 35 U.S.C. 154(b) by 660 days.

(21) Appl. No.: 10/231,470

(22) Filed: Aug. 28, 2002

(65) Prior Publication Data

US 2003/0219857 A1    Nov. 27, 2003

Related U.S. Application Data

(60) Provisional application No. 60/363,445, filed on Mar. 8, 2002, provisional application No. 60/361,166, filed on Mar. 1, 2002.

(51) Int. Cl.
| C12N 9/10 | (2006.01) |
| C12N 1/00 | (2006.01) |
| C12N 15/00 | (2006.01) |
| C07H 21/04 | (2006.01) |

(52) U.S. Cl. ............... 435/193; 435/252.3; 435/320.1; 435/886; 536/23.2; 530/350

(58) Field of Classification Search ............... 435/193, 435/252.3, 320.1, 886; 536/23.2; 530/350
See application file for complete search history.

(56) References Cited

U.S. PATENT DOCUMENTS

| 5,156,956 A | 10/1992 | Motoki et al. ............. 435/68.1 |
| 5,252,469 A | 10/1993 | Andou et al. ............. 435/71.2 |
| 5,420,025 A | 5/1995 | Takagi et al. ............. 435/193 |
| 5,726,051 A | 3/1998 | Fraij et al. ............. 435/193 |
| 5,827,712 A | 10/1998 | Yokoyama et al. ............. 435/193 |
| 6,010,871 A | 1/2000 | Takahara et al. ............. 435/68.1 |
| 6,013,498 A | 1/2000 | Yokoyama et al. ............. 435/193 |
| 6,013,526 A | 1/2000 | Takahara et al. ............. 435/455 |
| 6,030,821 A | 2/2000 | Soeda et al. ............. 435/188 |
| 6,100,053 A | 8/2000 | Bech et al. ............. 435/68.1 |
| 6,121,013 A | 9/2000 | Yamaguchi ............. 435/68.1 |
| 6,190,879 B1 | 2/2001 | Bech et al. ............. 435/68.1 |
| 6,190,896 B1 | 2/2001 | Fraij ............. 435/193 |
| 6,833,258 B1 * | 12/2004 | Yokoyama et al. ............. 435/193 |

FOREIGN PATENT DOCUMENTS

| EP | 0481504 | 4/1992 |
| JP | 10300889 | 12/1989 |
| JP | 4108381 | 4/1992 |
| JP | 6030771 | 2/1994 |
| WO | WO 2000/40706 | 7/2000 |
| WO | WO 2000/70026 | 11/2000 |
| WO | WO 1999/51723 | 4/2001 |
| WO | WO 2001/23591 | 4/2001 |
| WO | WO 02/14518 | 2/2002 |

OTHER PUBLICATIONS

Sequence alignment between SEQ ID No.: 2 from U.S. Appl. No. 6,833,258 and Applicants' SEQ ID No.: 6.*
Sequence alignment between Accession No. AAB97831 and Applicants' SEQ ID No.: 6.*
Sequence alignment between Accession No. AAB97831 and Applicants' SEQ ID No.: 10.*
Sequence alignment between Accession No. AAB97830 and Applicants' SEQ ID No.: 8; & Sequence alignment between Accession No. AAB97830 and Applicants' SEQ ID No.: 12.*
Gordon Ada, D.Sc., Vaccines and Vaccination. N Engl J Med, vol. 345, No. 14, p. 1042-1053.
Brandt ER, Sriprakash KS, Hobb RI, et al. New multi-determinant strategy for a group A streptococcal vaccine designed for the Australian aboriginal population. Nat. Med. 2000-6-455-9.
Nardin EH, Oliveira GA, Calvo-Calle JM, et al. Synthetic malaria peptide vaccine elicits high levels of antibodies in vaccines of defined HLA genotypes. J Infect Dis 2000;182:1486-96.
Watanabe et. al. Efficacy of chemically cross-linked antigens for accelular pertussis vaccine. Vaccine 19, 1199-1203 (2001).
Nancy St. Clair et. al. Cross-linked protein crystals for vaccine delivery. Proc. Natl. Acad. Sci. USA, vol. 96, pp. 9469-9474, Aug. 1999.
Raghunath et al., "Cross-Linking of the Dermo-Epidermal Junction of Skin Regenerating from Keratinocyte Autografts", J. Clin. Invest., vol. 98, No. 5, pp. 1174-1184, 1996.No.:05 Recombinant SC transglutaminase N-terminal sequence.
Jurgennsen et al., "A New Biological Glue for Cartilage-Cartilage Interfaces: Tissue Transglutaminase", The Journal of Bone and Joint Surgery, Inc., vol. 79-A, No. 2, Feb. 1997.
de Jong et al: "Purification and Substrate Specificity of Transglutaminases from Blood and Streptoverticillium mobaraense" Journal of Agricultural Food Chemistry 2001, vol. 49, pp. 3389-3393.
Washizu et al., "Molecular cloning of the gene for microbial transglutaminase from streptoverticillium and its expression in Streptomyces lividans" Biosci Biotech, Biochem, vol. 58 No. 1, pp. 82-87 (1994).
Pasternack et al., "Bacterial Pro-Transglutaminase from Streptoverticillium Mobaraense Purification, Characterisation and Sequence of the Zymogen" Euo. J. Biochem 1998, vol. 257, pp. 570-576.

(Continued)

*Primary Examiner*—Tekchand Saidha
(74) *Attorney, Agent, or Firm*—Patterson & Sheridan, LLP; Ya-Fen Chen

(57) ABSTRACT

Embodiments of the invention generally provide methods and compositions for producing recombinant transglutaminases. The purified recombinant transglutaminases of the invention are reactive to a broad range of compounds and exhibit broad substrate activity. In one embodiment, *Streptoverticillium mobaraense* (ATCC 29032), and *Streptoverticillium cinnamoneum* (ATCC 11874) recombinant transglutaminase fusion proteins purified from *E. coli* are provided to a better yield, higher purity, and activity than hitherto possible by recombinant DNA technology.

51 Claims, 11 Drawing Sheets

OTHER PUBLICATIONS

Liu et al., "Effect of Transglutaminase-Catalyzed Polymerization of its Emulsifying Properties" Journal of Agricultural Food Chemistry 1999, vol. 47, pp. 1514-1519.

Duran et al., "Purification, Characterisation, and Gene Cloning of Transglutaminase from Streptoverticillium Cinnamoneum CBS 683.68" Biochimie 80 (4) 1998, pp. 313-319.

Kahlem et al., "Peptides Containing Glutamine Repeats as Substrates for Transglutaminase-Catalyzed Cross-Linking: Relevance to Diseases of the Nervous System" Proc. National Academy of Science USA, vol. 93, pp. 14580-14585, Dec. 1996. Cell Biolog.

O'Brien-Simpson et al., "Polymerization of Unprotected Synthetic Peptides: A View toward Synthetic Peptides Vaccines" Journal of American Chemistry Society, 1997, vol. 119, pp. 1183-1188.

Jackson et al., "Free Radical Induced Polymerization of synthetic peptides into polymeric immunogens" Vaccine, vol 15, No. 15, pp. 1697-1705, 1997.

Kanaji et al., "Primary structure of microbial transglutaminase from Streptoverticillium" J. Biol. Chem. 268, 11565-11572, 1994.

Folk, J. E., and Cole, P.W. Mechanism of action of guinea pig liver transglutaminase. I. Purification and properties of the enzyme: identification of a functional cysteine essential for activity. J Biol Chem. Dec. 10, 1966;241(23):5518-25.

Shi, Q. et al. Expression in *Escherichia coli* and Purification of Hexahistidine-Tagged Human Tissue Transglutaminase. Protein Expr Purif. Apr. 2002;24(3):366-73.

Natsuka, S. et al. Molecular cloning and expression of Caenorhabditis elegans ERp57-homologue with transglutaminase activity. J Biochem (Tokyo). Dec. 2001;130(6):731-5.

Shcmidt et al. Lysine and polyamines are substrates for transglutamination of Rho by the Bordetella dermonecrotic toxin. Infection and Immunity Dec. 2001;69(12):7663-70.

Sato, H. et al. "Further studies on the site-specific protein modification by microbial transglutaminase." Bioconjug Chem. Sep.-Oct. 2001;12(5):701-10.

Suzuki, S. et al. Purification and characterization of novel transglutaminase from *Bacillus subtilis* spores. Biosci Biotechnol Biochem. Nov. 2000;64(11):2344-51.

Rucker, E. et al. Rapid evaluation and optimization of recombinant protein production using GFP tagging. Protein Expr Purif. Feb. 2001;21(1):220-3.

Eli-Berchoer, L. et al. Effect of intramolecular cross-linking between glutamine-41 and lysine-50 on actin structure and function. J Muscle Res Cell Motil. 2000;21(5):405-14.

Clemente, MG et al. Immune reaction against the cytoskeleton in coeliac disease. Gut. Oct. 2000;47(4):520-6.

Taguchi, S. et al. Substrate specificity analysis of microbial transglutaminase using proteinaceous protease inhibitors as natural model substrates. J Biochem (Tokyo). Sep. 2000;128(3):415-25.

Suzuki, Y. et al. Localization of porcine trappin-2 (SKALP/elafin) in trachea and large intestine by in situ hybridization and immunohistochemistry. Histochem Cell Biol. Jul. 2000;114(1):15-20.

Yamaguchi, S. et al. A novel protein-deamidating enzyme from Chryseobacterium proteolyticum sp. nov., a newly isolated bacterium from soil. Appl Environ Microbiol. Aug. 2000;66(8):3337-43.

Yokoyama, KI et al. Overproduction of microbial transglutaminase in *Escherichia coli*, in vitro refolding, and characterization of the refolded form. Biosci Biotechnol Biochem. Jun. 2000;64(6):1263-70.

Bechtold, U. et al. Enzymic preparation of protein G-peroxidase conjugates catalysed by transglutaminase. J Biochem (Tokyo). Feb. 2000;127(2):239-45.

Schmidt, G. et al. Identification of the C-terminal part of Bordetella dermonecrotic toxin as a transglutaminase for rho GTPases. J Biol Chem. Nov. 5, 1999;274(45):31875-81.

Yokoyama, K. et al. Overproduction of DnaJ in *Escherichia coli* improves in vivo solubility of the recombinant fish-derived transglutaminase. Biosci Biotechnol Biochem. Jun. 1998;62(6):1205-10.

Makarova, K. et al. A superfamily of archaeal, bacterial, and eukaryotic proteins homologous to animal transglutaminases. Protein Sci. Aug. 1999;8(8):1714-9.

Kobayashi, K. et al. Molecular cloning of the transglutaminase gene from *Bacillus subtilis* and its expression in *Escherichia coli*. Biosci Biotechnol Biochem. Jun. 1998;62(6):1109-14.

Pasternack et al. A fluorescent substrate of transglutaminase for detection and characterization of glutamine acceptor compounds. Anal Biochem. Jun. 15, 1997;249(1):54-60.

High-resolution structural studies of the factor XIIIa crosslinking site and the first type 1 module of fibronectin. Nat Struct Biol. Nov. 1995;2(11):946-50.

Wong et al. Expression of the transglutaminase gene in *Escherichia coli*. Int J Biochem. 1991;23(9):947-53.

Kim et al. The structure of the transglutaminase 1 enzyme. Deletion cloning reveals domains that regulate its specific activity and substrate specificity. J Biol Chem. Nov. 11, 1994;269(45):27979-86.

Takehana et al., "Chemical synthesis of the gene for microbial transglutaminase from Streptoverticillium and its expression in *Escherichia coli*." Biosci Biotechnol Biochem. Jan. 1994;58(1):88-92.

J.H. Kim et al. Histone cross-linking by transglutaminase. Biochem Biophys Res Commun May 24, 2002;293 (5): 1453-1457.

J.B. Cooper et al. Insolubilization of hydroxyproline-rich cell wall glycoprotein in aerated carrot root slices. Biochem Biophys Res Commun Apr. 15, 1983;112 (1): 161-167.

Akhtar et al. Guanidinium chloride-and urea-induced unfolding of the diametric enzyme glucose oxidase. Biochemistry Mar. 19, 2002;41(11):3819-27.

X. Fu et al. Generation of intramolecular and intermolecular sulfenamides, sulfinamides,and sulfonamides by bypochlorous acid: a potential pathway for oxidative crosslinking of low-density lipoprotein by myeloperoxidase. Biochemistry Jan. 29, 2002;41(4):1293-301.

A.H. Palamakumbura et al. A fluorometric assay for detection of lysyl oxidase enzyme activity in biological samples. Anal Biochem Jan. 15, 2002;300(2):245-51.

O. Otte et al. Characterization and oxidativein vitro cross-linking of an extensin-like protein and a proline-rich protein purified from chickpea cell walls. Phytochemistry Jan. 2000;53(1):1-5.

\* cited by examiner

SEQUENCE LISTING

<160> NUMBER OF SEQ ID NOS: 16

<210> SEQ ID NO 1
<211> LENGTH: 27
<212> TYPE: DNA
<213> ORGANISM: Streptomyces mobaraensis ATCC 29032

<400> SEQUENCE: 1
gctagccccg actccgacga cagggtc                                          27

<210> SEQ ID NO 2
<211> LENGTH: 25
<212> TYPE: DNA
<213> ORGANISM: Streptomyces mobaraensis ATCC 29032

<400> SEQUENCE: 2
tcacggccag ccctgcttta ccttg                                            25

<210> SEQ ID NO 3
<211> LENGTH: 28
<212> TYPE: DNA
<213> ORGANISM: Streptomyces cinnamoneus ATCC 11874

<400> SEQUENCE: 3
gctagctccc gggcccctc cgatgacc                                          28

<210> SEQ ID NO 4
<211> LENGTH: 26
<212> TYPE: DNA
<213> ORGANISM: Streptomyces cinnamoneus ATCC 11874

<400> SEQUENCE: 4
tcacggccag ccttgctcca ccttgg                                           26

<210> SEQ ID NO 5
<211> LENGTH: 998
<212> TYPE: DNA
<213> ORGANISM: Streptomyces mobaraensis ATCC 29032

<400> SEQUENCE: 5
cccgactccg acgacagggt caccctccc gccgagccgc tcgacaggat gcccgacccg        60
taccgtccct cgtacggcag ggccgagacg gtcgtcaaca actacatacg caagtggcag      120
caggtctaca gccaccgcga cggcaggaag cagcagatga ccgaggagca gcgggagtgg      180
ctgtcctacg gctgcgtcgg tgtcacctgg gtcaattcgg gtcagtaccc gacgaacaga      240
ctggccttcg cgtccttcga cgaggacagg ttcaagaaca gctgaagaa cggcaggccc       300 cggtccggcg agacgcgggc ggagttcgag ggccgcgtcg cgaaggagag cttcgacgag      360
gagaagggct tccagcgggc gcgtgaggtg cgtccgtca tgaacagggc cctggagaac       420
gcccacgacg agagcgctta cctcgacaac ctcaagaagg aactggcgaa cggcaacgac      480
gccctgcgca acgaggacgc ccgttccccg ttctactcgg cgctgcggaa cacgccgtcc      540
ttcaaggagc ggaacggagg caatcacgac ccgtccagga tgaaggccgt catctactcg      600
aagcacttct ggagcggcca ggaccggtcg agttcggccg acaagaggaa gtacggcgac      660
ccggacgcct ccgccccgc cccgggcacc ggcctggtcg acatgtcgag ggacaggaac       720
attccgcgca gccccaccag ccccggtgag ggattcgtca atttcgacta cggctggttc      780
ggcgcccaga cggaagcgga cgccgacaag accgtctgga cccacggaat cactatcacg      840

```
cgcccaatgg cagcctgggt gccatgcatg tctacgagag caagttccgc aactggtccg      900
agggttactc ggacttcgac cgcggagcct atgtgatcac cttcatcccc aagagctgga      960
acaccgcccc cgacaaggta aagcagggct ggccgtga                              998
```

<210> SEQ ID NO 6
<211> LENGTH: 332
<212> TYPE: PRT
<213> ORGANISM: Streptomyces mobaraensis ATCC 29032

<400> SEQUENCE: 6

```
Pro Asp Ser Asp Asp Arg Val Thr Pro Pro Ala Glu Pro Leu Asp Arg
1               5                   10                  15

Met Pro Asp Pro Tyr Arg Pro Ser Tyr Gly Arg Ala Glu Thr Val Val
            20                  25                  30

Asn Asn Tyr Ile Arg Lys Trp Gln Gln Val Tyr Ser His Arg Asp Gly
        35                  40                  45

Arg Lys Gln Gln Met Thr Glu Glu Gln Arg Glu Trp Leu Ser Tyr Gly
    50                  55                  60

Cys Val Gly Val Thr Trp Val Asn Ser Gly Gln Tyr Pro Thr Asn Arg
65                  70                  75                  80

Leu Ala Phe Ala Ser Phe Asp Glu Asp Arg Phe Lys Asn Glu Leu Lys
                85                  90                  95

Asn Gly Arg Pro Arg Ser Gly Glu Thr Arg Ala Glu Phe Glu Gly Arg
            100                 105                 110

Val Ala Lys Glu Ser Phe Asp Glu Glu Lys Gly Phe Gln Arg Ala Arg
        115                 120                 125

Glu Val Ala Ser Val Met Asn Arg Ala Leu Glu Asn Ala His Asp Glu
    130                 135                 140

Ser Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
                165                 170                 175

Asn Thr Pro Ser Phe Lys Glu Arg Asn Gly Gly Asn His Asp Pro Ser
            180                 185                 190

Arg Met Lys Ala Val Ile Tyr Ser Lys His Phe Trp Ser Gly Gln Asp
        195                 200                 205

Arg Ser Ser Ser Ala Asp Lys Arg Lys Tyr Gly Asp Pro Asp Ala Phe
    210                 215                 220

Arg Pro Ala Pro Gly Thr Gly Leu Val Asp Met Ser Arg Asp Arg Asn
225                 230                 235                 240

Ile Pro Arg Ser Pro Thr Ser Pro Gly Glu Gly Phe Val Asn Phe Asp
                245                 250                 255

Tyr Gly Trp Phe Gly Ala Gln Thr Glu Ala Asp Ala Asp Lys Thr Val
            260                 265                 270

Trp Thr His Gly Asn His Tyr His Ala Pro Asn Gly Ser Leu Gly Ala
        275                 280                 285

Met His Val Tyr Glu Ser Lys Phe Arg Asn Trp Ser Glu Gly Tyr Ser
    290                 295                 300

Asp Phe Asp Arg Gly Ala Tyr Val Ile Thr Phe Ile Pro Lys Ser Trp
305                 310                 315                 320

Asn Thr Ala Pro Asp Lys Val Lys Gln Gly Trp Pro
                325                 330
```

<210> SEQ ID NO 7
<211> LENGTH: 1005
<212> TYPE: DNA
<213> ORGANISM: Streptomyces cinnamoneus ATCC 11874

<400> SEQUENCE: 7

```
tcccgggccc cctccgatga ccgggaaact cctcccgccg agccgctcga caggatgcct      60
gaggcgtacc gggcctacgg aggcagggcc actacggtcg tcaacaacta catacgcaag     120
tggcagcagg tctacagtca ccgcgacgga agaaacagc aaatgaccga gagcagcga      180
gaaaagctgt cctacggttg cgttggcgtc acctgggtca actcgggccc ctacccgacg     240
aacagattgg cgttcgcgtc cttcgacgag aacaagtaca gaacgacct gaagaacacc     300
agcccccgac ccgatgaaac gcgggcgag ttcgagggtc gcatcgccaa gggcagtttc     360
gacgagggga agggtttcaa gcgggcgcgt gatgtggcgt ccgtcatgaa caaggccctg     420
gaaaatgccc acgacgaggg gacttacatc aacaacctca gacgagct cacgaacaac      480
aatgacgctc tgctccgcga ggacagccgc tcgaacttct actcggcgct gaggaacaca     540
ccgtccttca aggaaaggga cggcggcaac tacgacccgt ccaagatgaa ggcggtgatc     600
tactcgaagc acttctggag cgggcaggac cagcggggct cctccgacaa gaggaagtac     660
ggcgacccgg aagccttccg ccccgaccag ggtaccggcc tggtcgacat gtcgaaggac     720
agaagcattc cgcgcagtcc ggccaagccc ggcgaaggtt gggtcaattt cgactacggt     780
tggttcgggg ctcaaacaga gcggatgcc gacaaaacca catggaccca cggcgaccac     840
taccacgcgc ccaatagcga cctgggcccc atgcacgtac acgagagcaa gttccggaag     900
tggtctgccg ggtacgcgga cttcgaccgc ggagcctacg tgatcacgtt catacccaag     960
agctggaaca ccgccccgc caaggtggag caaggctggc cgtga                    1005
```

<210> SEQ ID NO 8
<211> LENGTH: 335
<212> TYPE: PRT
<213> ORGANISM: Streptomyces cinnamoneus ATCC 11874

<400> SEQUENCE: 8

```
Ser Arg Ala Pro Ser Asp Asp Arg Glu Thr Pro Pro Ala Glu Pro Leu
1               5                   10                  15

Asp Arg Met Pro Glu Ala Tyr Arg Ala Tyr Gly Gly Arg Ala Thr Thr
            20                  25                  30

Val Val Asn Asn Tyr Ile Arg Lys Trp Gln Gln Val Tyr Ser His Arg
        35                  40                  45

Asp Gly Lys Lys Gln Gln Met Thr Glu Glu Gln Arg Glu Lys Leu Ser
    50                  55                  60

Tyr Gly Cys Val Gly Val Thr Trp Val Asn Ser Gly Pro Tyr Pro Thr
65                  70                  75                  80

Asn Arg Leu Ala Phe Ala Ser Phe Asp Glu Asn Lys Tyr Lys Asn Asp
                85                  90                  95

Leu Lys Asn Thr Ser Pro Arg Pro Asp Glu Thr Arg Ala Glu Phe Glu
            100                 105                 110

Gly Arg Ile Ala Lys Gly Ser Phe Asp Glu Gly Lys Gly Phe Lys Arg
        115                 120                 125

Ala Arg Asp Val Ala Ser Val Met Asn Lys Ala Arg Leu Glu Asn Ala
    130                 135                 140

His Asp Glu Gly Thr Tyr Ile Asn Asn Leu Lys Thr Glu Leu Thr Asn
145                 150                 155                 160
```

```
Asn Asn Asp Ala Leu Leu Arg Glu Asp Ser Arg Ser Asn Phe Tyr Ser
                165                 170                 175

Ala Leu Arg Asn Thr Pro Ser Phe Lys Glu Arg Asp Gly Gly Asn Tyr
            180                 185                 190

Asp Pro Ser Lys Met Lys Ala Val Ile Tyr Ser Lys His Phe Trp Ser
        195                 200                 205

Gly Gln Asp Gln Arg Gly Ser Ser Asp Lys Arg Lys Tyr Gly Asp Pro
    210                 215                 220

Glu Ala Phe Arg Pro Asp Gln Gly Thr Gly Leu Val Asp Met Ser Lys
225                 230                 235                 240

Asp Arg Ser Ile Pro Arg Ser Pro Ala Lys Pro Gly Glu Gly Trp Val
                245                 250                 255

Asn Phe Asp Tyr Gly Trp Phe Gly Ala Gln Thr Glu Ala Asp Ala Asp
            260                 265                 270

Lys Thr Thr Trp Thr His Gly Asp His Tyr His Ala Pro Asn Ser Asp
        275                 280                 285

Leu Gly Pro Met His Val His Glu Ser Lys Phe Arg Lys Trp Ser Ala
    290                 295                 300

Gly Tyr Ala Asp Phe Asp Arg Gly Ala Tyr Val Ile Thr Phe Ile Pro
305                 310                 315                 320

Lys Ser Trp Asn Thr Ala Pro Ala Lys Val Glu Gln Gly Trp Pro
                325                 330                 335

<210> SEQ ID NO 9
<211> LENGTH: 1067
<212> TYPE: DNA
<213> ORGANISM: Streptomyces mobaraensis ATCC 29032

<400> SEQUENCE: 9
atgggcagca gccatcatca tcatcatcac agcagcggcc tggtgccgcg cggcagccat    60
atggctagcc ccgactccga cgacagggtc accccctccg ccgagccgct cgacaggatg   120
cccgacccgt accgtccctc gtacggcagg gccgagacgg tcgtcaacaa ctacatacgc   180
aagtggcagc aggtctacag ccaccgcgac ggcaggaagc agcagatgac cgaggagcag   240
cgggagtggc tgtcctacgg ctgcgtcggt gtcacctggg tcaattcggg tcagtacccg   300
acgaacagac tggccttcgc gtccttcgac gaggacaggt tcaagaacga gctgaagaac   360
ggcaggcccc ggtccggcga cgcgggcg gagttcgagg ccgcgtcgc gaaggagagc     420
ttcgacgagg agaagggctt ccagcggcg cgtgaggtgg cgtccgtcat gaacagggcc    480
ctggagaacg cccacgacga gagcgcttac ctcgacaacc tcaagaagga actggcgaac   540
ggcaacgacg ccctgcgcaa cgaggacgcc cgttccccgt tctactcggc gctgcggaac   600
acgccgtcct tcaaggagcg gaacggaggc aatcacgacc cgtccaggat gaaggccgtc   660
atctactcga agcacttctg gagcggccag gaccggtcga gttcggccga caagaggaag   720
tacggcgacc cggacgcctt ccgcccccgcc ccgggcaccg gcctggtcga catgtcgagg   780
gacaggaaca ttccgcgcag ccccaccagc cccggtgagg gattcgtcaa tttcgactac   840
ggctggttcg gcgcccagac ggaagcggac gccgacaaga ccgtctggac ccacggaatc   900
actatcacgc gcccaatggc agcctgggtg ccatgcatgt ctacgagagc aagttccgca   960
actggtccga gggttactcg gacttcgacc gcggagccta tgtgatcacc ttcatcccca  1020
agagctggaa caccgccccc gacaaggtaa agcagggctg ccgtga                1067

<210> SEQ ID NO 10
```

<211> LENGTH: 355
<212> TYPE: PRT
<213> ORGANISM: Streptomyces mobaraensis ATCC 29032 (about 355 amino acids)

<400> SEQUENCE: 10

```
Met Gly Ser Ser His His His His His His Ser Ser Gly Leu Val Pro
1               5                   10                  15

Arg Gly Ser His Met Ala Ser Pro Asp Ser Asp Asp Arg Val Thr Pro
            20                  25                  30

Pro Ala Glu Pro Leu Asp Arg Met Pro Asp Pro Tyr Arg Pro Ser Tyr
        35                  40                  45

Gly Arg Ala Glu Thr Val Val Asn Asn Tyr Ile Arg Lys Trp Gln Gln
    50                  55                  60

Val Tyr Ser His Arg Asp Gly Arg Lys Gln Gln Met Thr Glu Glu Gln
65                  70                  75                  80

Arg Glu Trp Leu Ser Tyr Gly Cys Val Gly Val Thr Trp Val Asn Ser
                85                  90                  95

Gly Gln Tyr Pro Thr Asn Arg Leu Ala Phe Ala Ser Phe Asp Glu Asp
            100                 105                 110

Arg Phe Lys Asn Glu Leu Lys Asn Gly Arg Pro Arg Ser Gly Glu Thr
        115                 120                 125

Arg Ala Glu Phe Glu Gly Arg Val Ala Lys Glu Ser Phe Asp Glu Glu
    130                 135                 140

Lys Gly Phe Gln Arg Ala Arg Glu Val Ala Ser Val Met Asn Arg Ala
145                 150                 155                 160

Leu Glu Asn Ala His Asp Glu Ser Ala Tyr Leu Asp Asn Leu Lys Lys
                165                 170                 175

Glu Leu Ala Asn Gly Asn Asp Ala Leu Arg Asn Glu Asp Ala Arg Ser
            180                 185                 190

Pro Phe Tyr Ser Ala Leu Arg Asn Thr Pro Ser Phe Lys Glu Arg Asn
        195                 200                 205

Gly Gly Asn His Asp Pro Ser Arg Met Lys Ala Val Ile Tyr Ser Lys
    210                 215                 220

His Phe Trp Ser Gly Gln Asp Arg Ser Ser Ala Asp Lys Arg Lys
225                 230                 235                 240

Tyr Gly Asp Pro Asp Ala Phe Arg Pro Ala Pro Gly Thr Gly Leu Val
                245                 250                 255

Asp Met Ser Arg Asp Arg Asn Ile Pro Arg Ser Pro Thr Ser Pro Gly
            260                 265                 270

Glu Gly Phe Val Asn Phe Asp Tyr Gly Trp Phe Gly Ala Gln Thr Glu
        275                 280                 285

Ala Asp Ala Asp Lys Thr Val Trp Thr His Gly Asn His Tyr His Ala
    290                 295                 300

Pro Asn Gly Ser Leu Gly Ala Met His Val Tyr Glu Ser Lys Phe Arg
305                 310                 315                 320

Asn Trp Ser Glu Gly Tyr Ser Asp Phe Asp Arg Gly Ala Tyr Val Ile
                325                 330                 335

Thr Phe Ile Pro Lys Ser Trp Asn Thr Ala Pro Asp Lys Val Lys Gln
            340                 345                 350

Gly Trp Pro
        355
```

<210> SEQ ID NO 11
<211> LENGTH: 1074

<212> TYPE: DNA
<213> ORGANISM: Streptomyces cinnamoneus ATCC 11874

<400> SEQUENCE: 11

```
atgggcagca gccatcatca tcatcatcac agcagcggcc tggtgccgcg cggcagccat      60
atggctagct cccgggcccc ctccgatgac cgggaaactc ctcccgccga ccgctcgac      120
aggatgcctg aggcgtaccg ggcctacgga ggcagggcca ctacggtcgt caacaactac     180
atacgcaagt ggcagcaggt ctacagtcac cgcgacggaa agaaacagca atgaccgaa      240
gagcagcgag aaaagctgtc ctacggttgc gttggcgtca cctgggtcaa ctcgggcccc     300
tacccgacga acagattggc gttcgcgtcc ttcgacgaga caagtacaa gaacgacctg      360
aagaacacca gccccccgacc cgatgaaacg cgggcggagt tcgagggtcg catcgccaag    420
ggcagtttcg acgagggaa gggtttcaag cgggcgcgtg atgtggcgtc cgtcatgaac      480
aaggccctgg aaaatgccca cgacgagggg acttacatca acaacctcaa gacggagctc    540
acgaacaaca atgacgctct gctccgcgag acagccgct cgaacttcta ctcggcgctg      600
aggaacacac cgtccttcaa ggaaagggac ggcggcaact acgacccgtc caagatgaag    660
gcggtgatct actcgaagca cttctggagc gggcaggacc agcggggctc ctccgacaag     720
aggaagtacg cgaccccgga agccttccgc cccgaccagg gtaccggcct ggtcgacatg    780
tcgaaggaca gaagcattcc gcgcagtccg gccaagcccg cgaaggttg ggtcaatttc      840
gactacggtt ggttcggggc tcaaacagaa gcggatgccg acaaaaccac atggaccccac  900
ggcgaccact accacgcgcc caatagcgac ctgggcccca tgcacgtaca cgagagcaag    960
ttccggaagt ggtctgccgg gtacgcggac ttcgaccgcg gagcctacgt gatcacgttc    1020
atacccaaga gctggaacac cgccccgcc aaggtggagc aaggctggcc gtga           1074
```

<210> SEQ ID NO 12
<211> LENGTH: 358
<212> TYPE: PRT
<213> ORGANISM: Streptomyces cinnamoneus ATCC 11874

<400> SEQUENCE: 12

```
Met Gly Ser Ser His His His His His His Ser Ser Gly Leu Val Pro
1               5                   10                  15

Arg Gly Ser His Met Ala Ser Ser Arg Ala Pro Ser Asp Asp Arg Glu
            20                  25                  30

Thr Pro Pro Ala Glu Pro Leu Asp Arg Met Pro Glu Ala Tyr Arg Ala
        35                  40                  45

Tyr Gly Gly Arg Ala Thr Thr Val Val Asn Asn Tyr Ile Arg Lys Trp
    50                  55                  60

Gln Gln Val Tyr Ser His Arg Asp Gly Lys Lys Gln Gln Met Thr Glu
65                  70                  75                  80

Glu Gln Arg Glu Lys Leu Ser Tyr Gly Cys Val Gly Val Thr Trp Val
                85                  90                  95

Asn Ser Gly Pro Tyr Pro Thr Asn Arg Leu Ala Phe Ala Ser Phe Asp
            100                 105                 110

Glu Asn Lys Tyr Lys Asn Asp Leu Lys Asn Thr Ser Pro Arg Pro Asp
        115                 120                 125

Glu Thr Arg Ala Glu Phe Glu Gly Arg Ile Ala Lys Gly Ser Phe Asp
    130                 135                 140

Glu Gly Lys Gly Phe Lys Arg Ala Arg Asp Val Ala Ser Val Met Asn
145                 150                 155                 160
```

Lys Ala Arg Leu Glu Asn Ala His Asp Glu Gly Thr Tyr Ile Asn Asn
            165                 170                 175

Leu Lys Thr Glu Leu Thr Asn Asn Asp Ala Leu Leu Arg Glu Asp
        180                 185                 190

Ser Arg Ser Asn Phe Tyr Ser Ala Leu Arg Asn Thr Pro Ser Phe Lys
            195                 200                 205

Glu Arg Asp Gly Gly Asn Tyr Asp Pro Ser Lys Met Lys Ala Val Ile
        210                 215                 220

Tyr Ser Lys His Phe Trp Ser Gly Gln Asp Gln Arg Gly Ser Ser Asp
225                 230                 235                 240

Lys Arg Lys Tyr Gly Asp Pro Glu Ala Phe Arg Pro Asp Gln Gly Thr
                245                 250                 255

Gly Leu Val Asp Met Ser Lys Asp Arg Ser Ile Pro Arg Ser Pro Ala
            260                 265                 270

Lys Pro Gly Glu Gly Trp Val Asn Phe Asp Tyr Gly Trp Phe Gly Ala
        275                 280                 285

Gln Thr Glu Ala Asp Ala Asp Lys Thr Thr Trp Thr His Gly Asp His
    290                 295                 300

Tyr His Ala Pro Asn Ser Asp Leu Gly Pro Met His Val His Glu Ser
305                 310                 315                 320

Lys Phe Arg Lys Trp Ser Ala Gly Tyr Ala Asp Phe Asp Arg Gly Ala
                325                 330                 335

Tyr Val Ile Thr Phe Ile Pro Lys Ser Trp Asn Thr Ala Pro Ala Lys
            340                 345                 350

Val Glu Gln Gly Trp Pro
        355

<210> SEQ ID NO 13
<211> LENGTH: 26
<212> TYPE: DNA
<213> ORGANISM: Humicola grisea var. thermoides ATCC 16453
<220> FEATURE:
<221> NAME/KEY: primer_bind
<222> LOCATION: (2)..(25)

<400> SEQUENCE: 13
gctagatgcg ttcctccccc ctcctc                                            26

<210> SEQ ID NO 14
<211> LENGTH: 24
<212> TYPE: DNA
<213> ORGANISM: Humicola grisea var. thermoidea ATCC 16453

<400> SEQUENCE: 14
ttacaggcac tgatggtacc agtc                                              24

<210> SEQ ID NO 15
<211> LENGTH: 42
<212> TYPE: PRT
<213> ORGANISM: Homo sapiens

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

```
<210> SEQ ID NO 16
<211> LENGTH: 20
<212> TYPE: PRT
<213> ORGANISM: Artificial Sequence
<220> FEATURE:
<223> OTHER INFORMATION: synthetic Bovine Serum Albumin peptide

<400> SEQUENCE: 16

Lys Lys Lys Cys Cys Thr Glu Ser Leu Val Asn Arg Arg Pro Cys Phe
1               5                   10                  15

Ser Gln Gln Gln
            20
```

METHOD OF PRODUCING TRANSGLUTAMINASE HAVING BROAD SUBSTRATE ACTIVITY

CROSS-REFERENCE TO RELATED APPLICATIONS

This application claims benefit of U.S. provisional patent application Ser. No. 60/361,166, entitled, "METHOD OF PRODUCING NONTOXIC CROSS-LINKED ANTIGENS", filed Mar. 1, 2002, and U.S. provisional patent application Ser. No. 60/363,445, entitled, "METHOD AND USES OF PRODUCING POLYVALENT PEPTIDE ANTIGENS BY TRANSGLUTAMINASES", filed Mar. 8, 2002. Each of the aforementioned related patent applications is herein incorporated by reference.

BACKGROUND OF THE INVENTION

Transglutaminases (EC 2.3.2.13: TG) are protein cross-linking enzymes capable of catalyzing an acyl transfer reaction in which a gamma-carboxy-amide group of a peptide-bound glutamine residue is the acyl donor. Primary amino groups in a variety of compounds such as peptides, proteins, and similar compounds may function as acyl acceptors with the subsequent formation of monosubstituted γ-amides of peptide bound glutamic acid. When the ε-amino group of a lysine residue in a peptide or polypeptide chain serves as the acyl acceptor, the transglutaminases form intramolecular or intermolecular γ-glutamyl-ε-lysyl crosslinks.

The crosslinking activity of transglutaminases has been shown to be useful for a variety of industrial purposes, including in the field of food processing, such as processing of raw fish meat paste, tofu noodles, confectionery/bread, food adhesives, sheet-like meat food, yogurt, jelly, cheesegelling of proteins, improving baking quality of flour, improving taste and texture of food proteins, as well as casein finishing in leather processing, etc. Transglutaminases have also been employed in the production of thermally stable materials such as microcapsules, carriers of immobilized enzymes and the like.

A wide array of transglutaminases have been identified and characterized from a number of animal species and a few plant species. The most widely used animal derived transglutaminase, factor XIIIa, is a $Ca^{2+}$-dependent multi-subunit enzyme. Factor XIIIa is a product-inhibited enzyme, which means the activity of the enzyme is inhibited by the product synthesized after the enzymatic reaction. Such a property is a disadvantage for many industrial applications and for obtaining product of the enzymatic reaction. A $Ca^{2+}$-dependent transglutaminase from the slime mold *Physarum polycephalum* has also been described in Klein et al., (1992). However, only few microbial transglutaminases have been disclosed, e.g., from the species *Streptoverticillium lividans*, *Streptoverticillium mobaraense*, *Streptoverticillium cinnamoneum*, and *Streptoverticillium griseocarneum* (in U.S. Pat. No. 5,156,956) and from the species contemplated to be *Streptomyces lavendulae* (in U.S. Pat. No. 5,252,469, and U.S. Pat. No. 5,156,956). Bacterial transglutaminases which do not require the presence of calcium for their activity are usually identified and tested by using a conventional enzyme assay in which hydroxylamine is converted to hydroxamic acid (Folk, J. E. & Cole, P. W. (1966)).

Biological agents such as transglutaminases have limitations in that they cross-link only a limited number of very specific compounds, i.e. they are very as substrate-specific. Moreover, despite some industrial applications, biological agents have not been used as cross-linking agents for preparing antigens or in other immunological applications. Most known cross-linking biological agents such as enzymes have not been considered desirable for immunological applications due to problems such as the lack of an adequate quantity of the enzymes, high cost, difficulty in purification, and the like. For example, the cross-linking biological agent, microbial transglutaminase, has been purified mainly from culture medium (JP-B-6-65280, Agric. Biol. Chem., vol. 69, no. 10, pp. 1301–1308). Microbial transglutaminases purified from crude lysate, culture medium, or batch fermentation may not be suitable for vaccine development due to contamination by toxic compounds or other cellular proteins or components which may induce undesirable cross-reactive antibodies.

One approach to prepare transglutaminase has been to use recombinant DNA techniques to produce bacterial strains that produce recombinant transglutaminases. For example, the *Streptoverticillium mobaraense* transglutaminase gene has been cloned for expression in *Escherichia coli*, *Streptomyces lividans*, and *Saccharomyces cerevisiae* (Washizu et al., Tahekana et al., and EP-A-0 481 504). However, even the most successful of these approaches (Washizu et al.) resulted in a production yield much lower than the yield in the wildtype *Streptomyces mobaraense* strain. Thus, none of the efforts to overproduce the *S. mobaraense* enzyme have been successful, despite utilization of a number of different approaches such as chemical synthesis of a codon-optimized gene and its subsequent expression (as a cleavable heterologous signal peptide fusion to the mature transglutaminase) to the periplasm of *E. coli* or *S. cerevisiae*, expression as a fusion protein to pro-transglutaminase in *S. cerevisiae*, and traditional isolation and expression of the natural transglutaminase from wildtype *S. mobaraense*.

Furthermore, protein cross-linking reactions by transglutaminase have the following problems. Since transglutaminase is an enzyme forming an intramolecular or intermolecular bridge as a result of the acyl rearrangement reaction, some proteins or peptides cannot serve as substrates for the enzyme due to an insufficient number of glutamine residues or lysine residues. For example, albumin proteins cannot be used as the substrate for transglutaminase in its native form despite the presence of intrinsic glutamine and lysine residues.

It would, therefore, be desirable to engineer a recombinant transglutaminase with a broad substrate specificity that can be efficiently and effectively be purified with a large yield. Such a transglutaminase could be used in antigen preparation, vaccine development, immunotherapy, and medical diagnostic applications. It further would be desirable to develop a reproducible transglutaminase purification procedure so as to meet the FDA purity standard required for the use of transglutaminase in a vaccine and/or diagnostic detection kit.

SUMMARY OF THE INVENTION

Embodiments of the invention generally provide methods and compositions for producing a recombinant transglutaminase. In one aspect, the method includes overexpressing the recombinant transglutaminase in a host cell containing a transglutaminase gene cloned from an organism into an expression vector. The recombinant transglutaminases are then purified and stored in an inactive form. The inactive recombinant transglutaminase is subsequently reversibly activated into an active form.

In another aspect, the invention provides a method for producing a recombinant transglutaminase having broad substrate activity. The method includes purifying the recombinant transglutaminase under denaturing conditions using a denaturant, refolding the recombinant transglutaminase into a folded structure through renaturation using a refolding solution, storing the recombinant transglutaminase in an inactive form, and activating the inactive recombinant transglutaminase into an active form. In one embodiment, the recombinant transglutaminase is purified from insoluble inclusion bodies, not from secreted protein fractions. In another embodiment, the recombinant transglutaminase is cloned from an organism into an expression system, expressed and purified by affinity chromatography.

Active and inactive forms of recombinant transglutaminases produced in accordance with the methods of the invention are also provided.

BRIEF DESCRIPTION OF THE DRAWINGS

So that the features of the invention can be understood in detail, a more particular description of the invention briefly summarized above may be had by reference to embodiments illustrated in the appended drawings. It is to be noted, however, that the appended drawings illustrate only certain embodiments of this invention should not be considered limiting of its scope, for the invention may admit to other equally effective embodiments.

DETAILED DESCRIPTION OF THE INVENTION

Unless defined otherwise, all technical and scientific terms used herein have the same meaning as commonly understood by one of ordinary skill in the art to which this invention belongs. All publications mentioned herein are incorporated by reference to disclose and describe the methods and/or materials in connection with the publications cited. In this specification and the appended claims, the singular forms "a," "an," and "the" include plural reference unless the context clearly dictates otherwise.

I. Definitions

The term "adjuvant" as used herein is defined as a substance capable of non-specifically enhancing or potentiating an immune response.

The term "antibody" as used herein is defined as an immunoglobulin protein made in response to a specific antigen. The term "antibody" encompasses all types of antibodies; e.g., monoclonal antibodies, polyclonal antisera, anti-serum having antibodies, etc.

The term "antigen" as used herein is defined as a molecule capable of stimulating an immune response in an organism. An antigen of the invention includes but is not limited to an epitope, antigen, and/or antigenic fragment and could be a protein, a polypeptide, a peptide, etc. The term "antigenic fragment" as used herein is defined as a portion of a molecule capable of stimulating an immune response.

The term "antigenic determinant", as used herein, refers to a given region or three-dimensional structure of a molecule that binds specifically to an antibody.

The term "cross-linking" as used herein is defined as formation of a chemical bond within a molecule or between two molecules The term "derivative", as used herein, refers to a modified form of a compound.

The term "enzyme-linked immunosorbent assay" (ELISA) is a test that detects antibodies based on a calorimetric reaction.

The term "mimetic", as used herein, refers to a molecule, the structure of which is developed from knowledge of the structure of a compound or portions thereof and that mimics the chemical nature of the compound.

The term "peptide" as used herein is defined as a short chain of polymerized amino acids or amino acid mimetics.

The term "protein" as used herein is defined as a polypeptide chain.

The term "purified antibody" as used herein is defined as antibody sufficiently free of the other proteins, carbohydrates, and lipids with which it is naturally associated.

The term "transglutaminase" as used herein is defined as an enzyme capable of catalyzing an acyl transfer reaction in which a γ-carboxyamide group of a peptide-bound glutamine residue is the acyl donor. The term "$Ca^{2+}$-independent transglutaminase" as used herein is defined as a transglutaminase active in the presence or absence of free $Ca^{2+}$-ions; i.e., in the presence of excess ion chelators, such as EDTA.

II. Cross-linking a Compound Using a Biological Agent

Figure 1:
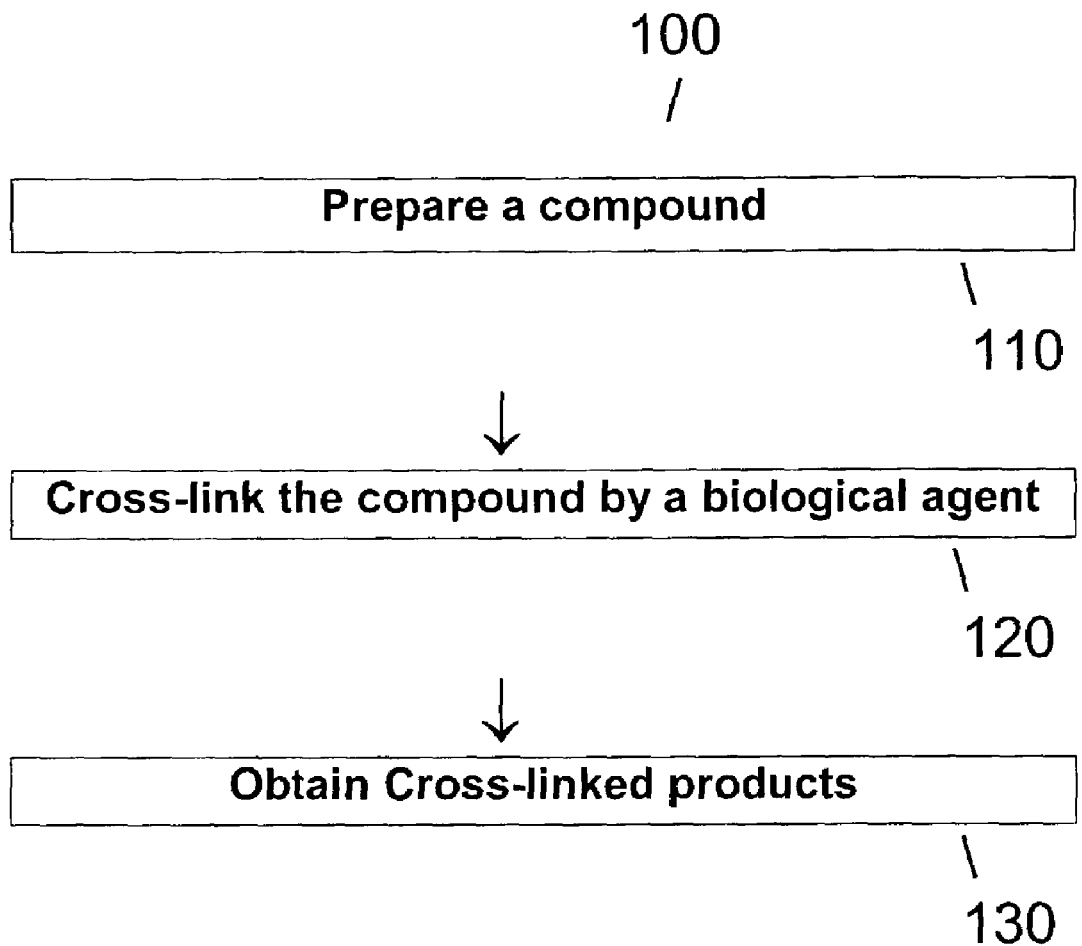
FIG. 1 is a simplified schematic of a method for cross-linking compounds using a biological agent.

The invention relates to a method of cross-linking compounds using biological agents. FIG. 1 depicts a method 100 of cross-linking at least one compound using a biological agent. At step 110, the compound is prepared. Preparation of the compound includes, but is not limited to, purification of native proteins, polypeptides, peptides or other compounds to be cross-linked, biological synthesis or modification of proteins, polypeptides or peptides by expression or overexpression of bioengineered proteins, polypeptides or peptides, or chemically modifying or automatically synthesizing the compound to be cross linked.

Compounds that can be cross-linked by the methods described herein include polypeptides, naturally occurring proteins, peptides, crude proteinaceous substances, or modified forms or mimetics of the aforementioned compounds with saccharides, fatty acids, steroids, purines, pyrimidines, structural analogs, derivatives, or combinations thereof.

Other naturally occurring or synthetic molecule compounds that can be cross-linked and used in the methods herein include numerous chemical classes, though typically they are organic molecules, including small organic molecules. Candidate compounds generally contain functional groups necessary for a structural interaction with proteins, particularly hydrogen bonding; and typically include at least an amine, carbonyl, hydroxyl or carboxyl group, and, preferably, at least two of these functional chemical groups. The candidate compounds may include cyclical carbon or heterocyclic structures and/or aromatic or polyaromatic structures substituted with one or more of the above functional groups.

Typically, compounds to be cross-linked are substrates for the biological cross-linking agents; however, in yet another aspect of the invention, methods to alter, modify, or purify non-substrate compounds are provided. One example of such a modification is through a specific purification scheme. In another example of such a modification, the invention provides a method of modifying compounds through the addition of functional groups or functional residues to the compounds. As a result, many non-substrate compounds that are useful in a cross-linked form can be cross-linked by the biological agents of the invention.

At step 120, the compound is cross-linked by a biological agent, for example, through an enzymatic reaction. As a result of the cross-linking activity of the biological agent, at step 130, cross-linked products of the compound are formed.

The cross-linking method 100 of the invention requires specificity, interaction, or recognition between the compound to be cross-linked and the biological agent. For example, when a biological agent, such as an enzyme having cross-linking ability, is used, the compounds to be cross-linked must be recognized by the biological agent. Generally, biological agents used for cross-linking include various enzymes, purified from biological sources or synthesized de novo. For example, the biological agents may be obtained from any biological source such as an animal, plant, or microorganism. The biological agents may be a naturally occurring enzyme, purified intracellularly or extracellularly in its native form, or may be a recombinant biological agent produced by using genetic engineering techniques or cell engineering techniques, or modified by protein engineering techniques or the biological agent may be synthesized de novo.

Preferably, the biological agents chosen exhibit broad substrate specificity such that a broad range of compounds/substrates are cross-linked using the method 100. For example, microbial transglutaminases, microbial lactases, and microbial bilirubin oxidases typically have broadder substrate specificity than their counterparts in higher organisms. Increasing the range of substrates that can be cross-linked by a biological agent increases the value and usefulness of the agent.

Thus, in one aspect of the invention, the native or recombinant biological agents used are altered, modified, or purified through a specific purification scheme such that the modified biological agents used have broader substrate specificity and cross-link a broad range of compounds, even compounds that are not natural substrates for the non-modified biological agents.

The biological agents chosen may or may not require many accessory co-factors, coenzymes, or other factors, and preferably do not. For example, microbial transglutaminases do not require $Ca^{2+}$, but other tansglutaminases may require $Ca^{2+}$ for cross-linking to occur.

Exemplary biological agents useful for the cross-linking reactions of the present invention include but are not limited to various enzymes such as transferases, transglutaminases, oxidoreductases (i.e., enzymes classified under the Enzyme Classification number E.C. 1 in accordance with the Recommendations (1992) of the International Union of Biochemistry and Molecular Biology (IUBMB)), or combinations thereof.

An example of biological agents useful in methods of the present invention includes transglutaminases. Various types of transglutaminases are known and vary depending on the source from which they are obtained. Suitable transglutaminases include but are not limited to transglutaminases derived from microorganisms (microbial transglutaminase), fish transglutaminases, nematode transglutaminases, and mammalian transglutaminases. Microbial transglutaminases include transglutaminases purified from microorganisms from the Genus *Streptoverticillium, Bacilus, Steptomyces*, etc., such as those reported in Motoki et al, U.S. Pat. Nos. 5,156,956, titled "Transglutaminase", filed on Jul. 1, 1991; and Washizu et al, Biosci. Biotech. Biochem., 58(1), 82–87 (1994), which are incorporated herein by reference. Exemplary mammalian transglutaminases include liver transglutaminase, plasma factor XIIIa, platelet placental factor XIIIa, hair-follicle transglutaminase, epidermal transglutaminase, cellular transglutaminase, tissue transglutaminase, nerve-derived transglutaminase, guinea pig liver transglutaminase, and prostate transglutaminase.

Other examples of biological agents include oxidoreductases (E.C. 1), which are enzymes capable of catalysing redox reactions. Exemplary oxidoreductases include laccases or related enzymes that act on molecular oxygen ($O_2$) yielding water ($H_2O$) without peroxide ($H_2O_2$), oxidases or related enzymes that act on molecular oxygen ($O_2$) to yield peroxide, and peroxidases or related enzymes that act on peroxide (e.g. $H_2O_2$) to yield water ($H_2O$).

Suitable oxidoreductases include but are not limited to sulfhydryl oxidases, lipoxygenases, phenolases, catechol oxidase (E.C. 1.10.3.1), polyphenol oxidases (tyrosinase (E.C. 1.14.18.1)), laccases (lysyl oxidases (E.C. 1.10.3.2)), bilirubin oxidases (E.C. 1.3.3.5), ascorbic acid oxidases (E.C. 1.10.3.3), ceruloplasmin (E.C. 1.16.3.1), peroxidase (E.C. 1.11.1), isomerases (e.g. protein disulfide-isomerases), reductases (e.g. protein-disulfide reductases), and combinations thereof.

Thus, one embodiment of the invention provides methods for producing biological agents, such as various enzymes, capable of cross-linking a wide variety of compounds. In one aspect of this embodiment, the biological agents used are purified intracellularly or extracellularly in their native form and used in this form or modified. The cross-linking biological agents may be purified through various protein purification procedures. Examples of purification procedures include but are not limited to ammonia sulfate precipitation, salting in reactions, salting out reactions, and column chromatography employing the principles of size-exclusion, cationic or anionic exchange, and various affinity interactions, etc. Alternatively, the biological agents used are obtained by recombinant means. One embodiment of the invention provides methods of cloning and expressing the genes for the biological agents, and purifying recombinant forms of the biological agents using genetic engineering, cell engineering, or protein engineering techniques.

In one aspect of the invention, the biological agents used are kept in a reversibly inactive form and are activated into active forms during cross-linking reaction. The invention provides a method of producing reversibly inactive forms of native or recombinant biological agents. The purpose of doing so is to avoid non-specific reactions or loss of activity during storage, to increase the expression level of the biological agents, and to allow for the expression of the native or recombinant biological agents without affecting the health and viability of the host cell. The reversibly inactive forms of the biological agents are useful to target specific compounds to be cross-linked, and to obtain desirable cross-linked products.

The mechanism of the molecular weight-increasing, cross-linking reaction by biological agents of the present invention is as follows. In general, functional groups of one or more compounds of the present invention are recognized and temporarily bound by the biological agent or agents to form intermolecular or intramolecular cross-linking bonds. For example, an oxidase catalyzes a reaction in which protons are removed from a substrate in the presence of molecular oxygen, thereby forming oxidized products and water. As another example, a transglutaminase catalyzes a reaction in which an acyl group is transfered from an acyl donor compound to an acyl receptor on the same or another compound. In the case of transglutaminases, intramolecular or intermolecular $\gamma$-glutamyl-$\epsilon$-lysyl cross-linked products are formed. Typically, a $\gamma$-carboxy-amide group of a peptide-bound glutamine residue is the acyl donor and primary amino groups in a variety of compounds such as peptides, proteins, nucleic acids and similar compounds, such as the $\epsilon$-amino group of a lysine residue in a peptide or polypeptide chain, may function as acyl acceptors.

Typical functional groups that can be oxidized or acyl-transferred are found in the amino acid side chains of proteins, peptides, nucleic acids, and similar compounds. Exemplary functional groups include, but are not limited to, amines, carbonyl, hydroxyl or carboxyl groups, including the $\gamma$-carboxy-amide group of a glutamine residue, the $\epsilon$-amino group of a lysine residue, the hydroxyl group of tyrosine, the sulfhydryl group of cysteine, and the imidazole group of a histidine residue, as well as primary amino groups in a variety of compounds, such as peptides, proteins, nucleic acids, and similar compounds, and combinations thereof.

The reaction of the compound with the biological agent (FIG. 1, step 120), may take place in the form of a solution, slurry or paste, but the reaction conditions and concentrations of both the biological cross-linking agents and the compounds to be cross-linked are selected depending on the properties of the reactants and cross-linked products of interest. For example, the amount of the biological agents and compounds to be used, the time and temperature of the reaction and the pH of the reaction solution are varied as necessary. In addition, such a solution, slurry or paste of the reactants may be obtained not only in aqueous form but also as an emulsion with an oil or fat and, as necessary, may be blended with additives such as salts, saccharides, proteins, perfumes, moisture keeping agents, and coloring agents.

III. Production of Biological Agents and Compounds

The invention provides recombinant biological cross-linking agents and methods for producing and purifying recombinant biological cross-linking agents in vitro through recombinant DNA technology. Furthermore, the invention also provides recombinant compounds to be cross-linked, and methods of producing and purifying the compounds to be cross-linked by the biological agents, either in native form or using recombinant means.

Host cells transformed with nucleic acid sequences encoding the biological agents or compounds of the invention may be cultured under conditions suitable for expression and recovery of the biological agents or compounds from cell cultures. The recombinant biological agents and compounds of the invention produced may be secreted or contained intracellularly depending on the nature of the biological agent or compound and/or the vector used. They may be expressed as soluable compounds or agents, or as insoluble aggregates or inclusion bodies. For example, expression vectors containing polynucleotides that encode the biological agents and compounds of the invention may be designed to contain signal sequences which help to direct secretion of the biological agents and compounds through a prokaryotic or eukaryotic cell membrane and into extracellular environments or culture media. As another example, a host cell line may be chosen for its ability to modulate the expression of the inserted sequences or to process the expressed proteins or peptides in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

In addition, recombinant constructions known in the art may be used to join all or portions of the nucleotide coding sequences for the biological agents or compounds to be cross-linked to nucleotide sequences encoding other polypeptide domains. The polypeptide domains can be used to facilitate the purification of the biological agents and compounds of the invention. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). In addition, it may be useful to include cleavable linker sequences between the coding sequences and the purification facilitating domains, such as those specific for Factor XA or enterokinase (Invitrogen, San Diego, Calif.) to facilitate purification and separate the purification-facilitating domains after purification.

For example, using the purification methods described herein, the invention provides recombinant transglutaminases (TGase) from *Streptoverticillium mobaraense* (ATCC 29032) and *Streptoverticillium cinnamoneum* (ATCC 11874) that are overexpressed in *E. coli* and have been purified in vitro with a better yield, higher purity, and higher enzymatic activity than has been possible previously. Until now, identifying a safe, efficient, and cost-effective method of producing recombinant TGase has met with little success. Native TGase purified from natural sources, such as the secreted bacterial TGase from culture medium, has two primary disadvantages. First, contamination from impurities and pathogens is a problem. Yet, current methods of producing recombinant microbial TGase using various expression vectors and/or chemically-synthesizing the coding sequences according to the preferred codon usage of the host E. coli cell generally results in low enzymatic activity, low yield, high cost, and protein precipitate/aggregate formation during purification (Washizu et al., Biosci Biotechnol Biochem 1994, Takehana et al., Biosci Biotechnol Biochem 1994, EP 0,481,504 and U.S. Pat. Nos. 5,420,025 and 6,013,498). Secretion expression of TGase by E. coli, yeast or the like, results in a yield that is disadvantageously very small despite the use of large scale cell cultures, such as large fermentation equipment. Further, it has been found that since bacterial TGase is independent on calcium, the expression of active TGase is fatal to the microorganism because the enzyme acts on proteins necessary for the survival of the host cells.

For the reasons above and for other reasons, the invention provides improved, novel methods of producing recombinant biological agents and recombinant compounds. For example, recombinant TGase, recombinant serum albumin, recombinant cellulase, recombinant bovine serum albumin (BSA), recombinant tumour necrosis factors (TNF-α), and recombinant epidermal growth factor receptor (EGF-R), are among the useful biological agents and compounds prepared using the purification methods of the invention. The methods are efficient, cost-effective to be used among various biological agents and compounds to be cross-linked as described herein, and the products are safe for pharmaceutical or medical uses.

Isolation of genomic DNA of the biological agents and compounds to be cross-linked can be accomplished by methods known in the art. Conventional methods and commercial kits are readily available to purify genomic DNA. Alternatively, genes for the biological agents and compounds to be cross-linked may be obtained as a cDNA, by cloning and screening methods known in the art, for example, by constructing and screening various DNA libraries, direct PCR cloning, and other recombinant means.

As mentioned previously, methods well known to those skilled in the art may be used to construct cloning vectors containing appropriate transcriptional and translational control elements and DNA sequences. Exemplary techniques are described in Sambrook, J. et al. (1989) Molecular Cloning, A Laboratory Manual, Cold Spring Harbor Press, Plainview, N.Y., Ausubel, F. M. et al. (1989) Current Protocols in Molecular Biology, John Wiley & Sons, New York, N.Y., and Green, E. et al. (1997) Genome Analysis, A Laboratory Manual, Cold Spring Harbor Press, Plainview, N.Y.

In order to carry out certain aspects of the invention, primers may be used to amplify the genomic or cDNA sequences of the biological agents and compounds to be cross-linked. For example, DNA fragments containing all or portions of the transglutaminase coding sequences may be used as probes for cloning of other transglutaminase (TGase) genes. For instance, SEQ ID No. 1 and SEQ ID No. 2 are provided herein as primers for cloning of transglutaminase genes from *Streptomyces mobaraensis* ATCC 29032 (SM TGase). Also provided are SEQ ID No. 3 and SEQ ID No. 4 for cloning of transglutaminase genes from *Streptomyces cinnamoneus* ATCC 11874 (SC TGase). Also provided are SEQ ID No. 5 and SEQ ID No. 7, which are the DNA sequences encoding the mature TGase proteins from *Streptomyces mobaraensis* ATCC 29032 and *Streptomyces cinnamoneus* ATCC 11874, respectively. In addition, SEQ ID No. 13 and SEQ ID No. 14 are provided as primer pair for cloning of cellulase gene from *Humicola grisea* var. thermoides ATCC 16453.

A genomic sequence of interest may include nucleic acid sequences present between the initiation codon and the stop codon, containing all of the introns that are normally present in a native chromosome. It may further include the 3' and 5' untranslated regions found in the mature mRNA. It may further include specific transcriptional and translational regulatory sequences, such as promoters, enhancers, etc., including about 1 kb to 10 kb or more of flanking genomic DNA at either the 5' or 3' end of the transcribed region. Genomic DNA may be isolated as a DNA fragment of 100 kb or smaller that is substantially free of flanking chromosomal sequence. Sequences required for proper tissue and stage specific expression also can be cloned from genomic DNA flanking the coding region (either 3' or 5') and/or internal regulatory sequences, sometimes found in introns.

The sequence of the 5' flanking region may be modified to effect promoter elements and/or enhancer binding sites, to provide developmental regulation in tissues where the gene of interest is expressed. Tissue-specific expression is useful for determining the pattern of expression of the gene, and for providing promoters that mimic the native pattern of expression. Naturally-occurring polymorphisms in the promoter region are useful for determining natural variations in expression, particularly those that may be associated with diseases.

Alternatively, mutations may be introduced into the promoter region to alter the expression of the nucleic acid sequence. Methods for the identification of specific DNA motifs involved in the binding of transcriptional factors are known in the art, e.g., sequence similarity to known binding motifs, gel retardation studies, etc. For examples, see Blackwell et al. (1995) Mol Med 1: 194–205; Mortlock et al. (1996) Genome Res. 6: 327–33; and Joulin and Richard-Foy (1995) Eur J. Biochem 232: 620–626. Regulatory sequences may be used to identify cis acting sequences required for transcriptional or translational regulation of the expression of the biological agents and compounds of the invention, especially in different tissues or stages of development, and to identify cis acting sequences and trans acting factors that regulate or mediate gene expression. Such transcription or translational control regions may be operably linked to a gene for the biological agents and compounds in order to promote expression of wild type or altered genes of interest in cultured cells, or in embryonic, fetal, or adult tissues, and for gene therapy.

Techniques for in vitro mutagenesis of cloned genes are known. Examples of protocols for site-specific mutagenesis may be found in Gustin et al. (1993) Biotechniques 14:22; Barany (1985) Gene 37:111–23; Colicelli et al. (1985) Mol Gen Genet 199:537; and Prentki et al. (1984) Gene 29:303–13. Methods for site specific mutagenesis can be found in Sambrook et al., Molecular Cloning: A Laboratory Manual, CSH Press 1989, pp. 15.3–15.108; Weiner et al., Gene 126:35-41 (1993); Sayers et al. Biotechniques 13:592–6 (1992); Jones and Winistorfer, Biotechniques 12:528–30 (1992); Barton et al., Nucleic Acids Res 18:7349–55 (1990); Marotti and Tomich, Gene Anal Tech 6:67–70 (1989); and Zhu, Anal Biochem 177:120–4 (1989).

The nucleic acid compositions of the invention may encode all or a part of the polypeptides for the biological agents and compounds to be cross-linked. Double- or single-stranded fragments of the DNA sequence may be obtained by chemically synthesizing oligonucleotides in accordance with conventional methods, by restriction enzyme digestion, by PCR amplification, etc. For the most part, DNA fragments will be of at least 15 nucleotides, usually at least 18 nucleotides or 25 nucleotides, and may be at least about 50 nucleotides. Small DNA fragments are useful as primers for PCR, hybridization screening probes, etc. Larger DNA fragments, i.e., greater than 100 nt, are useful for production of a protein or polypeptide.

Altered nucleic acid sequences encoding the biological agents and compounds to be cross-linked may include deletions, insertions, or substitutions of different nucleotides resulting in a polynucleotide that encodes the same or a functional equivalent of the compounds to be cross-linked. The encoded protein may also contain deletions, insertions, or substitutions of amino acid residues, which produce silent changes and result in functionally equivalent compounds that can be be cross-linked. The altered nucleic acid sequences for the biological agents and compounds of the invention may be used to generate changes in promoter strength or sequences of the encoded proteins, for example, to promote folding of the encoding proteins, or to decrease substrate fidelity. Deliberate amino acid substitutions may be made on the basis of similarity in polarity, charge, solubility, hydrophobicity, hydrophilicity, and/or the amphipathic nature of the residues as long as the biological activity of compounds to be cross-linked is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine. Such alterations to the compound to be cross-linked may be made to increase expression, allow for purification, or to add cross-linking groups to make the compound more reactive to the biological cross-linking agent.

In order to obtain biological agents in compounds to be cross-linked, cloning of the genes encoded for biological agents and compounds of the invention into an expression vector may be necessary. An expression vector may contain necessary elements for transcription and/or translation of the inserted coding sequences. Expression vectors and systems known in the art may be employed for producing full length or only portions of the polypeptides of the biological agents and compounds of the invention.

For long-term, high-yield production of recombinant proteins, stable expression of the DNA construct of biological agents and/or compounds to be cross-linked is preferred. For example, cell lines which stably express the biological agent and/or compounds may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type. As another example, a host cell strain may be chosen for its ability to modulate the expression of the inserted sequences or to process the expressed proteins or peptides in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

With the availability of the protein or fragments in large amounts, the recombinant biological agents and compounds to be cross-linked may be isolated and purified in accordance with conventional methods. Again, see Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & sons, New York, N.Y. A lysate may be prepared of the expression host and the lysate purified using HPLC, exclusion chromatography, gel electrophoresis, affinity chromatography, or other purification techniques. The purified proteins will generally be at least about 80% pure, preferably at least about 90% pure, and may be up to and including 100% pure. Pure is intended to mean free of other proteins, as well as cellular debris.

Production of the recombinant biological agents and compounds to be cross-linked may be as insoluble inclusion body fusion proteins. For example, expression of recombinant transglutaminase proteins may be toxic to a host cell; thus an expression vector for high level-expression of insoluble protein is chosen to avoid the expression of soluble active transgluamineases. Alternatively, genomic DNA encoding the mature proteins for the biological agents and compounds to be cross-linked are produced and isolated without signal peptides in order to express the recombinant proteins inside the host cells without processing through the secretory pathway of the host cells. For example, when purifying mature recombinant TGase proteins having cross-linking activity, it is found that the expression of secreted TGases may be toxic to the host cells, reactive to the host proteins, and/or self reactive, resulting in low yield and low activity of recombinant TGase proteins.

In yet another approach, natural, modified, or recombinant nucleic acid sequences encoding the biological agents and the compounds to be cross-linked may be ligated to a heterologous sequence to encode a fusion protein. For example, it may be useful to encode chimeric proteins that can be recognized by commercially available antibodies. A fusion protein may also be engineered to contain a cleavage site located between the encoding sequences for the biological agent and the compounds, and the heterologous protein sequences, so that the biological agent and the compounds may be cleaved and purified away from the heterologous moiety.

In summary, nucleotide sequences of biological agents and/or compounds to be cross-linked can be engineered using methods generally known in the art in order to alter coding sequences for a variety of reasons, including but not limited to, alterations which modify the cloning, processing, and/or expression of the gene product, and, specifically, to decrease substrate specificity of the biological agents and/or add cross-linking sites to the compounds to be cross-linked.

IV. Purification, Inactivation, Storage and Reactivation of Biological Agents and Compounds to be Cross-Linked One embodiment of the invention provides cloning and purification of recombinant biological agents and compounds to be cross-linked. For example, in bacterial systems, a number of expression vectors that direct expression of fusion proteins such that they are easily purified may be used. Such vectors include, but are not limited to, the multifunctional *E. coli* cloning and expression vectors such as BLUESCRIPT (Stratagene), in which the sequence encoding the biological agent and compounds of the invention may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

As an example, for ease in purification, expression of recombinant transglutaminases can be done by cloning of genomic TGase gene into an inducible pET expression vector, combined with a 6×-histidine-tagged fusion protein system. Such an expression vector provides for expression of a fusion protein containing the coding sequence of a biological agent or candidate compound of the invention fused to a nucleic acid encoding six histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying the recombinant transglutaminase. A discussion of expression vectors for constructing fusion proteins is provided in Kroll, D. J. et al. (1993; DNA Cell Biol. 12:441–453). Other purification techniques include but are not limited to ligand affinity chromatography, antibody affinity chromatography, ion-exchange chromatography, hydrophobic interaction chromatography, ultrafiltration reverse phase high-performance liquid chromatography, isoelectric point electrophoresis, etc. Exemplary techniques are described in Scopes, R. K. (1994) Protein Purification: Principles and Practice (Third Edition), Springer-Verlag, New York, N.Y.

Thus, one aspect of the invention provides recombinant 6X-histidine-tagged TGase fusion proteins, including SEQ ID No. 9, a DNA sequence encoding a recombinant 6×-His-TGase fusion protein of *Streptomyces mobaraensis* ATCC 29032, and SEQ ID No. 11, a DNA sequence encoding a recombinant 6×-His-TGase fusion protein from *Streptomyces cinnamoneus* ATCC 11874. The invention also provides SEQ ID No. 10, a translated amino acid sequence encoding the recombinant 6×-His-TGase fusion protein of *Streptomyces mobaraensis* ATCC 29032 (about 355 amino acids), and SEQ ID No. 12, a translated amino acid sequence encoding the recombinant 6×-His-TGase fusion protein of *Streptomyces cinnamoneus* ATCC 11874 (about 355 amino acids).

As another example, recombinant serum albumin can be expressed from an expression vector contiaining a cloned serum albumin insert as secreted recombinant proteins and purified from the extracellular cultures medium through ammonia sulfate percipitation. Another example of purification of compounds to be cross-linked through recombinant mean is the purification of recombinant cellulase. Genomic DNA of a cellulase gene was subcloned into pET expression system (Novagen) for over-expression as intracellular recombinant protein inclusion bodies and purification through fusion protein purification techniques. The invention provides SEQ ID No. 13 and SEQ ID No. 14 as primers for cloning of cellulase gene.

In another embodiment of the invention, recombinant cross-linking biological agents and compounds to be cross-linked are purified in an inactive form to prevent cross-linking reaction during storage. Thus, the invention provides inactive forms of recombinant biological agents that can be reversibly reactivated into active forms. Such a treatment is advantageous as it prevents self-cross-linking activity of the biological agent during purification and storage, which often results in low purification yield, loss of enzymatic activity, and precipitation of protein aggregates. Conditions have been optimized for inactivating and reactivating recombinant TGases; however such purification methods can be applied to other biological agents and/or compounds to be cross-linked.

The method involves first purifying the recombinant biological agents or compounds to be cross-linked under denaturing conditions using a denaturant, such as solubilizing a protein inclusion body produced as described above with a high concentration of guanidine, such as about 6M to about 9M of guanidine, preferably about 8M of guanidine, prepared in a pH buffering agent, e.g., tris buffer titrated with hydrochloric acid to a pH of about 6 to about 8. In addition to a denaturant, the solution for solubilizing includsion bodies may also contain other salts, such as up to 0.8M of sodium chloride (NaCl) or potassium chloride (KCl), e.g., about 0.2M of NaCl or about 0.5M of NaCl. One example of such lysis or solubilizing buffer includes about 6M guanidine titrated with hydrochloric acid (guanidine-HCl) to a pH of about 7.9, prepared in a solution containing about 20 mM of Tris buffer, about 5 mM imidazole, and about 0.5M sodium chloride (NaCl). Other denaturants, such as about 6 M to about 8 M of urea may also be used.

In one embodiment, the purification of the recombinant biological agents or compounds to be cross-linked is done in one single column step using affinity column chromatograpgy. After binding to an affinity column, washing is generally performed under less stringent conditions, i.e. low salt or low ionic strength conditions. One example of a wahsing buffer includes about 6M guanidine titrated with hydrochloric acid (guanidine-HCl) to a pH of about 7.9, prepared in a solution containing about 20 mM of Tris buffer, about 20 mM imidazole, and about 0.5M sodium chloride (NaCl). After washing, elution of the purifed recombinant proteins is generally performed under high stringent conditions, i.e. high salt or high ionic strength conditions. One example of a elution buffer includes about 6M guanidine titrated with hydrochloric acid (guanidine-HCl) to a pH of about 7.9, prepared in a solution containing about 20 mM of Tris buffer, about 0.5 M imidazole, and about 0.5M sodium chloride (NaCl).

After the recombinant biological agents or compounds to be cross-linked were purified in the presence of a denaturant thereby deactivating them, they are refolded, preferably without regeneration of activity. Removing the denaturant and refolding the recombinant biological agents or compounds to be cross-linked is accomplished by diluting the volume of the purified recombinant proteins through dialysis, ultrafiltration, or the like, preferably in a solution other than an activation solution to keep them in inactive form. Suitable dilution or dialysis solutions include, but are not limited to, phosphate buffered saline (PBS), Tris-HCl buffer with low concentrations of salts (e.g., sodium clloride, potassium chloride, and others), etc. After dialysis, an additional concentrating step may be required to concentrate the recombinant protein solutions; for example, using commercially available concentrators or dialysing in a storage buffer having high concentration of glycerol (e.g., about 20% or higher, such as about 50% or higher). The purified recombinant proteins can be purified to at least about 95% homogeneity, as judged by Coomassie Blue staining and silver staining of a SDS-PAGE gel.

In one embodiment of the invention, the refolding, dilution or dialysis solution used does not include a reducing agent, including, but not limited to, DTT, glutathione, etc., at a concentration up to about 0.5 M. One example of a refolding solution includes about 0.75 M of arginine, about 50 mM of Tris base titrated with hydrochloric acid (Tris-HCl) to a pH of about 8.0, about 50 mM of potassium chloride (KCl), and about 0.1 mM of a metal chelator, such as EDTA. Another example of a refolding solution includes about 100 solution volumes of PBS solution. One example of a dialysis solution includes about 50 mM of Tris-HCl (at a pH of about 7.9), about 50 mM of KCl, about 0.1 mM of EDTA, and about 50% of glycerol. These steps or reactions can be kept to incubate at low temperature, such as at around room temperature or less, such as about 4° C., for more than one hour, such as about 48 hours.

The invention also provides storage buffer for the inactive biological agents. For example, the storage buffer includes up to about 200 mM of a salt, up to about 5 mM of a metal chelator, up to about 70% glycerol, and up to about 200 mM of Tris base titrated with hydrochloric acid, acetic acid, or other titration acid/base, to a pH of about 5 to about 11. In another embodiment, the storage buffer used does not include a reducing agent, including, but not limited to, DTT, glutathione, etc., at a concentration up to about 0.5 M.

As an example, inactive recombinant TGase fusion proteins were purified in a denaturing solution, refolded, and stored at a concentration of about at least 1 mg/ml in a storage buffer, which includes about 50 mM of Tris-HCl (at a pH of about 8.0), about 50 mM of KCl, about 0.1 mM of EDTA, and about 50% of glycerol. Another example of storage buffer includes about 50 mM of Tris-acetic acid (at a pH of about 6.0), about 50 mM of KCl, about 0.1 mM of EDTA, and about 50% of glycerol.

As another examples, compounds to be cross-linked can be denatured, refolded, and stored in various buffer solutions for long-term storage and changing their specificity and accessibility of functional groups toward the biological agent chosen during cross-linking reaction. Exemplary compounds to be cross-linked that exhibit change of reactivity to the chosen biological agent through after such procedures include, but are not limited to, bovine serum albumin (BSA), histone H3 protein, glucose oxidase, ovalbumin, myelin basic protein (MBP), recombinant serum albumin, recombinant cellulase, recombinant bovine serum albumin (BSA), recombinant tumour necrosis factors (TNF-α), and recombinant epidermal growth factor receptor (EGF-R). Accordingly, the purification, inactivating, storing, and/or reactivating methods as decribed herein can be employed to other compounds to be cross-linked as well.

Once the biological agents have been purified, inactivated and stored, they are later reactivated for use as cross-linking agents. In one embodiment, the purified recombinant biological agents are denatured, refolded, and inactivated and reactivated such that their substrate specificity are altered, modified, or extended to react with and cross-link a broader range of compounds than their native biological gaent counterparts. Examples include the purified recombinant SM TGase and SC TGase fusion proteins, however, the methods described herein can be employed to other biological agents as well.

Another embodiment of the invention provides an activation solution including at least one reducing agent, deionized water, and a pH-buffering agent for adjusting the pH. Exemplary reducing agents include dithiothreitol (DTT), glutathione, and the like, at a concentration up to about 0.5 M. In another embodiment, the activation solution further includes up to about 70% of glycerol. The pH of the activation solution can be about pH 5 to about pH 11, such as between about pH 6 to about pH 9. The activation solution can further include phosphate-buffered saline solution (PBS). One formulation of the activation solution includes about 10 mM DTT, about 20% to about 30% of glycerol, about 50 mM Tris buffer, and tritated with hydrochloric acid to a pH of about 7.4. Another formulation includes PBS solution, about 30% of glycerol, about 50 mM Tris buffer, titrated with acetic acid to a pH of about 6. In another formulation (discussed in the next section), the activation solution is the same solution that is used for the cross-linking reaction. For example, the invention provides a method of activating the TGases and cross-linking a compound in a single step.

For example, the activity of a recombinant transglutaminase purified and inactivated by methods of the present invention was assayed. The unit of transglutaminase activity was defined by the method of the Folk and Cole (J. Biol. Chem., vol 241, p. 5518 (1966)) activity assay. Through repeated experimentation, it was found that the activity of the recombinant transglutaminases could be restored only when the purified recombinant transglutaminases intentionally were kept in an inactive form in the storage buffer. The enzymatic activity of the inactivated recombinant transglutaminase fusion proteins was restored by the addition of an activation solution, which included at least a reducing agent and a pH-buffering agent for adjusting the pH of the composition. For example, a good reducing agent found to restore the enzymatic activity of recombinant transglutaminase fusion proteins was dithiothreitol (DTT), at a concentration up to about 0.5 M. However, other reducing agents, such as glutathione and others, may also be used. The enzymatic activity of the active recombinant transglutaminase is at least about 0.5 unit/mg in the presence of the activation solution, such as about 1 unit/mg when about 0.005 unit per 1 mg of β-casein substrate was used in the activity assay. Also, it was found that the addition of glycerol helped to activate the activity of the recombinant transglutaminase fusion proteins, probably by stablizing the refolded structure of the recombinant transglutaminase fusion proteins.

Surprisingly, there was a change of solution color from clear to yellow when the recombinant transglutaminases were activated. The change of solution color was observed for both the purified recombinant SM TGase fusion protein and the purified recombinant SC TGase fusion protein. The results were measured as an increase in absorbance value from 400 nm to 500 nm from about 0.0001 to about 0.1 or more, such as an increased absorbance value of about 0.1 or more from 400 nm to 500 nm. For example, the solution includes an increased absorbance value of about 0.1 or more at $OD_{450}$, such as about 0.2 or more and as much as about 2.0 or more. For example, in the presence of the activation solution, there was an increase in $OD_{450}$ value for the solution of the purified recombinant SM TGase and SC TGase fusion proteins, such as an increased $OD_{450}$ value from about 0.1 or less to about 0.1 or more when are of the purified recombinant SM TGase and SC TGase fusion proteins activated, e.g., $OD_{450}$ value at about 0.3 or more in the presence of one activation solution and $OD_{450}$ value at about 2.0 or more in the presence of another activation solution.

Furthermore, the enzymatic activity was found to work at a wide range of temperature and, surprisingly, the activity was found optimal at room temperature as compared to high temperature, such as 37° C. The result is unexpected, as most microbial $Ca^{2+}$-independent transglutaminases have higher enzymatic activity at a temperature of 30° C. or more (see U.S. Pat. No. 6,100,053 and EP-0,481,504).

The purified recombinants SM TGase and SC TGase fusion proteins exhibit enzymatic activity at broad pH optimum, from about 5 to about 11, such as about 5.5 to about 9. Further, it was found that the recombinant SM TGase fusion protein exhibit higher cross-linking abtility at pH of about 6 as compared to higher pH that is very different from native SM TGase and from other microbial transglutaminases which exhibit higher enzymatic activity only at neutral or higher pH (U.S. Pat. No. 6,100,053 and WO 00/70026).

One advantage of storing recombinant transglutaminases in an inactive form is that, after reactivation, the initial level of enzymatic activity is not decreased. Native transglutaminases, when purified, usually precipitate out of solution into white protein aggregates when purified. Additionally, native TGases sometimes react with their own protein species to form cross-linked transglutaminases. As a result, enzymatic activity is lost over time. However, an even greater benefit of the inactivation/activation reaction has been discovered. Native transglutaminases react only with a limited number of substrates, such as casein and other crude protein mixtures. For these reasons, cross-linking applications for native transglutaminases is extremely limited by substrate specificity. A large number of proteins, such as bovine serum albumin (BSA), glucose oxidase, and ovalbumin, as well as most peptides, do not react with native transglutaminases. However, the reversibly inactive biological agents described herein react with a large number of compounds after purification, inactivation and activation. The methods described herein decrease the fidelity of the TGases for substrates, allowing reaction with candidate compounds including, but not limited to, bovine serum albumin (BSA), histone H3 protein, tumour necrosis factors (TNF-α and other TNFs), glucose oxidase, epidermal growth factor receptor (EGF-R), ovalbumin, and myelin basic protein (MBP), as well as most naturally occurring peptides, and synthetic peptides having at least one glutamine residue.

V. Compounds to be Cross-Linked

Candidate compounds to be cross-linked are obtained from a wide variety of sources including combinatorial libraries of synthetic or natural compounds. For example, numerous means are available for random and directed synthesis of a wide variety of organic compounds, proteins or peptides, and biomolecules, including expression of randomized oligonucleotides and oligopeptides. Alternatively, libraries of natural compounds in the form of bacterial, fungal, plant and animal extracts are readily available or can be produced. Moreover, naturally or synthetically produced compounds are readily modified through conventional chemical, physical and biochemical means, and may be used to produce combinatorial libraries. Known pharmacological chemicals may be subjected to directed or random chemical modifications, such as acylation, alkylation, esterification, amidification, etc. to produce structural analogs.

In addition to recombinant production, the whole compounds or fragments of compounds to be cross-linked may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using an Applied Biosystems 431A peptide sythesizer (Perkin Elmer). Various fragments of compounds to be cross-linked may be chemically synthesized separately and combined using chemical methods to produce the full-length molecule.

At least two types of candidate compounds or synthetic peptides, as representatives of compounds to be cross-linked by a biological agent, may be used. One type includes internal residues or functional groups that are reactive to a biological agent and can be cross-linked by the biological agent of the invention. The other type includes an addition of one or more terminal residues or functional groups to be reactive to a biological agent. For example, the presence or addition of at least one isodityrosine residue to candidate compounds is required for cross-linking reactions mediated by peroxidase/ascorbate oxidase (Cooper et al., 1983). As another example, the presence or addition of hydroxylysine or lysine residue in candidate compounds is necessary for cross-linking reactions carried out by lysyl oxidases through oxidative deamination of these reactive residues (Palamakambura et al., 2002).

However, when a biological agent, such as peroxidases are used, a number of amino acid residues and derivatives thereof may serve as the reactive residues for forming the cross-linked bonds and generally require the presence of peroxide ($H_2O_2$) in addition to the biological agent (the peroxidases, in this case) and the candidate compounds to the cross-linked (Otte et al, 2000; Fu et al., 2002).

As an example, candidate compounds in the reaction mixture of the cross-linking may include one or more candidate protein or peptide that may be expressed or otherwise present in a host cell. For example, candidate compounds include polyamino acids, cell-membrane-associated proteins, tumor-associated antigens, cytokines, cytokine receptors, bacterial toxins, whole bacterial cells, viral coat proteins, whole viruses, viral glycoproteins, cell wall-derived coat proteins, peptides, synthetic peptides, any modification of the aforementioned compounds, and derivatives thereof; and each candidate compound may be one or more members of library of proteins or peptides, such as a collection of human ESTs, a total library of human ESTs, a collection of domain structures (e.g. Zn-finger protein domains), or a totally random peptide library.

As another example, the candidate compounds in the mixture of the cross-linking may include one or more antigens, e.g., disease-associated antigens, cancer-specific antigens, and cancer-associated antigens, and combinations thereof. Exemplary antigens include tumor surface antigens among others, such as B-cell idiotypes, CD20 on malignant B cells, CD33 on leukemic blasts, and HER2/neu on breast cancer. Other examples include oncogenes or mutated tumor suppressor genes that have lost its tumor-suppressing function and may render the cells more susceptible to cancer. Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth—cancer. Examples of the tumor suppressor genes that can be used include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. p53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer.

Other candidate compounds to be cross-linked include, but are not limited to, cytokines, cytokine receptors, growth factor receptors and combinations thereof. Exemplary growth factors include, but are not limited to, epidermal growth factors (EGFs), transferrin, insulin-like growth factor, transforming growth factors (TGFs), interleukin-1, and interleukin-2. The candidate compounds may also be one or more cell surface proteins or receptors, such as various matrix metalloproteases, receptors associated with coronary artery disease, e.g. platelet glycoprotein lib/IIIa receptor, with autoimmune diseases such as CD4, CAMPATH-1 and surface components of the bacterial cell wall. As another examples, the candidate compounds may also be one or more proteins or peptides associated with human immune and/or allergic diseases, such as those inflammatory mediator proteins, and peptides and proteins derived from HLA class I and class II peptides, auto-antigens, e.g. Interleukin-1 (IL-1), tumor necrosis factor (TNF), leukotriene receptor and 5-lipoxygenase, and adhesion molecules such as VCAM-1 and VCAM/VLA4. In addition, IgE may also serve as the candidate antigen because IgE plays pivotal role in type I immediate hypersensitive allergic reactions such as asthma.

Further, the candidate compounds may also be a viral surface or core protein which may serve as an antigen to trigger immune response of the host. Examples of these viral proteins include, but are not limited to, glycoproteins (or surface antigens, e.g., GP120 and GP41) and capsid proteins (or structural proteins, e.g., P24 protein); surface antigens or core proteins of hepatitis A, B, C, D or E virus (e.g. small hepatitis B surface antigen (SHBsAg) of hepatitis B virus and the core proteins of hepatitis C virus, NS3, NS4 and NS5 antigens); glycoprotein (G-protein) or the fusion protein (F-protein) of respiratory syncytial virus (RSV); surface and core proteins of herpes simplex virus HSV-1 and HSV-2 (e.g., glycoprotein D from HSV-2).

Advantageously, a mixture of one or more candidate compounds as described herein can be cross-linked by the biological agents of the invention to generate high potency polyvalent antigens. For example, a mixture of two or more candidate compounds was successfully used for generating cross-linked products for immunizing animals such as mice, rats, rabbits and others. The antibodies or antisera obtained from using cross-linked products generated by the methods of the invention revealed an increased titer to each component of the mixture (each candidate compound) than antibodies or antisera obtained from using conventional non-cross-linked antigens. For example, the titer of the antisera has been found at least about 1000 or more to each component of the candidate compounds chosen and the difference has been found to be at least two fold higher titer, as much as about 30 fold or higher, and in some cases, about 80 fold or higher.

VI. Peptide Compositions

As discussed, many compounds can be used for cross-linking, but in one embodiment, such compounds have a peptide component. Peptides to be used for cross-linking may be produced by recombinant means or may be chemically synthesized by, for example, the stepwise addition of one or more amino acid residues in defined order using solid phase peptide synthetic techniques. The peptides may need to be synthesized in combination with other proteins and then subsequently isolated by chemical cleavage. For example, short chain peptides can be synthesized using an automatic peptide synthesizer. Alternatively, different short chain peptide species can be obtained from a long polypeptide chain, whether naturally-occurring or synthetic, through enzymatic reactions and other means, and by purification of different peptide species using column chromatography.

In one embodiment, the functional groups for reacting to a chosen biological agent, e.g., lysine and glutamine residues for transglutaminases, may be located internally, i.e., not at the peptide termini, within the peptide chain. Such a peptide monomer having a length of about 100 or less amino acids typically is a weak antigen for stimulating immune responses in animals.

As an example, peptides having at least one lysine (K) and at least one glutamine (Q) residue are prepared to be cross-linked. One example of a peptide having internal reactive glutamine and lysine residues is the β-amyloid peptide. An exemplary synthetic β-amyloid peptide (SEQ ID NO. 15) is provided herein. One example of a biological agent used herein is a purified recombinant transglutaminase from *Streptoverticillium mobaraense* (ATCC 29032). By incubating the exemplary synthetic peptides with the purified recombinant microbial transglutaminase, a γ-glutamyl-ε-lysyl crosslinking/bridging bond is formed between the lysine and glutamine residues.

As a result of the activity of the biological agent, cross-linked peptides having a length of at least two peptide monomers are formed. The length of the resulting cross-linked peptides may be about 100 amino acids or more, and up to about 1000 amino acids or more. The cross-linked peptides can be used as antigens for stimulating immune responses in animals. In general, cross-linked antigens can induce higher immune responses than monomeric antigens.

In an alternative embodiment, peptide monomers are synthesized that have reactive residues or functional groups on one or both termini. For example, when transglutaminase is chosen as the biological agent, the sequence of each monomer may vary as long as each monomer has one ore more glutamine (Q) residues on either one of the N-terminus or the C-terminus. Optionally, each monomer may have one or more lysine (K) residues. One example of a peptide having terminal reactive glutamine and lysine residues is a synthetic Bovine Serum Albumin peptide 5 (BSA5) having an amino acid sequence of SEQ ID NO. 16.

The peptide compositions of the invention may comprise naturally occurring amino acid residues or may contain non-naturally occurring amino acid residues such as certain D-isomers or chemically modified naturally occurring residues. These latter residues may be required, for example, to facilitate or provide conformational constraints and/or limitations to the peptides. The selection of a method of producing the subject peptides depends on factors such as the required type, quantity and purity of the peptides as well as ease of production and convenience.

The peptides prepared for cross-linking reaction may first require chemical modification for use in vivo since the peptides themselves may not have a sufficiently long serum and/or tissue half-life. Chemical modification of the subject peptides may also be important to improve their antigenicity including the ability for certain regions of the peptides to act as B and/or T cell epitopes. Such chemically-modified synthetic peptides are referred to herein as "analogues". The term "analogues" extends to any functional, chemical, or recombinant equivalent of the peptides of the present invention characterized, in one embodiment, by their possession of at least one B cell epitope. The term "analogue" is also used herein to extend to any amino acid derivative of the peptides as described above. Analogues of the synthetic peptides contemplated herein include, but are not limited to, peptides with modifications to their side chains, peptides with unnatural amino acids and/or their derivatives or other molecules incorporated during peptide synthesis, and peptides treated with cross-linking agents or other agents which impose conformational constraints on the peptides or their analogues.

Examples of side chain modifications contemplated by the present invention include modifications of amino groups such as by reductive alkylation (e.g. reaction with an aldehyde followed by reduction with Sodium borohydride ($NaBH_4$), amidination with methylacetimidate, acylation with acetic anhydride, carbamoylation of amino groups with cyanate, trinitrobenzylation of amino groups with 2,4,6-trinitrobenzene sulphonic acid (TNBS), acylation of amino groups with succinic anhydride and tetrahydrophthalic anhydride, and pyridoxylation of lysine with pyridoxal-5'-phosphate followed by reduction with sodium borohydride ($NaBH_4$). In addition, the guanidine group of arginine residues may be modified by the formation of heterocyclic condensation products with reagents such as 2,3-butanedione, phenylglyoxal and glyoxal.

The carboxyl group of side chains of peptides may be modified by carbodiimide activation via O-acylisourea formation followed by subsequent derivitisation, for example, to a corresponding amide. Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

VII. Cross-linking a Compound by Transglutaminase

Figure 2:
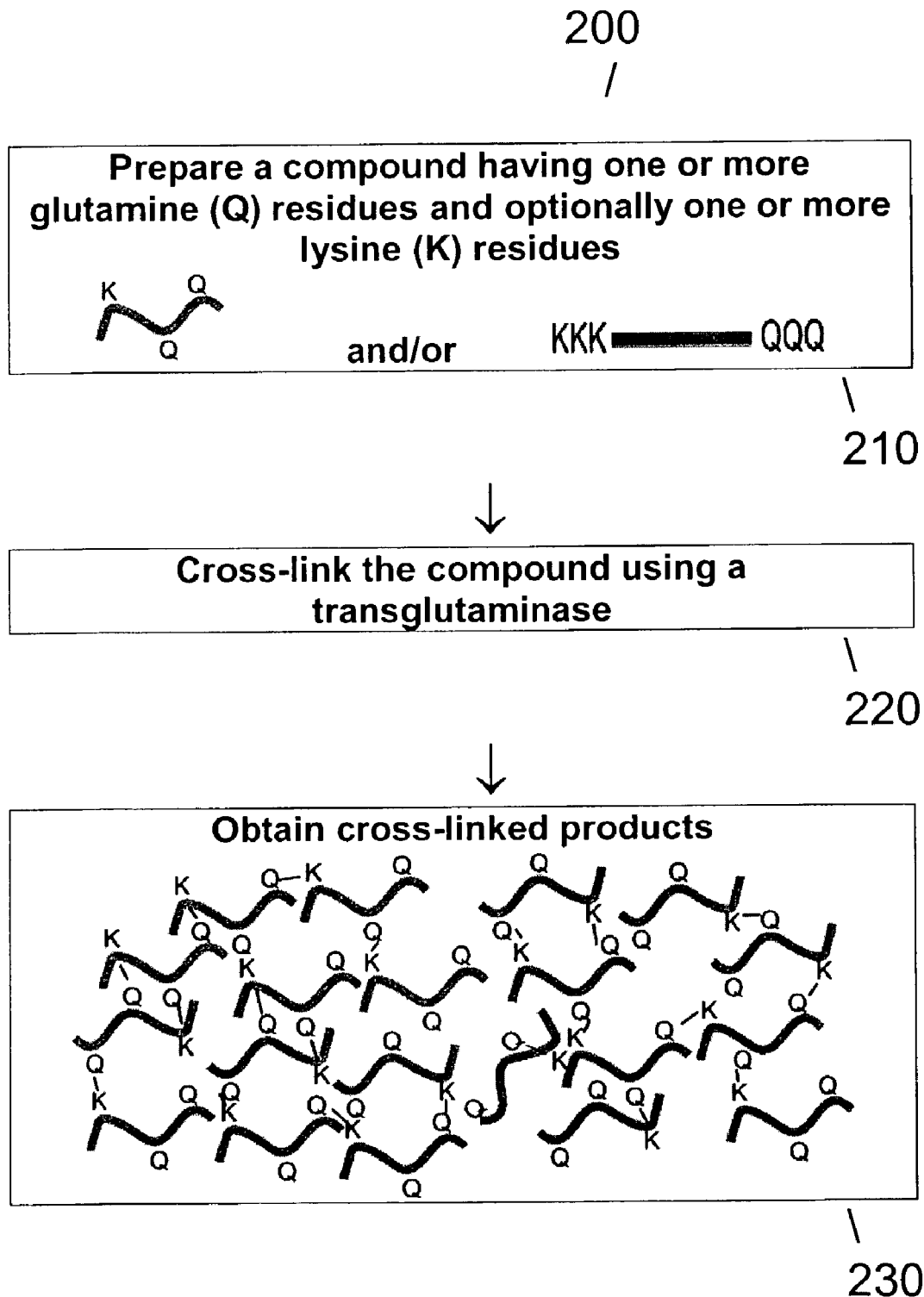
FIG. 2 is a simplified schematic of a method for cross-linking synthetic compounds having lysine residues on one terminus and glutamine residues on the other terminus using a transglutaminase.

The present invention also provides methods for cross-linking a compound using a transglutaminase. FIG. 2 depicts such a method 200. At step 210, at least one compound having one or more glutamine (Q) residues is prepared. Glutamine residue is provided as the acyl donor for transglutaminase-mediated cross-linking reaction. Typically, any compound having an amino group can be used as the acyl receptor for transglutaminase activity. Optionally, the compound further includes one or more lysine (K) residues to be used as acyl receptors. In some cases, one compound having one or more glutamine (Q) residues on one terminus and one or more lysine (K) residues on the other terminus is prepared. For example, the lysine and glutamine residues as illustrated at step 210 are either located internally—i.e., not at the termini but within the polypeptide chain—and/or terminally.

At step 220, the at least one compound is cross-linked by a biological agent, such as a transglutaminase, and cross-linked products having a size of at least two compound monomers are formed at step 230. For example, by incubating the compound with a purified recombinant microbial transglutaminase in the presence of an activation solution under suitable conditions, a γ-glutamyl-ε-lysyl crosslinking/bridging bond is intermolecularly or intramolecularly formed between the lysine and glutamine residues. As an example, a number of native proteins, recombinant proteins, in purified or crude forms, are substrates or modified to be substrates, as described herein using methods of the invention and can be cross-linked accordingly. Exemplary transglutaminase-reactive substrates that are cross-linked by the purified recombinant transglutaminase include various plant proteins and animal proteins, such as β-casein, β-lactoglobulin, ovalbumin, myosin, actin, serum albumin, gelatin, collagen, etc., and combinations thereof. Exemplary non-substrates that can be modified to be cross-linked by the purified recombinant tranglutaminase include, but are not limited to, recombinant bovine serum albumin (BSA), histone proteins, glucose oxidase, recombinant tumour necrosis factors, myelin basic protein (MBP), recombinant epidermal growth factor receptor (EGF-R), recombinant serum albumin, recombinant cellulase, and combinations or derivatives thereof.

FIG. 2 illustrates the use of a transglutaminase; however other biological agents may be employed, such as transferases, oxidoreductases, and the like. Reaction conditions for cross-linking of compounds by other biological agents will vary depending on the agents, the compounds, the volume of the reaction and the concentration and reactivity of the reactants. The cross-linked products can be checked or visualized on a standard SDS-PAGE gel or other means to show the completion of the cross-linking reaction.

VII. Cross-Linked Compounds as Therapeutics

Figure 3:
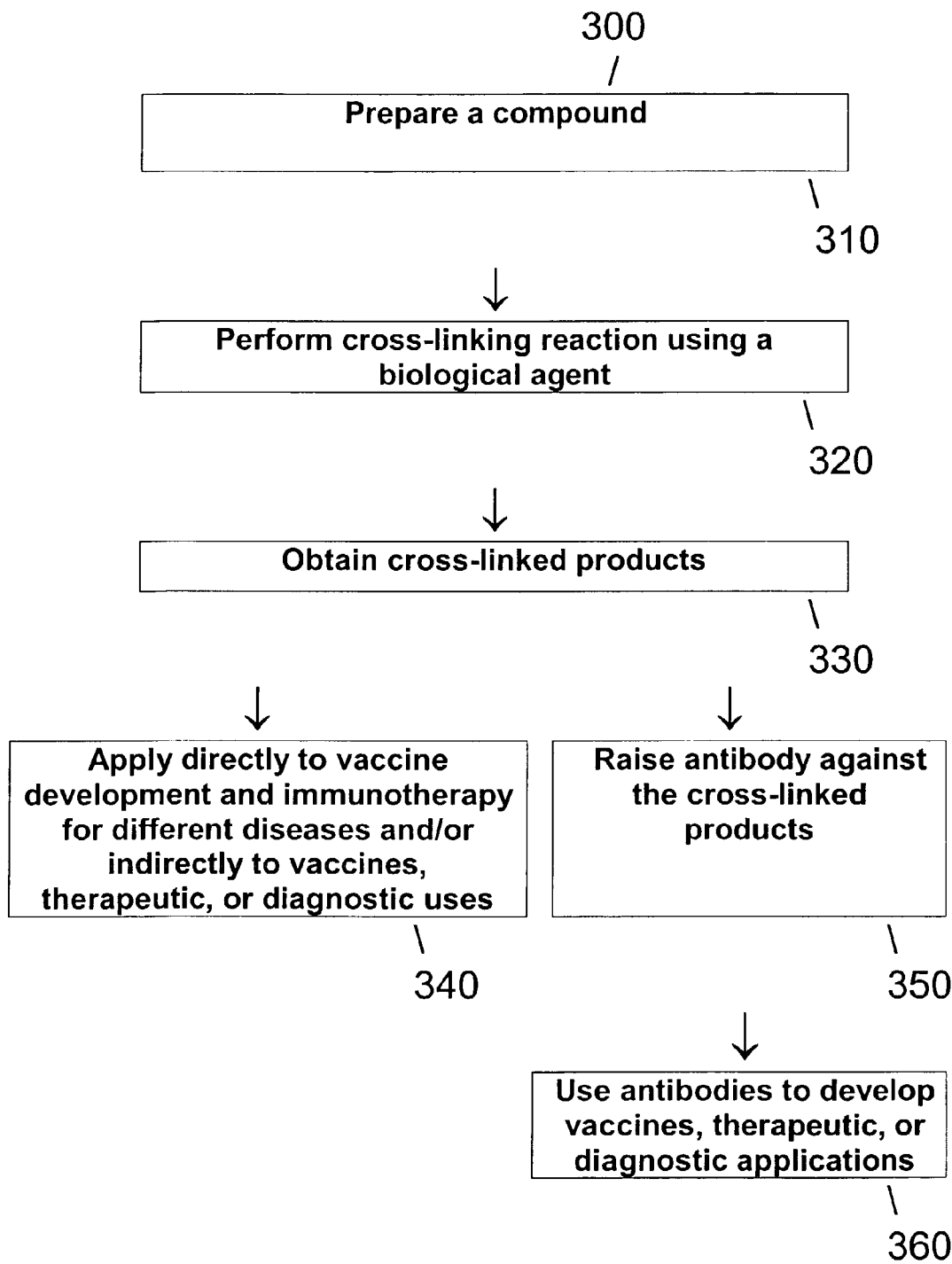
FIG. 3 is a simplified schematic fo a method for producing therapeutic agents using the methods of the present invention.

FIG. 3 is a flow chart 300 illustrating the uses and the applications of cross-linked products. At step 310, candidate compounds are prepared or synthesized. At step 320, the compounds are cross-linked by a biological agent, such as a purified recombinant biological agent, e.g., a purified recombinant transglutaminase from *Streptoverticillium mobaraense* (ATCC 29032).

At step 330, cross-linked products having a length of at least two compound monomers are formed and obtained. The cross-linked products can be used as polyvalent antigens for stimulating immune responses in animals. The invention provides evidence that polyvalent antigens using the cross-linked products of the invention can induce increased immune responses than monomeric antigens. The in vivo results obtained have demonstrated an increase in immune response for polyvalent antigens prepared according to the methods of the invention than conventional non-cross-linked antigens (See Experimental). For example, the titer of the antisera has been found at least about 1000 or more to each monomeric component of the candidate compounds chosen. In addition, the antibodies or antisera obtained exhibited an increased titer of about at least 10 fold or higher, such as about 30 fold or higher, as much as about 80 fold or higher.

At step 340, the cross-linked products are used directly as therapeutic agents to be administered into animals for treating diseases associated with the compound monomer. The therapeutic agents and vaccines of the present invention are used to induce acquired immunity through both active immunity and passive immunity. Such immunotherapy application can be tested in animal models before administration to humans. In addition, the cross-linked products, polyvalent antigens, and antibodies of the invention are used in diagnostic kits for various diseases associated with the biological agents and candidate compounds of the invention.

At step 350 the cross-linked products are used to produce antibodies in animals. The antibody produced is then used for developing vaccines and diagnostic kits at step 360. Thus, the polyvalent antigens using cross-linked products of the present invention can be used as therapeutic agents or vaccines directly, or used as antigens to elicit antibodies in an animal, where the antibodies are then used as therapeutic agents or vaccines.

For example, when candidate compounds such as disease-associated antigens, cancer-specific antigens, and cancer-associated antigens are cross-linked by the methods of the invention, the resulting cross-linked products can be used as polyvalent antigens for direct immunizarion to induce immune response in animals and treat the associated diseases or cancers. In addition, antibodies selected against these antigens can be used in a wide variety of therapeutic and diagnostic applications, such as treatment of cancer by direct administration of the antibody alone (e.g., humanized antibodies for immunizing humans) or conjugated with a radioisotope or cytotoxic drug, or in a combination therapy involving co-administration of cross-linked polyvalent antigens or antibody thereof with a chemotherapeutic agent, or in conjunction with radiation therapy.

Therapeutics and Vaccines in General

For immunizing the polyvalent antigens of the invention and for the production of antibodies, various hosts including goats, rabbits, rats, mice, humans, and others, may be immunized by injection with the cross-linked products obtained or fragments or oligopeptides thereof that have immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin), aluminum hydroxide, and *Corynebacterium parvum* are especially preferable. Other immune response enhancing compounds include conjugate compound, co-stimulating factor for immune response, DNA vaccine, and combinations thereof. The above mentioned immune response enhancing compounds can be formulated and immunized together with the vaccine and therapeutics of the invention or as one or more boosts for stimulating immune response after the vaccine and therapeutics of the invention has been used as the vaccine.

The vaccines and therapeutics of the present invention can be administered by oral, pulmonary, nasal, aural, anal, dermal, ocular, intravenous, intramuscular, intraarterial, intraperitoneal, mucosal, sublingual, subcutaneous, or intracranial route. In pharmaceutical, personal care, or veterinary applications, the vaccines and therapeutics described herein may be topically administered to any epithelial surface. Such epithelial surfaces include oral, ocular, aural, anal and nasal surfaces, to treat, protect, repair or detoxify the area to which they are applied.

The therapeutics and vaccines of the invention can be incorporated into a variety of formulations for therapeutic administration. Particularly, compounds, cross-linked products, biological agents, and polyvalent antigens that modulate the activity of one or more disease-related proteins are formulated for administration to patients for the treatment of disease. More particularly, the cross-linked products, biological agents, polyvalent antigens and compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration can be achieved in various ways, including oral, buccal, rectal, parenteral, intraperitoneal, intradermal, transdermal, intracheal, etc., administration.

The therapeutics and vaccines of the invention may be systemic after administration or may be localized by the use of an implant or a surface patch that acts to retain the active dose at the site of implantation or contact. Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The therapeutics and vaccines of the present invention can be administered alone, in combination with each other, or they can be used in combination with other known compounds. In pharmaceutical dosage forms, the therapeutics and vaccines may be administered in the form of their pharmaceutically acceptable salts, or they may also be used alone or in appropriate association, as well as in combination with other pharmaceutically active compounds.

For oral preparations, the therapeutics and vaccines can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Alternatively, the therapeutics and vaccines can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The therapeutics and vaccines can be utilized in aerosol formulation to be administered via inhalation. The therapeutics and vaccines of the present invention can be formulated into pressurized acceptable propellants such as dichlorodifluoromethane, propane, nitrogen and the like.

Furthermore, the therapeutics and vaccines can be made into suppositories by mixing with a variety of bases such as emulsifying bases or water-soluble bases. The therapeutics and vaccines of the present invention can be administered rectally via a suppository. The suppository can include vehicles such as cocoa butter, carbowaxes and polyethylene glycols, which melt at body temperature, yet are solidified at room temperature.

Pharmaceutically acceptable excipients, such as vehicles, adjuvants, carriers or diluents, are readily available to the public and known in the art. Further, pharmaceutically acceptable auxiliary substances, such as pH adjusting and buffering agents, tonicity adjusting agents, stabilizers, wetting agents and the like, are readily available to the public and known in the art.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes may be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like. For preparing the liposomes, the procedure described by Kato et al. (1991) J. Biol. Chem. 266:3361 may be used. Briefly, the lipids and lumen composition containing the nucleic acids are combined in an appropriate aqueous medium, conveniently a saline medium where the total solids will be in the range of about 1–10 weight percent. After intense agitation for short periods of time, from about 5–60 sec., the tube is placed in a warm water bath, from about 25° C. to about 40° C. and this cycle repeated from about 5 to 10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules.

The exact dosage of the chosen formulation for the chosen method of administration will be determined by the medical practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of therapeutics and vaccines will be specific to particular cells, conditions, locations, etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of therapeutics and vaccines of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

A therapeutically effective dose refers to that amount of active ingredient—for example, cross-linked products or antibodies thereof, which ameliorates one or more symptoms or conditions. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

Those of skill will readily appreciate that dose levels can vary as a function of the specific compound or therapeutics, the severity of the symptoms and the susceptibility of the subject to side effects. Some of the specific therapeutics are more potent than others. Preferred dosages for a given compound or therapeutic agent are readily determinable by those of skill in the art by a variety of means. A preferred means is to measure the physiological potency of a given therapeutic agent.

Cancer Immunotherapy

Methods of the invention can be used to cross-link a variety of compounds including, but not limited to, cytokines, cytokine receptors, growth factors, and growth factor receptors, to be adminstered in animals to induce immune response and treat various diseases and cancers. As an example, one or more disease-associated antigens, cancer-specific antigens, and cancer-associated antigens, and combinations thereof can be cross-linked by the biological agents of the invention and obtained for formulating therapeutics and vaccine as direct immunotherapy. As another example, high-level expression of EGF receptor (EGF-R) can be found in a wide variety of human epithelial primary tumors. Several murine monoclonal antibodies have been demonstrated to be able to bind EGF receptors, block the binding of ligand to EGF receptors, and inhibit proliferation of a variety of human cancer cell lines in culture and in xenograft models (Mendelsohn and Baselga (1995) Antibodies to growth factors and receptors, in Biologic Therapy of Cancer, 2nd Ed., J B Lippincott, Philadelphia, pp607–623). As another example, TGF-α was found to mediate an autocrine stimulation pathway in cancer cells. Thus, polyvalent antigens and antibodies selected against these cytokines and growth factors and generated using the method of the present invention can be used as a novel approach of immunotherapy.

As another example, polyvalent tumor suppressor antigens, oncogens, and/or antibodies derived therefrom, such as a mutated tumor suppressor gene product, produced by using the method of the present invention can be used to intervene and block the interactions of the gene product with other proteins or biochemicals in the pathways of tumor onset and development.

Infectious Diseases

As another example, cell surface proteins, receptors, and surface components of an infectious agent (e.g., a bacteria, fungi, virus, algae, protozoan, and parasites, etc.) can be prepared by the methods of the invention to formulate therapeutics and vaccines for inducing active and/or passive acquired immunity for treating or diagnosing the associated diseases. For example, one or more viral glycoproteins and/or one or more infectious agents with or without being attenuated can be cross-linked by the biological agents of the invention. The cross-linked products can be formulated into therapeutics and vaccines for treating or diagnosing the one or more diseases related to the virus and infectious agents. This approach is very powerful for designing multivalent vaccine and has the advantages of being able to treat more than one diseases in a single vaccine formula.

Immune-Related and/or Autoimmune Diseases

As another example, for the treatment of patients with mycosis fungoides, generalized postular psoriasis, severe psorisis, and rheumatoid arthritis, antibodies against $CD_4$ has been tested in clinical trials. Further, antibodies against lipid-A region of the gram-negative bacterial lipopolysaccharide have been tested clinically in the treatment of septic shock. As another example, antibodies against CAMPATH-1 has also been tested clinically in the treatment against refractory rheumatoid arthritis (Vaswani et al. (1998) "Humanized antibodies as potential therapeutic drugs" Annals of Allergy, Asthma and Immunology 81:105–115). Thus, polyvalent antigens and antibodies selected against these cell surface molecules, cytokines, receptors, and growth factors generated by using the method of the present invention can be used to treat a variety of immune-related and/or autoimmune diseases.

As an example to proteins or peptides associated with human immune and/or allergic diseases, studies have shown that the level of total serum IgE tends to correlate with severity of such diseases, especially in asthma. Burrows et al. (1989) "Association of asthma with serum IgE levels and skin-test reactivity to allergens" New Engl. L. Med. 320: 271–277. Thus, polyvalent IgE antigens and/or antibodies selected against IgE prepared by using the method of the present invention may be used to reduce the level of IgE or block the binding of IgE to mast cells and basophils in the treatment of allergic diseases without having substantial impact on normal immune functions.

Uses of Cross-Linked Amyloid Peptides as Preventing or Therapeutic Agents Against Alzheimer's Disease.

The invention also provides a method of using cross-linked β-amyloid peptides for preventing or as therapeutic agents for Alzheimer's disease. Embodiments of the invention pertain to cross-linked products, vaccines, compounds, and pharmaceutical compositions that bind to natural β-amyloid peptides, modulate the aggregation of natural β-amyloid peptides and/or inhibit the neurotoxicity of natural β-amyloid peptides ("modulator compounds"). It has recently been reported (Games et al. (1995) Nature 373: 523–527) that an Alzheimer-type neuropathology has been created in transgenic mice. The transgenic mice express high levels of human mutant amyloid precursor protein and progressively develop many of the pathological conditions associated with Alzheimer's disease. Further, numerous studies in humans also point to a direct pathological role for the β-amyloid peptide in Alzheimer's diseases.

The β-amyloid modulator compounds of the invention comprise a peptidic structure and corss-linked products thereof prepared by the methods described herein. The peptide structure preferably based on β-amyloid peptide, composed entirely of L- or D-amino acids. In various embodiments, the peptidic structure of the modulator compound comprises cross-linked products of L- or D-amino acid sequences corresponding to a L-amino acid sequence found within natural β-amyloid peptide, or L- or D-amino acid sequences that are scrambled or substituted versions of the natural β-amyloid peptide amino acid sequence. A D-amino acid sequence is a retro-inverso isomer of a L-amino acid sequence. In addition, the L- or D-amino acid peptidic structure of the modulator can be designed based upon a subregion of natural β-amyloid peptide.

For example, an amino acid sequence having lysine and glutamine residues located internally within each amyloid peptide chain as illustrated in SEQ ID No. 15 was designed. A synthetic peptide monomer having a length of about 100 or less amino acids is a weak antigen for stimulating immune response in animals. However, such synthetic peptides may increase antigenic activity if they have been cross-linked by a biological agent. One example of biological agent used herein is a purified recombinant transglutaminase from Streptoverticillium mobaraense (ATCC 29032). By incubating the synthetic peptides with the purified recombinant microbial transglutaminase, a γ-glutamyl-ε-lysyl crosslinking/bridging bond is intermolecularly formed between the lysine and glutamine residues.

A modulator drawn to this embodiment preferably includes cross-linked products of 3–20 L- or D-amino acids, more preferably 3–10 L- or D-amino acids and even more preferably 3–5 L- or D-amino acids. The peptidic structures of the modulator can have free amino- and carboxy-termini. Alternatively, the amino-terminus, the carboxy-terminus or both may be modified. For example, an N-terminal modifying group can be used that enhances the ability of the modulator to inhibit β-amyloid aggregation. Preferred amino-terminal modifying groups include cyclic, heterocyclic, polycyclic and branched alkyl groups. Examples of suitable amino-terminal modifying groups include cis-decalin-containing groups, biotin-containing groups, fluorescein-containing groups, a diethylene-triaminepentaacetyl group, a (−)-mentboxyacetyl group, an N-acetylneuraminyl group, a phenylacetyl group, a diphenylacetyl group, a triphenylacetyl group, an isobutanoyl group, a 4-methylvaleryl group, a 3-hydroxyphenylacetyl group, a 2-hydroxyphenylacetyl group, a 3,5-dihydroxy-2-naphthoyl group, a 3,4-dihydroxycinnamoyl group, a (.+−.)-mandelyl group, a (.+−.)-mandelyl-(.+−.)-mandelyl group, a glycolyl group, a benzoylpropanoyl group and a 2,4-dihydroxybenzoyl group. Moreover, the amino- and/or carboxy termini of the peptide modulator can be modified to alter a pharmacokinetic property of the modulator (such as stability, bioavailability and the like). Preferred carboxy-terminal modifying groups include amide groups, alkyl or aryl amide groups (e.g., phenethylamide) and hydroxy groups (i.e., reduction products of peptide acids, resulting in peptide alcohols). Still further, a modulator compound can be modified to label the modulator with a detectable substance (e.g., a radioactive label).

The modulators of the invention can promote amyloid aggregation or, more preferably, can inhibit natural amyloid aggregation. In a preferred embodiment, the cross-linked modulator compounds modulate the aggregation of natural β-amyloid peptides (β-AP). In a preferred embodiment, the β-amyloid modulator compounds of the invention are comprised of a β-amyloid aggregation core domain and a modifying group coupled thereto such that the modulator alters the aggregation or inhibits the neurotoxicity of natural β-amyloid peptides when contacted with the peptides. Furthermore, the modulators are capable of altering natural β-amyloid peptide aggregation when the natural β-amyloid peptides are in a molar excess amount relative to the modulators. Pharmaceutical compositions comprising the modulators of the invention, and diagnostic and treatment methods for amyloidogenic diseases using the modulators of the invention, are also disclosed.

This invention pertains to cross-linked products, modulator compounds, and pharmaceutical compositions thereof, that can modulate the aggregation of amyloidogenic proteins and peptides, in particular therapeutic and vaccines that can modulate the aggregation of natural β-amyloid peptides and inhibit the neurotoxicity of natural β-amyloid peptides. In one embodiment, the invention provides an amyloid modulator compound including amyloidogenic proteins, cross-linked products thereof, or peptide fragments thereof, with or without coupling directly or indirectly to one or more modifying groups. Preferably, the modulator compound modulates the aggregation of natural amyloid proteins or peptides when contacted with the natural amyloidogenic proteins or peptides. The amyloidogenic proteins, cross-linked products thereof, or peptide fragments thereof, include, but are not limited to, natural β-amyloid peptides, transthyretin (TTR), prion protein (PrP), islet amyloid polypeptide (IAPP), atrial natriuretic factor (ANF), kappa light chain, lambda light chain, amyloid A, procalcitonin, cystatin C, β-2 microglobulin, ApoA-I, gelsolin, calcitonin, fibrinogen, lysozyme, nd combinations thereof.

Another aspect of the invention pertains to methods for treating a subject for a disorder associated with β-amyloidosis. These methods include administering to the subject a therapeutically effective amount of a modulator compound of the invention, such as cross-linked products of peptides derived from SEQ ID No. 15, such that the subject is treated for a disorder associated with β-amyloidosis. Preferably, the disorder is Alzheimer's disease.

Antibody Production

In adition to be used directly in formulating therapeutics and vaccines, the cross-linked products and biological agents of the invention are useful for the production of antibodies. Antibodies may be generated using methods that are well known in the art. Such antibodies may include, but are not limited to, polyclonal antibodies, monoclonal antibodies, chimeric antibodies, humanized antibodies, neutralizing antibodies, single chain, Fab fragments, and fragments produced by Fab expression libraries.

Monoclonal antibodies may be prepared using any technique that provides for the production of antibody molecules by continuous cell lines in culture. These include, but are not limited to, the hybridoma technique, the human B-cell hybridoma technique; mouse, rabbit, and other hybridoma techniques; and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of chimeric antibodies involving the splicing of non-human antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314: 452–454). Alternatively, techniques described for the production of single chain antibodies may be adapted, using methods known in the art, to produce protein-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299). Antibody fragments containing specific binding sites for the cross-linked polyvalent antigens and biological agents of the invention may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) Science 254:1275–1281).

Antibodies are prepared in accordance with conventional methods, where the cross-linked products, polyvalent antigens, and biological agents of the invention are used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

A variety of protocols are known in the art for detecting and measuring either polyclonal or monoclonal antibodies prepared by the methods of the invention and raised specifically for the various cross-linked products, biological agents, and compounds of the invention. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the cross-linked products is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216). Suitable reporter molecules or labels, which may be used to assay binding or interaction of the antibody produced, include radionucleotides, enzymes, fluorescent, chemiluminescent, or chromogenic agents as well as substrates, cofactors, inhibitors, magnetic particles, and the like. As an alternative to using cross-linked products to elicit antibodies, the cross-linked products may be administered alone, as a part of a pharmaceutical, personal care or veterinary preparation or as part of a prophylactic preparation, administered by parenteral or non-parenteral route.

Diagnostics Applications

The invention provides various antibodies raised against the cross-linked products, candidate compounds, and biological agents. Antibodies raised against these therapeutics and vaccines of the invention may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal antigens in patient cells. For example, detection may utilize staining of cells or histological sections, performed in accordance with conventional methods. Cells are permeabilized to stain cytoplasmic molecules. The antibodies raised to the therapeutics and vaccines of the present invention are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

In another embodiment, antibodies that specifically bind the therapeutics and vaccines of the present invention may be used for the diagnosis of conditions or diseases characterized by expression of the compounds, or in assays to monitor patients being treated with the compounds themselves, agonists, antagonists, or inhibitors. The antibodies useful for diagnostic purposes may be prepared in the same manner as those described above for therapeutics. Diagnostic assays for the therapeutics and vaccines include methods which utilize antibodies raised to the cross-linked products, polyvalent antigens, candidate compounds, and biological agents, and a label to detect compounds in human body fluids or extracts of cells or tissues. The antibodies may be used with or without modification, and may be labeled by joining them, either covalently or non-covanently, with a reporter molecule. A wide variety of reporter molecules which are known in the art may be used, several of which are described above.

A variety of protocols including ELISA, RIA, FACS for measuring antigens are known in the art and provide a basis for diagnosing altered or abnormal levels of target protein expression. Normal or standard values for target protein expression are established by combining body fluids or cell extracts taken from normal mammalian subjects, preferably human, with antibody to target protein under conditions suitable for complex formation. The amount of standard complex formation may be quantified by various methods, but preferably by photometric, means. Quantities of protein expressed in subject samples from biopsied tissues are compared with the standard values. Deviation between standard and subject values establishes the parameters for diagnosing disease.

Other Applications

The cross-linked products and biological agents of the invention have been shown to be useful for a variety of industrial purposes, including the field of processing of raw fish paste, tofu noodles, confectionery/bread, food adhesives, sheet-like meat food, yogurt, jelly, gelling of cheese proteins, for improving baking quality of flour, improving taste and texture of food proteins, as well as in leather processing (e.g. casein finishing), etc.

The cross-linked products produced by the biological agents of the invention can also be used as novel protein-derived materials in a wide range of industries including cosmetics such as hair dyeing formulations for the production of keratinous fibre cross links, the production of thermally stable materials such as raw materials of microcapsules, carriers of immobilized enzymes and the like.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Isolation of Genomic DNA from *Streptomyces mobaraensis* and *Streptomyces cinnamoneus*

Cultures of *Streptomyces mobaraensis* (from an ATCC strain, No. 29032) and *Streptomyces cinnamoneus* (from an ATCC Strain, No. 11874) were grown and harvested into cell pellets. The cell pellets were then freeze-dried before being resuspended and washed in double distilled water and centrifuged again. The washed cell pellets were resuspended in lyses buffer (provided in the DNasey Tissue Kit from Qiagen, Inc.), and genomic DNA was purified as described in a protocol of a DNasey Tissue Kit (from Qiagen, Inc.). Genomic DNA from both strains was purified to homogeneity to be used as a Polymerase Chain Reaction (PCR) template for cloning of the microbial transglutaminase genes from *Streptomyces mobaraensis* and *Streptomyces cinnamoneus*.

EXAMPLE 2

Cloning of Transglutaminase Genes

Cloning of transglutaminase genes from *Streptomyces mobaraensis* ATCC 29032 (SM TGase) was accomplished by using purified genomic DNA as a PCR template in a PCR reaction and two primers as the 5' and 3' primers, SEQ ID NO. 1 and SEQ ID NO. 2, respectively. The sequences of SEQ ID NO. 1 and SEQ ID NO. 2 are based on the Gene bank Accession number Y18315 encoding the mature SM TGase polypeptide from *Streptomyces mobaraensis* DSMZ and further include pre-designed extended Nhe I and Hind III recognition sequences respectively.

Cloning of transglutaminase genes from *Streptomyces cinnamoneus* ATCC 11874 (SC TGase) was accomplished by using purified genomic DNA as a PCR template in a PCR reaction and two primers as the 5' and 3' primers, SEQ ID NO. 3 and SEQ ID NO. 4, respectively. The sequences of SEQ ID NO. 3 and SEQ ID NO. 4 are based on the Gene bank Accession number Y08820 encoding the mature SC TGase polypeptide from *Streptomyces cinnamoneus* CBS 683.68 and further include pre-designed extended Nhe I and Hind III recognition sequences, respectively.

PCR for cloning the SM TGase and SC TGase genes were performed for 35 cycles, each cycle at about 94° C. for about 30 seconds, at about 55° C. for about 45 seconds, and at about 68° C. for about 2 minutes, using the thermal enzyme, Advantage-2 DNA polymerase (Clontech). After these cycles, Taq DNA polymerase (Invitrogen) was added to the PCR reactions and incubated at about 72° C. for about 15 minutes to add adenosine (A) overhangs at 3' end of each PCR product.

The synthesized PCR products containing the SM TGase gene and pre-designed Nhe I and Hind III recognition sites were obtained and cloned into a vector, pCR2.1-TOPO (Invitrogen). Positive clones having the insert DNA of SM TGase gene, were sequenced and named as pCR2.1-SMTG. Likewise, the synthesized PCR products containing the SC TGase and pre-designed Nhe I and Hind III recognition sites were obtained and cloned into a vector, pCR2.1-TOPO (Invitrogen). Positive clones having the insert DNA of SC TGase gene, were sequenced and named as pCR2.1-SCTG.

EXAMPLE 3

DNA Sequences of Transglutaminase Genes from Two G(+) Actinomycetes

Sequencing of pCR2.1-SMTG revealed a DNA sequence, SEQ ID No. 5, encoding the mature TGase protein from *Streptomyces mobaraensis* ATCC 29032 without the signal peptide. The translated amino acid sequence is shown as SEQ ID No. 6.

Sequencing of pCR2.1-SMTG revealed a DNA sequence, SEQ ID No. 7, genes encoding the mature TGase protein from *Streptomyces cinnamoneus* ATCC 11874 without the signal peptide. The translated amino acid sequence is shown as SEQ ID No. 8.

Table 1 is a comparison of the two DNA sequences SEQ ID No. 5 (upper sequence) and SEQ ID No. 7 (lower sequence) by BLAST alignment. The alignment indicates about 84% sequence identity between the DNA sequence of the mature TGase protein from *Streptomyces mobaraensis* ATCC 29032 and the mature TGase protein from *Streptomyces cinnamoneus* ATCC 11874.

TABLE 1

Blast alignment of SEQ ID No.5 and SEQ ID No.7.

```
cagcagcggcctggtgccgcgcggcagccatatggctagc-cccga-----ctccgacga  (SEQ ID NO.5)
||||||||||||||||||||||| |||        ||||||
cagcagcggcctggtgccgcgcggcagccatatggctagctcccgggcccctccgatga   (SEQ ID NO.7.)

cagggtcacccctcccgccgagccgctcgacaggatgcccgacccgtaccgtccctcgta
| |||  ||||||||||||||||| ||  ||||| |||  |||
ccgggaaactcctcccgccgagccgctcgacaggatgcctgaggcgtaccgggcctacgg cggcagggccgagacggtcgtcaacaactacatacgcaagtggcagcaggtctacagcca
||||||    |||||||||||||||||||||||||||
aggcagggccactacggtcgtcaacaactacatacgcaagtggcagcaggtctacagtca ccgcgacggcaggaagcagcagatgaccgaggagcagcgggagtggctgtcctacggctg
||||||| | ||| |||| ||||| ||     ||||||| ||
ccgcgacggaaagaaacagcaaatgaccgaagagcagcgagaaaagctgtcctacggttg cgtcggtgtcacctgggtcaattcgggtcagtacccgacgaacagactggccttcgcgtc
|| ||  ||||||| |||| |  |||||||||   ||| |||||
cgttggcgtcacctgggtcaactcgggcccctacccgacgaacagattggcgttcgcgtc cttcgacgaggacaggttcaagaacgagctgaagaacggcaggccccggtccggcgagac
```

TABLE 1-continued

Blast alignment of SEQ ID No.5 and SEQ ID No.7.

```
||||||| || || ||||||| |||||||   || ||||   |||   || ||
cttcgacgagaacaagtacaagaacgacctgaagaacaccagccccgacccgatgaaac gcgggcggagttcgagggccgcgtcgcgaaggagagcttcgacgaggagaagggcttcca
|||||||||||| || ||| |||  || ||||||| |||| ||| |
gcgggcggagttcgagggtcgcatcgccaagggcagtttcgacgaggggaagggtttcaa gcgggcgcgtgaggtggcgtccgtcatgaacagggccctggagaacgcccacgacgagag
||||||||  |||||||||||  ||||||| || ||||||| |
gcgggcgcgtgatgtggcgtccgtcatgaacaaggccctggaaaatgcccacgacgaggg cgcttacctcgacaacctcaagaaggaactggcgaacggcaaogacgccctgcgcaacga
     |||| || ||||||||| ||| ||   |||| || |||| |||   |  ||
gacttacatcaacaacctcaagacggagctcacgaacaacaatgacgctctgctccgcga ggacgcccgttccccgttctactcggcgctgcggaacacgccgtccttcaaggagcggaa
|||   ||  ||           |||||||||| |||||||| |||| |||||  || |
ggacagccgctc9aacttctactcggcgctgaggaacacaccgtccttcaaggaaaggga cggaggcaatcacgacccgtccaggatgaaggccgtcatctactcgaagcacttctggag
|| ||||   ||||||||| ||||||   || |||||||||||||||||||||||||||
cggccaggaccggtcgagttcggccgacaagaggaagtacggcgacccggacgccttccg cggccaggaccggtcgagttcggccgacaagaggaagtacggcgacccggacgccttccg
|| ||||||   |  |  |||||||||||||||||||| ||||||
cgggcaggaccggcggggctcctccgacaagaggaagtacggcgacccggaagccttccg ccccgccccgggcaccggcctggtcgacatgtcgagggacaggaacattccgcgcagccc
|||| || || |||||||||||| |||| | ||||||||  ||
ccccgaccagggtaccggcctggtcgacatgtcgaaggacagaagcattccgcgcagtcc caccagcccggtgagggattcgtcaatttcgactacggctggttcggcgcccagacgga
  ||   ||  ||  |  |||||||||| |||||  || ||   || || || |
ggccaagcccggcgaaggttgggtcaatttcgactacggttggttcggggctcaaacaga agcggacgccgacaagaccgtctggacccacggaaatcactatcacgcgcccaatggcag
|||| |||||| ||    |||||  |  | ||| |||||||| || ||
agcggatgccgacaaaccacatggacccacggcgaccactaccacgcgcccaatagcga cctgggtgccatgcatgtctacgagagcaagttccgcaactggtccgagggttactcgga
||||    ||| ||    ||  |||||| ||| |  |  ||| |||
cctgggccccatgcacgtacacgagagcaagttccggaagtggtctgccgggtacgcgga cttcgaccgcggagcctatgtgatcaccttcatcccaagagctggaacaccgccccga
|||||||||  |||| ||  ||  |||||||||||
cttcgaccgcggagcctacgtgatcacgttcataccaagagctggaacaccgccccgc caaggtaaagcagggctggccgtga
|||| |||  ||||||| |||||||
caaggtggagcaaggctggccgtga
```

Table 2 is a comparison of the two amino acid sequences SEQ ID No. 6 (upper sequence) and SEQ ID No. 8 (lower sequence) by BLAST alignment. The alignment indicates about 270 identical amino acids (middle sequence, about 81% sequence identity) between the amino acid sequence of the mature TGase protein (about 331 amino acids) from Streptomyces mobaraensis ATCC 29032 and the amino acid sequence of the mature TGase protein (about 334 amino acids) from Streptomyces cinnamoneus ATCC 11874.

EXAMPLE 4

Cloning of SM TGase Gene into an Expression Vector

The expression of the TGase genes in an expression vector has to be tightly regulated. A pET expression vector (Studier et al., 1990) was chosen and combined with a 6x-histidine-tagged fusion protein system as a simplified purification scheme for the inducible expression of recombinant TGase protein. The pCR2.1-SMTG plasmid was digested with Nhe I and Hind III and the DNA fragment containing the SM TGase gene was purified from the digest and subcloned into a pET-28a vector (Novagen). Positive clones with SM TGase gene insert, pET28-SMTG, were identified and sequenced.

Sequencing of pET28-SMTG reveals a DNA sequence, SEQ ID No. 9, encoding a recombinant 6x-His-TGase fusion protein of Streptomyces mobaraensis ATCC 29032. The translated amino acid sequence, SEQ ID No. 10, encoding the recombinant 6x-His-TGase fusion protein of Streptomyces mobaraensis ATCC 29032 (about 355 amino acids) is similar to the sequence of a transglutaminase from Streptoverticillium spp. Strain-8112 (Kanaji et al., 1994; Washizu et al., 1994; EP-A-0481 504). However, the recombinant TGase includes the extended 6x-His-tagged 24 amino acids in the N-terminus (MGSSHHHHHHSSGLVPRGSH-MASP-), which might help for the recombinant SM TGase fusion protein to fold properly in its structure.

TABLE 2

Blast alignment of SEQ ID No.6 and SEQ ID No.8.

```
DSDDDRVTPPAEPLDRMPDPYRPSYGRAETVVNNYIRKWQQVYSHRDGR      (SEQ ID NO.6)
   SDDR TPPAEPLDRMP+ YR   GRA TVVNNYIRKWQQVYSHRDG+
SRAPSDDRETPPAEPLDRMPEAYRAYGGRATTVVNNYIRKWQQVYSHRDGK    (SEQ ID NO.8)

KQQMTEEQREWLSYGCVGVTWVNSGQYPTNRLAFASFDEDRFKNELKNGRP
KQQMTEEQRE LSYGCVGVTWVNSG YPTNRLAFASFDE+++KN+LKN  P
KQQMTEEQREK LSYGCVGVTWVNSGPYPTNRLAFASFDENKY KNDLKNTSP

RSGETRAEFEGRVAKESFDEEKGFQRAREVASVMNRALENAHDESAYLDNLK
R  ETRAEFEGR+AK SFDE KGF+RAR+VASVMN+ ALENAHDE  Y+NLK
RPDETRAEFEGRI AKGSFDEGKGFKRARDVASVMNKALENAHDEGTYINNLK

KELANGNDALRNEDARSPFYSALRNTPSFKERNGGNHDPSRMKAVIYSKHFW
EL N NDAL ED+RS FYSALRNTPSFKER+GGN+DPS+MKAVIYSKHFW
TELTNNNDALLR EDSRSNFYSALRNTPSFKERDGGNYDPSKMKAVIYSKHFW

SGQDRSSSADKRKYGDPDAFRPAP GTGLVDMSRDRNIPRSPTSPGEGFVNF
SGQD +S+DKRKYGDP+AFRP    GTGLVDMS+DR+IPRSP  PGEG+VNF
SGQDQRGSSDKRKYGDPEAFRPDQGTGLVDMSKDRSIPRSPAKPGEGWVNF

DYGWFGAQTEADADKTVWTHGNHYHAPNGSLGAMHVYESKFRNWSEGYSD
DYGWFGAQTEADADKT WTHG +HYHAPN  LG MHV +ESKFR WS GY+D
DYGWFGAQTEADADKTTWTHGDHYHAPNSDLGPMHVHESKFRKSAGYAD

FDRGAYVITFIPKSWNTAPDKVKQGWP*     331 amino acids
FDRGAYVITFIPKSWNTAP KV+QGWP*
FDRGAYVITFIPKSWNTAPA KVEQGWP*    334 amino acids
```

EXAMPLE 5

Cloning of SC TGase Gene into an Expression Vector

The pCR2.1-SCTG plasmid was digested with Nhe I and Hind III and the DNA fragment containing the SC TGase gene was purified from the digest and subcloned into a pET-28a vector (Novagen). Positive clones with SC TGase gene insert, pET28-SCTG, were identified and sequenced.

Sequencing of pET28-SCTG reveals a DNA sequence, SEQ ID No. 11, genes encoding a recombinant 6×-His-TGase fusion protein from *Streptomyces cinnamoneus* ATCC 11874. The translated amino acid sequence, SEQ ID No. 12, encoding the recombinant 6×-His-TGase fusion protein of *Streptomyces cinnamoneus* ATCC 11874 (about 355 amino acids) is similar to the sequence of a transglutaminase from *Streptomyces cinnamoneus* CBS 683.68 (Duran et al., 1998). They differ, however, in that the recombinant TGase includes the extended 6×-His-tagged 23 amino acids in the N-terminus (MGSSHHHHHHSS-GLVPRGSHMAS-), which might help the recombinant SC TGase fusion protein to fold properly and to be active.

EXAMPLE 6

Over-Expression of Recombinant Transglutaminases

In order to purify recombinant SM TGase and SC TGase, pET28-SMTG and pET28-SCTG were used to transform *E. coli* strain BL21(DE3) cells (Novagen). Colonies with over-expression of N-terminus 6×His-tagged SM TGase fusion protein and N-terminus 6×His-tagged SC TGase fusion protein were screened. This was done by incubating each colony in about 1 ml LB medium with added Kanamycin (about 50 µg/ml), adding about 1 mM of IPTG to each culture at OD600 of about 0.8 to induce the expression of the fusion proteins, and continuing the incubation for about 2 hours at about 37° C. Clones with over-expression of recombinant transglutaminase SM TGase and SC TGase were confirmed by Coomassie Blue staining of SDS-PAGE gels. Induction of BL21(DE3)+pET28-SMTG *E. coli* cultures led to the over-expression of a recombinant 6×His-tagged SM TGase fusion protein and induction of BL21 (DE3)+pET28-SCTG *E. coli* cultures led to the over-expression of a recombinant 6×His-tagged SC TGase fusion protein, as judged by Coomassie Blue staining of SDS-PAGE gels. Cell fractionation experiments indicated that the over-expressed fusion proteins were expressed as inclusion bodies inside the host *E. Coli* cell, instead of soluble cytoplasmic or secreted proteins.

EXAMPLE 7

Purification of Recombinant Transglutaminases in Single Column Step

For large-scale expression of recombinant transglutaminases, such as SM TGase and SC TGase, an overnight culture (10 ml LB/Kanamycin) was grown at about 37° C. from a single colony of BL21(DE3)+pET28-SMTG or BL21 (DE3)+pET28-SCTG. The 10 ml saturated overnight culture was added to 250 ml LB/Kanamycin medium and incubated with shaking at 250 rpm at about 37° C. for 4 hours until OD600 absorbance value of the culture reached at about 0.8. IPTG (about 1 mM final concentration) was added to induce protein expression for 2 hours. After 2 hours, the induced cells were harvested by centrifugation at 5,000×g, and cell pellet was frozen at about –80° C. for about 1 hour.

The frozen cell pellet was resuspended and lysed in about 10 ml of nickel Ni+ binding buffer, containing about 6M guanidine titrated with hydrochloric acid (guanidine-HCl) to a pH of about 7.9, prepared in a solution containing about 20 mM of Tris buffer, about 5 mM imidazole, and about 0.5M sodium chloride (NaCl), in order to make all cellular and overexpressed proteins denatured and soluable, before being centrifuged at 12,000×g for 30 minutes to spin down unlysed cell debris. Meanwhile, a His-Bind Ni column (Novagen) was inserted into a Vaccum manifold (Big Basin) and pre-wetted with about 15 ml of binding buffer run through the column by applying a vacuum. After centrifugation, the supernatant was loaded into the pre-wetted His-Bind Ni+ column and a vacuum was applied to the column.

The loaded His-Bind Ni column was washed with 15 ml wash buffer containing about 6 M guanidine titrated with hydrochloric acid to a pH of about 7.9, prepared in a solution containing about 20 mM of Tris buffer, about 20 mM imidazole, and about 0.5M sodium chloride (NaCl). After washing, overexpressed recombinant fusion protein was eluted with 10 ml of elution buffer containing about 6 M guanidine titrated with hydrochloric acid to a pH of about 7.9 and prepared in a solution containing about 20 mM of Tris buffer, about 0.5M imidazole, and about 0.5M sodium chloride (NaCl), and collected in a 15 ml Falcon tube. DTT was added to the collected elution fraction to a final concentration of about 10 mM.

Because of the specificity of the Ni to the His×6 tag, the collected elution fraction contains about 99% of denatured 6×His-tagged fusion proteins. The denatured fusion proteins were renatured and/or refolded by adding to the collected elution fraction about 5 volumes of refolding buffer in a drop-wise manner (about 50 ml refolding buffer added to about 10 ml of collected elution fraction solution). The refolding buffer may include about 0.75 M of arginine, about 50 mM of Tris base titrated with hydrochloric acid (Tris-HCl) to a pH of about 8.0, about 50 mM of potassium chloride (KCl), and about 0.1 mM of a metal chelator, such as EDTA. The solution was stirred at 4° C. for 48 hours.

After refolding, the recombinant fusion proteins were dialyzed in about 2 liters of dialysis buffer at about 4° C. for about 24 hours in order to concentrate the purified recombinant protein for long-term storage in its inactive form., The dialysis buffer may include about 50 mM of Tris-HCl (at a pH of about 7.9), about 50 mM of KCl, about 0.1 mM of EDTA, and about 50% of glycerol. The dialyzed recombinant fusion protein sample was assayed for protein concentration using a protein assay kit (Bio-Rad). For example, a total of 5 mg of recombinant SM TGase fusion protein was obtained from the original 250 ml BL21(DE3)+pET28-SMTG $E. coli$ culture, and was stored at –20° C. In another experiment, about 3 mg of recombinant SC TGase fusion protein was obtained from the original 250 ml BL21 (DE3)+ pET28-SCTG $E. coli$ culture, and was stored at –20° C.

Figure 4:
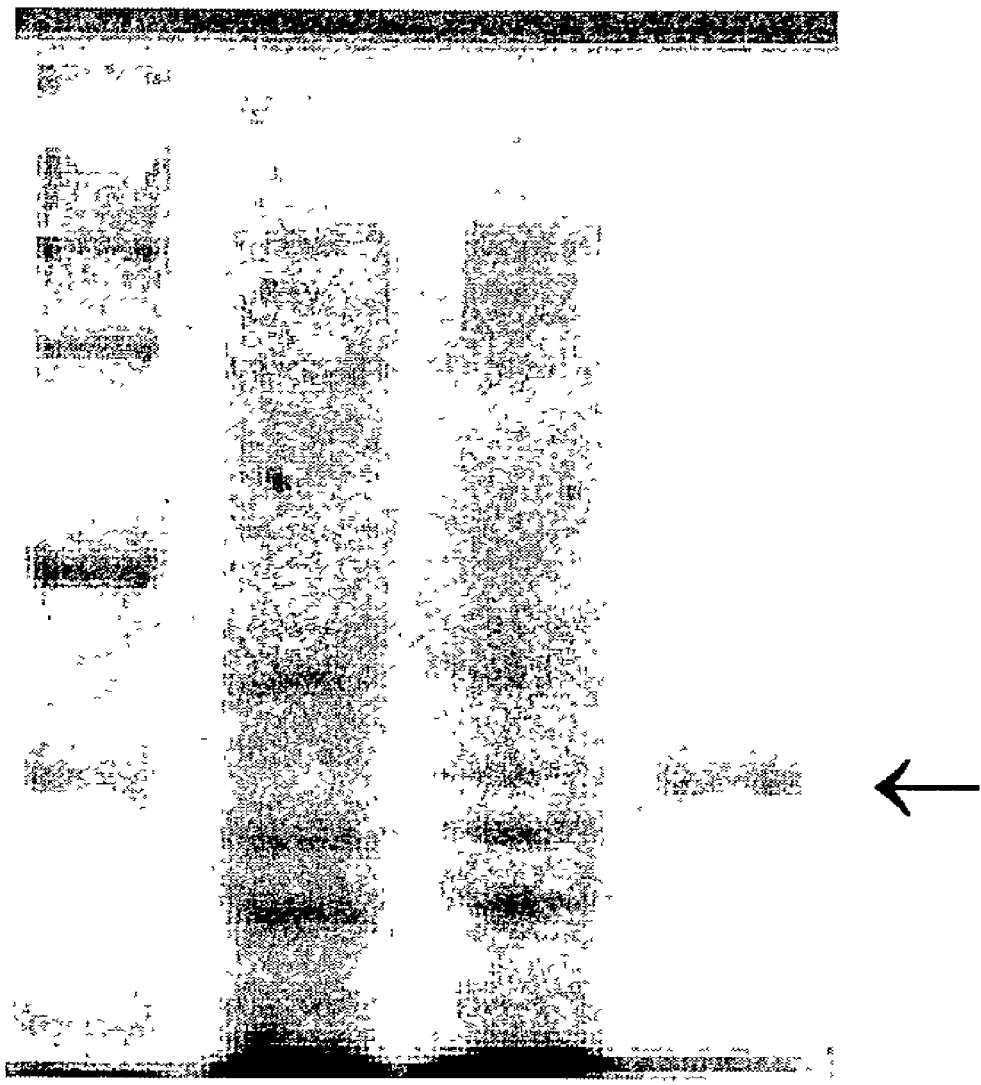
FIG. 4 is a polyacrylamide gel showing the results of purification of recombinant SM TGase fusion protein.

FIG. 4 demonstrated purification of the recombinant SM TGase fusion protein, showing the Coomassie Blue stained SDS-PAGE gel. Lane M of FIG. 4 is loaded with a mixture of molecular weight markers (from about 25 kDa to about 250 Kda). Lane 1 is loaded with cell lysate from BL21 (DE3)+pET28-SMTG $E. coli$ culture without IPTG induction. Lane 2 is loaded with cell lysate from BL21(DE3)+ pET28-SMTG $E. coli$ culture with about 1 mM of IPTG induction. Lane 3 is loaded with the purified 6×His-tagged SM TGase fusion protein after the single column purification through the His-Bind Ni+ column. The purified recombinant SM TGase fusion protein runs at an estimated molecular weight of about 37 kDa on the Coomassie Blue stained SDS-PAGE gel. The expression of recombinant SM TGase fusion protein was so tightly regulated that only after IPTG induction, the fusion protein was able to be expressed, as indicated by an arrow (present only in lane 2 and 3, but not in lane 1).

Over-expression and purification of the recombinant SC TGase fusion protein had also been confirmed by performing a Coomassie Blue stained SDS-PAGE gel. Cell lysate from BL21(DE3)+pET28-SCTG $E. coli$ culture without IPTG induction and cell lysate from BL21(DE3)+pET28-SCTG $E. coli$ culture with about 1 mM of IPTG induction were compared to show over-expression of the recombinant SC TGase fusion protein only when expression was induced. The purified 6×His-tagged SC TGase fusion protein after the single column purification through His-Bind Ni+ column migrated as a simple band to an estimated molecular weight of about 40 kDa on the Coomassie Blue stained SDS-PAGE gel.

EXAMPLE 8

Regeneration of Enzymatic Activity of the Purified Recombinant Transglutaminases Cross-linking reactions were set up to assay for cross-linking activity of the purified, inactive recombinant SM TGase fusion protein on a substrate, β-casein. The reactions were incubated at about 25° C. for 16 hours. In some cases, the reactions were incubated at about 37° C. for about 30 minutes or longer, such as about 1 hour or longer. Each reaction included about 0.005 unit of recombinant transglutaminase per 1 mg of β-casein substrate added to a cross-linking (CL) buffer. The CL buffer includes about 50 mM of Tris-HCl (at a pH of about 7.4), about 20% of glycerol, and various concentration of a reducing agent, DTT.

Figure 5:
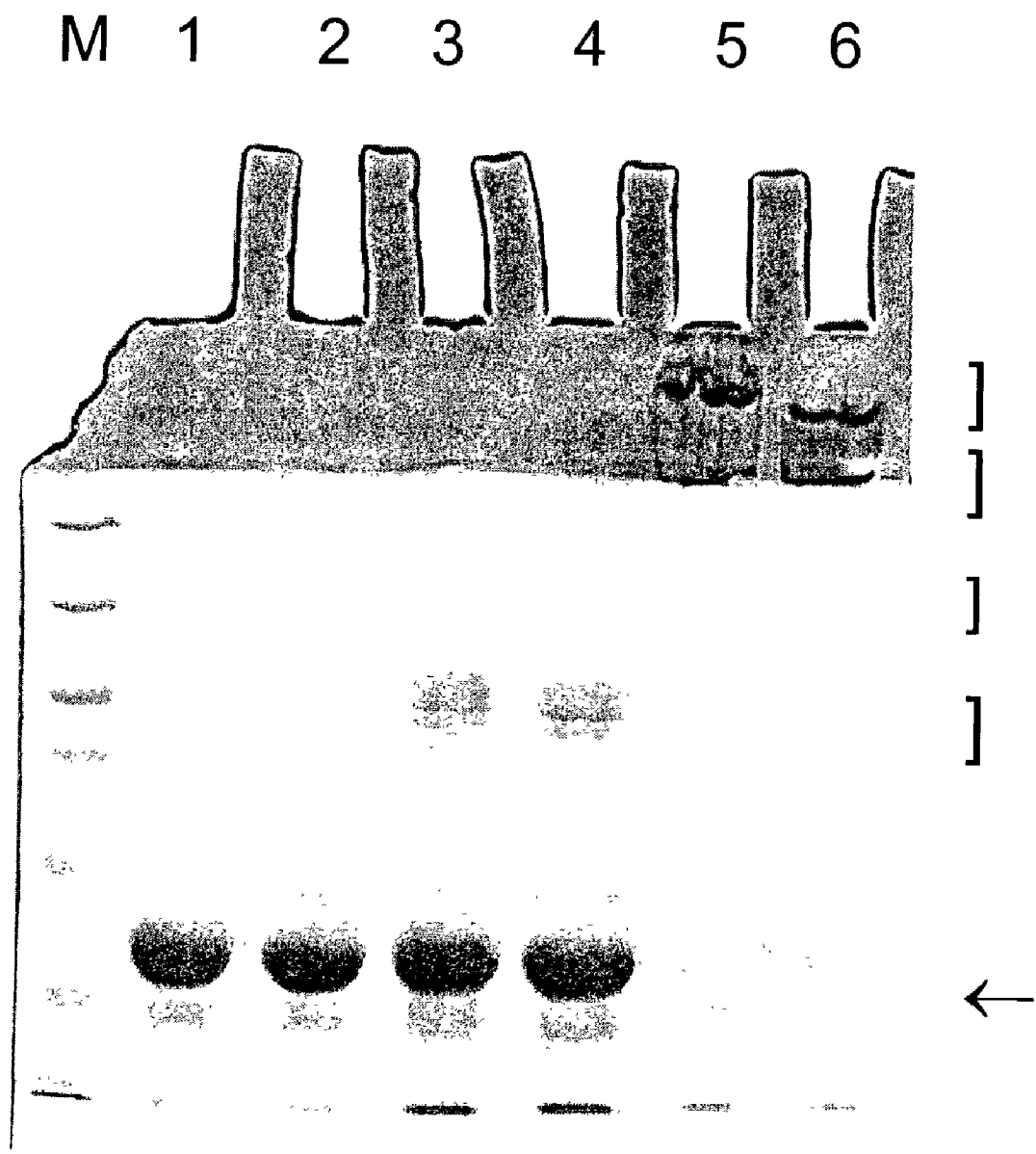
FIG. 5 is a polyacrylamide gel showing the results of regeneration of enzymatic activity of the purified recombinant SM TGase.

FIG. 5 demonstrates the results of exemplary cross-linking reactions using different reducing agent concentrations. Various reaction mixtures were loaded to a SDS-PAGE gel and stained with Coomassie Blue to visualize cross-linking of the β-casein substrate. In FIG. 5, lane M represents a mixture of molecular weight markers (from about 25 kDa to about 175 kDa). Lane 1 to lane 6 of FIG. 5 represent the cross-linking reaction mixtures in the presence of about 0 mM (lane 1 and 2), 2 mM (lane 3 and 4), or 10 mM (lane 5 and 6), of DTT.

As shown in FIG. 5, in the absence of DTT (lane 1 and 2), the recombinant SM TGase had no cross-linking activity on β-casein and β-casein runs as a monomer at an estimated molecular weight of 30 kDa. In the presence of CL buffer and about 2 mM of DTT (lane 3 and 4), the recombinant SM TGase was activated and β-casein run as a mixture of cross-linked polymer and monomer. In the presence of CL buffer and about 10 mM of DTT (lane 5 and 6), the recombinant SM TGase was very active and the catalytic cross-linking activity of SM TGase resulted in cross-linking of all detectable β-casein substrates in the reaction, as judged by the appearance of a high molecular weight polymer in the stacking gel and the dissapearance of the 30 kDa protein monomers.

In addition, the concentration of DTT in the CL buffer and activity of the recombinant SM TGase corresponded to a change of color of the reaction from clear to yellow. The results are shown in Table 3. The density of the yellow color was measured as absorbance value at $OD_{450}$. As shown in Table 3, there was an increase in $OD_{450}$ value for the reaction mixtures in the present of increased amount of DTT, which correlated to the enzymatic activity of the recombinant SM TGase fusion proteins as shown in FIG. 5.

TABLE 3

SM TGase activity correlates with change of solution color and reducing agent concentration.

| DTT concentration | 0 mM  | 2 mM  | 10 mM |
|-------------------|-------|-------|-------|
| OD 450            | 0.081 | 0.349 | 2.012 |

The effect of DTT and the change of solution color are unexpected features of the inactive/active transformation of the exemplary recombinant SM TGase and SC TGase fusion proteins, and have not been observed previously. The purified recombinant transglutaminases were assayed on a number of proteins including known substrates and non-substrates for native microbial transglutaminase.

EXAMPLE 9

Cross-linking Proteins by Purified Recombinant Transglutaminases

An assay was performed to test the cross-linking of β-casein, a known substrate of native transglutaminases, using the purified recombinant transglutaminase described here. β-casein is available from Sigma-Aldrich as a purified protein in its native form.

About 5 mg of β-casein (Sigma C-6905) was dissolved in phosphate-buffer-saline (PBS) to a concentration of about 10 mg/ml. The cross-linking reaction contained about 1 mg of the β-casein incubated with about 0.005 unit (about 5 µg, depending on the purification yield) of purified recombinant SM TGase fusion protein in a CL buffer containing about 50 mM of Tris-HCl (pH 7.4) and about 10 mM of DTT for about 16 hours at about 25° C. The experimental and control reactions were loaded on a SDS-PAGE gel and stained with Coomassie Blue after gel eletrophoresis.

The results indicated that when a control reaction containing only non-cross-linked (Non-CL) β-casein was loaded on a SDS-PAGE gel, the Non-CL β-casein migrated as a monomer. However, when the cross-linking reaction mixture was loaded, the cross-linked (CL) β-casein migrated as a smear on the SDS-PAGE gel indicating a mixture of high molecular weight polymers of different length. The control reaction containing only small amount of purified recombinant SM TGase without the β-casein substrate, was loaded on the SDS-PAGE gel, no protein band was observed. The enzyme used was approximately 5 µg of purified recombinant SM TGase per 1 mg of β-casein and is not visible by Coomassie Blue staining in the CL reaction mixture and SM TGase control reaction.

EXAMPLE 10

Cross-linking of Recombinant Protein Species by Purified Recombinant Transglutaminases Protein species that can serve as substrates of native transglutaminases but that were purified as recombinant proteins were also assayed to see if such purified recombinant protein species could be cross-linked by the purified recombinant transglutaminases. The purification and cross-linking of two examples of these transglutaminase substrates, recombinant serum albumin and recombinant cellulase, are described below.

Recombinant serum albumin was purified as secreted extracellular protein from yeast Pichia pastoris GS115 (His$^+$ Mut$^S$) (available from Invitrogen) containing an expression vector with a cloned serum albumin gene insert. Recombinant serum albumin was harvested from the medium through ammonia sulfate precipitation and centrifugated at a speed of about 10,000×g for about 10 minutes to pellet the expressed recombinant serum albumin protein. The purified protein pellet was resuspended in 6M guanidine-HCl (pH 7.9) and dialyzed in about 100 volumes of excess PBS solution without the addition of a reducing agent, DTT.

The dialyzed recombinant serum albumin protein was then concentrated by Aguacide (available from Calbiochem). The concentrated soluble fraction (supernatant) of recombinant serum albumin protein was assayed for protein concentration using a protein assay kit (available from Bio-Rad).

Cross-linking of recombinant serum albumin using purified recombinant SM TGase was performed and the cross-linking reaction mixture and control reactions were loaded on a SDS-PAGE gel. The cross-linking reaction mixture contained about 1 mg of recombinant serum albumin, incubated with about 0.005 Unit of purified recombinant SM TGase in the presence of the cross-linking buffer (about 50 mM of Tris-HCl, pH 7.4, and about 10 mM of DTT) at about 25° C. for about 16 hours.

First, the control reaction containing only the recombinant serum albumin migrated as a monomer after 12% SDS-PAGE gel electrophoresis and was not cross-linked (Non-CL) in the absence of SM TGase. However, the cross-linking reaction containing recombinant serum albumin revealed a mixture of very high molecular weight polymers of different length, which migrated as a smear in the stacking gel but not into the separating gel. Lane 3 contained a control reaction with about 5 ng of purified recombinant SMTGase in the reaction, not visible by Coomassie Blue staining.

EXAMPLE 11

Purification and Cross-linking of Recombinant Cellulase

A recombinant cellulase protein was cloned and overexpressed for analysis by cross-linking using the recombinant SM TGase fusion protein. A cellulase gene from Humicola grisea var. thermoides ATCC 16453 was cloned as a NheI-HindIII DNA fragment from genomic DNA of Humicola grisea var. thermoides ATCC 16453 using the PCR cloning procedure as described above. Two PCR primers were specifically designed for cloning of cellulase gene, SEQ ID No. 13 and SEQ ID No. 14. The cloned cellulase gene was then subcloned into pET28a (Novagen) expression vector for over-expression and purification of the recombinant cellulase protein from an E. coli host, BL21(DE3). Intracellular recombinant cellulase protein was purified through a His-Bind Ni$^+$ column (Novagen). The column was washed and the recombinant cellulase protein was eluted with a elution buffer containing about 0.5 M of imidazole and about 6M of guanidine-HCl (pH 7.9). The eluted protein was dialyzed in 100 volumes of excess PBS solution without the refolding agent DTT and then concentrated for storage at low temperature.

The results for the cross-linking of recombinant cellulase using the purified recombinant SM TGase were checked on an SDS-PAGE gel. The cross-linking reaction contained about 1 mg of recombinant cellulase, incubated with about 0.005 Unit of purified recombinant SM TGase in the presence of the CL buffer (about 50 mM of Tris-HCl, pH 7.4, and about 10 mM of DTT) at about 25° C. for various time periods. A control reaction having only the recombinant cellulase was not cross-linked (Non-CL) in the absence of SM TGase and migrated as a monomer after 12% SDS-PAGE gel electrophoresis. The recombinant cellulase was cross-linked into a mixture of very high molecular weight polymers of different length over time, which migrated as a smear into the stacking gel but not into the separating gel. Another control reaction with about 5 mg of purified recombinant SMTGase in the reaction showed no protein bands because the amount of recombinant SM TGase used in each reaction was not visible by Coomassie Blue staining.

EXAMPLE 12

Preparations of Non-substrate Protein Species to be Cross-linked by Purified Recombinant Transglutaminases Protein species that typically cannot serve as substrates for native transglutaminases were reacted with the purified recombinant transglutaminase fusion proteins. Native microbial transglutaminase can cross-link only a small number of substrate protein species. Human transglutaminase Factor XIII has an even narrower substrate spectrum. For the most part, it has been shown that bovine serum albumin (BSA), histone protein, glucose oxidase, ovalbumin, and myelin basic protein (MBP) are all poor substrates for native transglutaminase.

It has been theorized that most proteins, polypeptides, and peptides are poor substrates for transglutaminase due to a limited number of glutamine and lysine residues in these molecules. In addition, even for molecules that do contain glutamine and lysine, steric hindrance due to folding into three-dimensional structures may result in no cross-linking activity.

When the purified recombinant transglutaminase fusion proteins were used initially to cross-link non-substrate proteins, such as bovine serum albumin (BSA), histone protein, glucose oxidase, ovalbumin, and myelin basic protein (MBP) (all available from Sigma), there was no cross-linking even in the presence of a large amount of the purified recombinant transglutaminase fusion proteins in the activation solution. For example, even in the presence of 10 mM DTT in the CL buffer, there was no cross-linking of the non-substrate native proteins. However, it was found through experimetation that modification of the proteins and/or specific preparation of the proteins to be used in the cross-linking reaction resulted in the cross-linking of a broad range of protein species by the purified recombinant transglutaminases.

About 10 mg of each of BSA, histone protein, glucose oxidase, and ovalbumin, were denatured in 10 ml of about 6M of guanidine-HCl (pH 7.9). After denaturation, each protein sample was dialyzed in 2 liters of PBS solution without the reducing agent, DTT, at about 4° C. for about 24 hours. It is thought that the denatured proteins are partially refolded after dialysis without the addition of the reducing agent.

After dialysis, the samples were centrigued at 10,000 xg for about 10 minutes and minor precipitation was discarded. The soluble supernatant sample was assayed for protein concentration using a protein assay kit (Bio-Rad) and diluted in PBS solution to about 5 mg/ml. If the sample concentration was less than about 2 mg/ml, the sample was concentrated through Aquacide (Calbiochem) in dialysis bags to a concentration of at least about 2 mg/ml.

EXAMPLE 13

Cross-linking of Modified Non-substrate Protein Species by Purified Recombinant Transglutaminases The denatured and partially refolded protein species, such as bovine serum albumin (BSA), histone, glucose oxidase, and ovalbumin, as well as the native protein species of bovine serum albumin (BSA), histone, glucose oxidase, and ovalbumin were cross-linked in the CL buffer containing about 50 mM of Tris-HCl (pH 7.4) and about 10 mM of DTT in the presence of about 0.05 unit of purified recombinant SM TGase per 1 mg of modified proteins at about 25° C. for about 16 hours. The resulting reactions were applied to 12% SDS-PAGE and stained with Coomassie Blue after gel electrophoresis. In each experiment cross-linking reactions for both native protein and modified protein were prepared.

The results from SDS-PAGE showed that only the reactions containing the modified protein species of BSA, histine H3 protein, glucose oxidase, and ovalbumin were cross-linked by the purified recombinant SM TGase. The cross-linked products of these modified proteins migrated as a smear in the stacking gel, indicating the production of a mixture of high molecular weight cross-linked polymers by recombinant transglutaminases. Control reactions having only native proteins or modified proteins without added purified recombinant SM TGase were also checked on SDS-PAGE. The non-cross-linked proteins migrated as a monomer. Note that the SM TGase used was about 10 fold higher in amount (about 50 µg) and can be stained by Coomassie Blue. The results from the cross-linked modified non-substrate protein species suggested that modified protein samples (through denaturation and dialysis) are cross-linked to a far greater extent than the native protein samples. Note that complete and partial cross-linking was both observed for native histine H3 protein under the condition tested.

EXAMPLE 14

Cross-linking of Two or More Protein Species by Purified Recombinant Transglutaminases The purified recombinant transglutaminases were used to cross-link a mixture of proteins/polypeptides. For example, cross-linking of a mixture of β-casein and glucose oxidase by purified recombinant SM TGase was performed, using about 0.005 unit of SM TGase per 1 mg of combined β-casein and glucose oxidase, and was checked on SDS-PAGE. As another example, cross-linking of cellulase and serum albumin by purified recombinant SM TGase was also performed, using about 0.005 unit of SM TGase per 1 mg of combined cellulase and serum albumin. In both experiments, the cross-linking reactions migrated as a smear present in the stacking gel indicating cross-linking of both protein species into a mixture of high molecular weight cross-linked polymers by recombinant transglutaminases. Control reactions without added purified recombinant SM TGase confirmed the migration of the non-cross-linked proteins to their respective monomer positions. Control reactions with only the purified recombinant SM TGase resulted in no protein band because the amount of purified SM TGase used cannot be stained by Coomassie Blue. In each experiment, both protein species can be cross-linked by the purified recombinant SM TGase, as indicated by the disappearance of the two monomer bands.

EXAMPLE 15

Cross-linking of Naturally-occurring Peptides by Purified Recombinant Transglutaminases The purified recombinant transglutaminases described herein were used to cross-link short chains of naturally-occurring or synthetic peptides that have internal glutamine and lysine residues (not on the N-terminus or C-Terminus). One example is the naturally-occurring β-amyloid peptide (1–42) which plays an important role during the pathogenesis of Alzheimer's disease.

Figure 6:
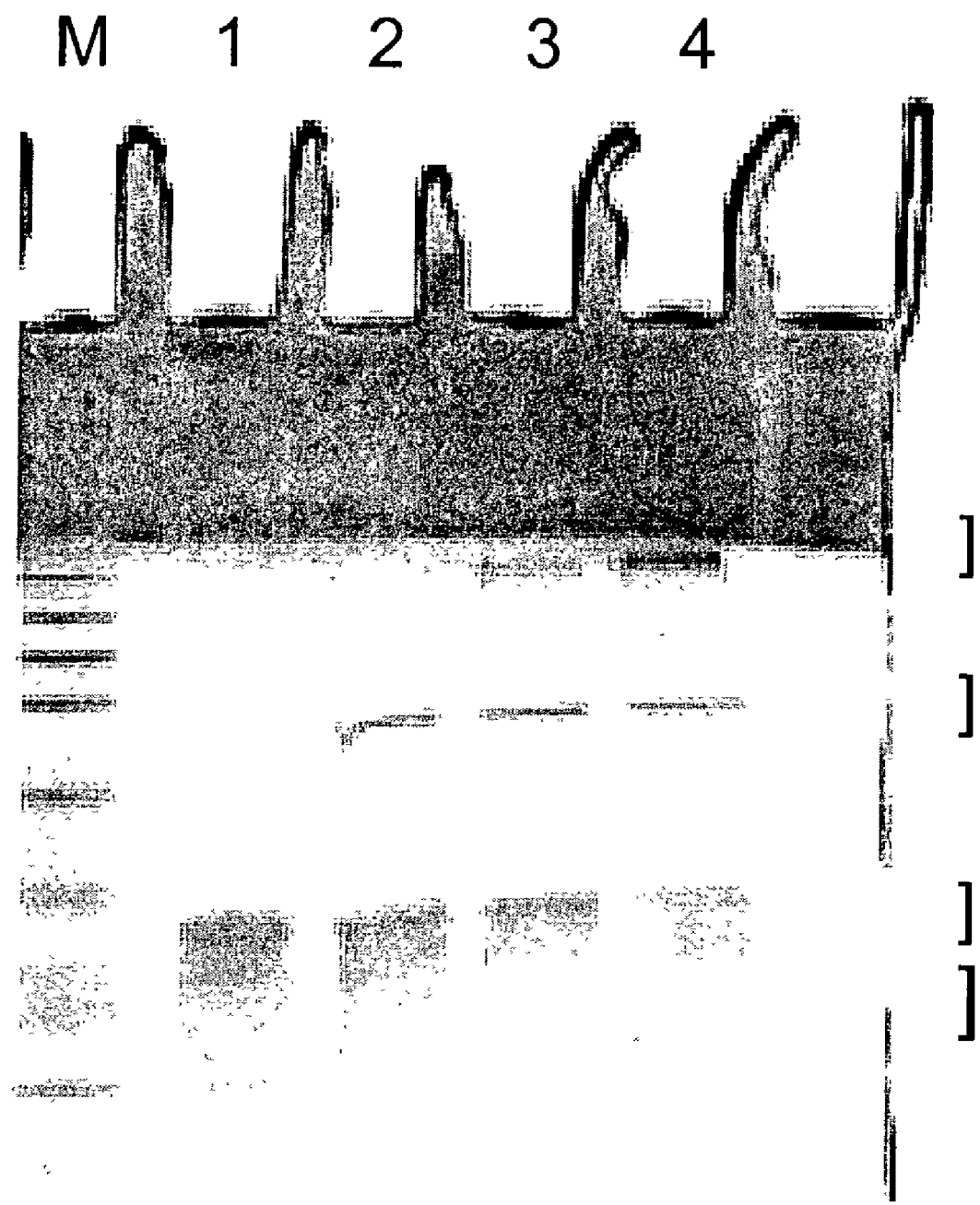
FIG. 6 is a polyacrylamide gel showing the results of cross-linking of β-amyloid peptide by purified recombinant TGase fusion protein.

FIG. 6 illustrates cross-linking of β-amyloid peptide (1–42, SEQ ID NO. 15, DAEFRHDSGTEVHHQKLVF-FAEDVGSNKGAIIGLMVGGVVIA 42 amino acid) by purified recombinant transglutaminases, using about 0.05 unit (about 50 μg) of purified recombinant SM TGase per 1 mg of β-amyloid peptide. The β-amyloid (1–42) peptide (purchased from American Peptide Company (Sunnyvale, Calif.) includes 1 glutamine (Gln, Q) residue and 2 lysine (Lys, K) residues that can be reacted with transglutaminase.

In FIG. 6, lanes 2–4 contained the cross-linking reactions incubated for about 1 hour, 2 hours and 3 hours, respectively. The β-amyloid (1-42) peptide can be cross-linked by the recombinant transglutaminase as shown as a smear of a mixture of cross-linked peptides on the top of the separating gel and the disappearance of the peptide bands at the bottom of the SDS-PAGE. Lane 1 of FIG. 6 contained the control reaction (β-amyloid peptide only) without added purified recombinant SM TGase, showing the migration of the non-cross-linked peptides at the bottom of the SDS-PAGE.

EXAMPLE 16

Cross-linking of Synthetic Peptides by Purified Recombinant Transglutaminases

The purified recombinant transglutaminases were also used to cross-link short chain synthetic peptides that have glutamine and lysine residues on the N-terminus or C-terminus. Clearly, if there are no glutamine and/or lysine residues in the amino acid sequence of the proteins, polypeptides, and peptides to be cross-linked by transglutaminase, the proteins, polypeptides, and peptides can be modified to include glutamine and/or lysine residues on the N-terminus or C-terminus.

For example, cross-linking activity of the purified recombinant transglutaminase was assayed on a peptide, BSA5. The peptide sequence of BSA5 (SEQ ID No.16, KKKC-CTESLVNRRPCFSQQQ, 20 amino acids) was designed and synthesized from ResGen (Invitrogen) to include with 3 extra lysine residues on the amino (N) terminus and 3 extra glutamine residues on the carboxyl (C) terminus. The peptide sequence of BSA5 also includes an amino acid sequence of about 14 amino acids (residue number 4 to 17 in BSA5 peptide), according to the sequence of BSA protein from *Bos taurus* and corresponding to part of C-terminal conserved portion of bovine serum albumin (BSA) protein family.

BSA5 peptide was synthesized and stored in PBS solution to be cross-linked with SM TGase. The cross-linking reaction was set up using about 0.05 unit (about 50 μg) of SM TGase per 1 mg of BSA5 peptide in CL buffer at about 25° C. for about 16 hours.

Figure 7:
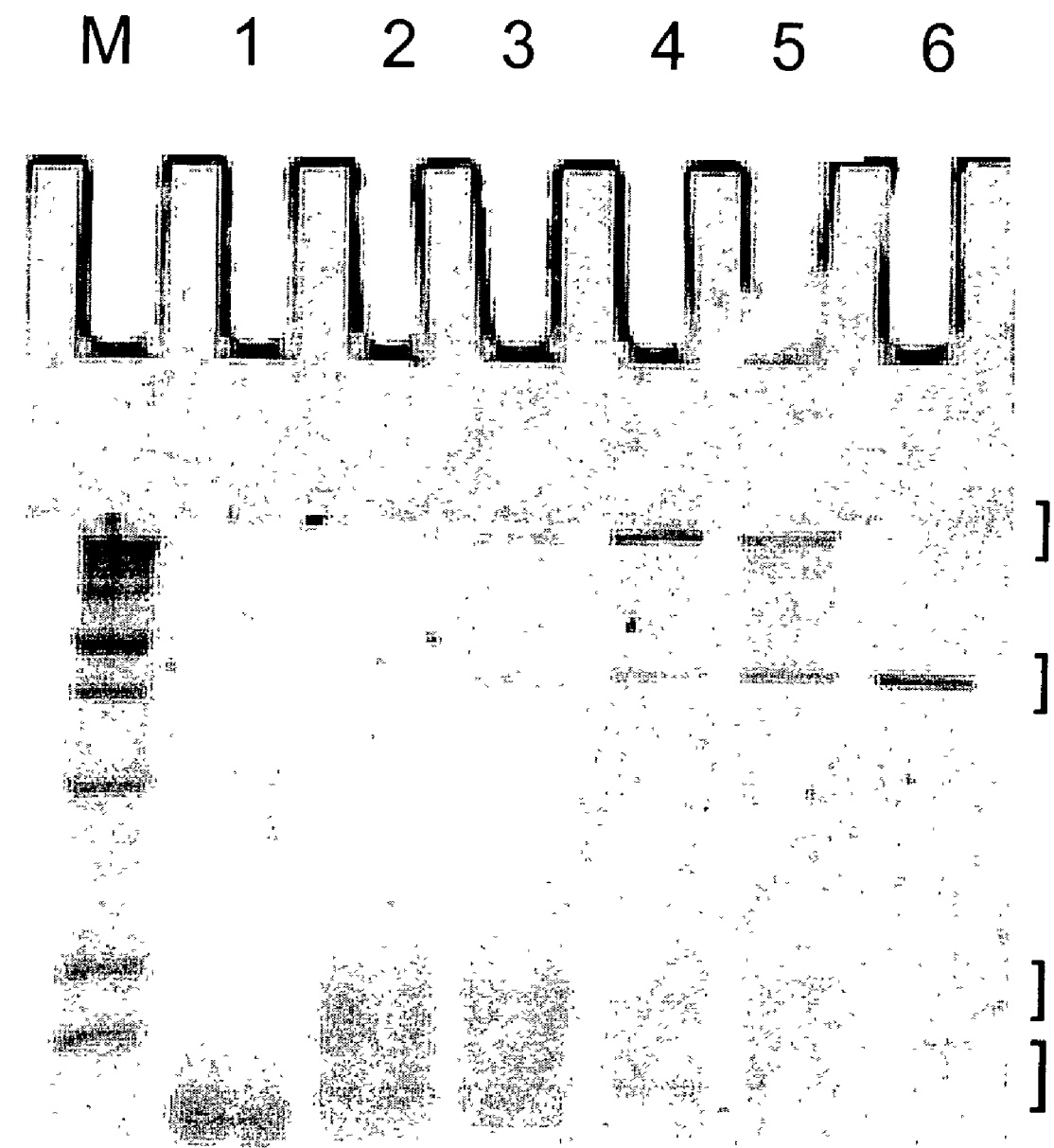
FIG. 7 is a polyacrylamide gel showing the results of cross-linking of BSA5 peptide by purified recombinant TGase fusion protein.

FIG. 7 is a Coomassie Blue stained SDS-PAGE gel and illustrates cross-linking of BSA5 peptide by purified recombinant transglutaminase fusion protein. Lane 1 contained non-cross-linked BSA 5 peptide monomer. Lanes 2–5 contained the cross-linking reaction in the presence of increased amount of recombinant SM TGase corresponding to an increase in cross-linked (CL) BSA5 peptide, which run as a large molecular weight polymer on the top of the separating gel. Lane 6 contained only purified recombinant SM TGase (about 50 ng) as a control.

The results of the cross-linking experiments described above suggest that the purified recombinant transglutaminases exhibit high enzymatic activity on a variety of substrates, modified non-substrates, and mixtures of two or more substrates, including proteins, polypeptides, peptides, to generate different lengths of cross-linked homo-polymers and even hetero-polymers. The method of cross-linking using transglutaminases and the cross linked products provide a powerful tool to be used in many applications, including but not limited to, vaccine development and immunotherapy.

EXAMPLE 17

Immunization with Cross-linked Products

Cross-linked products such as those examples described above were used as antigens to induce a high level of antibody production in mouse, as compared to the lower level of antibody production in response to the use of non-cross-linked monomer antigens. For the experiments described below, about 100 μg of non-cross-linked proteins, polypeptides, and peptides, and cross-linked products were diluted in about 0.5 ml PBS solution for use in immunizing a mouse (Southwest mouse, 8–12 weeks old). In addition, about 0.8 mg of aluminum hydroxide was used as adjuvant.

For example, four mice were immunized with about 100 μg of β-casein and four mice were immunized with about 100 μg of cross-linked β-casein. The mice were immunized at day 1 and day 21, and serum was collected at day 28 from each mouse. Collected sera were titered by enzyme-linked immunosorbent assay (ELISA) using the following procedure. An ELISA plate was coated with 1 μg/100 μl/well of β-casein (Non-CL) in PBS solution at about 4° C. for about 16 hours. After coating, the plate was washed three times with 200 μl/well of wash buffer containing 1×PBS plus 0.05% Tween 20. After washing, the plate was blocked in blocking buffer containing 1% bovine serum albumin (BSA) in wash buffer at room temperature for 1 hour. The plate was washed three times with wash buffer of about 200 μl/well. Sera collected from day 28 immunized mice were serially diluted half from 1:100 to 1:409600 in blocking buffer. Series of diluted sera were loaded onto the ELISA plate at about 100 μl/well in duplicate wells and incubated at room temperature for about 1 hour. The plate was washed three times with wash buffer of about 200 μl/well. Peroxidase conjugated anti-mouse secondary antibody was diluted in blocking buffer (1:2500) and loaded onto the ELISA plate at 100 μl/well and incubated at room temperature for about 1 hour. The plate was washed three times with wash buffer and then developed using about 100 μl/well of peroxidase substrate The plate was incubated at room temperature for 30 minutes, and the color developed was stopped with about 4N of hydrogen sulfate ($H_2SO_4$).

The color-developed ELISA plate was pictured and measured in ELISA reader at 450 nm absorbance The duplicated value was averaged and the results were plotted into FIGS. 8–11 and discussed below (anti-sera collected from four mice of the same immunogen injection were averaged and standard deviation for each set of experiment was shown).

EXAMPLE 18

Immunization Using Cross-linked Products of Native Proteins as Antigens

ELISA results for the anti-sera obtained from mice immunized with cross-linked and non-cross-linked native β-casein protein were obtained. The results suggest that cross-linked native proteins can be used to induce antibody production and the anti-sera obtained from the cross-linked β-casein react or bind much stronger to β-casein than the anti-sera obtained from the non-cross-linked β-casein. The resulting $OD_{450}$ value from the ELISA assay is shown in Table 4 and is about 10:1 or more for cross-linked versus non-cross-linked. More importantly, the titer of the anti-sera of the cross-linked β-casein is much higher than that of the non-cross-linked β-casein. Significantly, the titer of the anti-sera is calculated to be increased to about 128 fold or more (cross-linked versus non-cross-linked).

EXAMPLE 19

Immunization Using Cross-linked Products of Recombinant Proteins as Antigens Cross-linked recombinant proteins, such as cross-linked recombinant serum albumin and cross-linked recombinant cellulase were also used as antigens to immunize mice. ELISA results for the anti-sera obtained from mice immunized with the cross-linked and non-cross-linked recombinant serum albumin were obtained. The results suggest that the anti-sera obtained from the cross-linked recombinant serum albumin will react or bind much stronger to recombinant serum albumin than the anti-sera obtained from the non-cross-linked recombinant serum albumin. The resulting $OD_{450}$ value is shown in Table 5 and is about 10:1 or more for cross-linked versus non-cross-linked recombinant serum albumin. Significantly, the titer of the anti-sera is calculated to be increased to about 64 fold or more (cross-linked versus non-cross-linked).

TABLE 4

450 nm absorbance values for various anti-sera from mice immunized with cross-linked and non-cross-linked native β-casein protein as assayed on ELISA plate coated with β-casein

| Mice | 1:100 | 1:200 | 1:400 | 1:800 | 1:1600 | 1:3200 | 1:6400 | 1:12800 | 1:25600 | 1:51200 | 1:102400 | Blank |
|---|---|---|---|---|---|---|---|---|---|---|---|---|
| Non-CL 1 | 0.954 | 0.558 | 0.332 | 0.223 | 0.184 | 0.165 | 0.087 | 0.082 | 0.082 | 0.084 | 0.084 | 0.082 |
| Non-CL 2 | 1.121 | .0673 | .0371 | 0.245 | 0.163 | 0.161 | 0.086 | 0.083 | 0.084 | 0.082 | 0.079 | 0.081 |
| Non-CL 3 | 0.894 | 0.509 | .0315 | 0.194 | 0.142 | 0.150 | 0.087 | 0.081 | 0.081 | 0.078 | 0.084 | 0.079 |
| Non-CL 4 | 0.781 | .0432 | 0.239 | 0.159 | 0.144 | 0.134 | 0.079 | 0.081 | 0.078 | 0.079 | 0.080 | 0.080 |
| CL-1 | 2.153 | 2.122 | 2.111 | 2.101 | 1.900 | 1.623 | 1.237 | 0.795 | 0.432 | 0.226 | 0.158 | 0.081 |
| CL-2 | 2.159 | 2.115 | 2.034 | 1.970 | 1.744 | 1.430 | 0.939 | 0.484 | 0.237 | 0.169 | 0.113 | 0.080 |
| CL-3 | 2.098 | 2.123 | 2.020 | 1.926 | 1.755 | 1.427 | 0.996 | 0.537 | 0.300 | 0.181 | 0.122 | 0.083 |
| CL-4 | 2.093 | 2.088 | 1.996 | 1.867 | 1.625 | 1.225 | 0.805 | 0.420 | 0.232 | 0.145 | 0.114 | 0.082 |

TABLE 5

450 nm absorbance values for various anti-sera from mice immunized with cross-linked and non-cross-linked recombinant serum albumin as assayed on ELISA plate coated with cellulase

| Mice | 1:100 | 1:200 | 1:400 | 1:800 | 1:1600 | 1:3200 | 1:6400 | 1:12800 | 1:25600 | 1:51200 | 1:102400 | Blank |
|---|---|---|---|---|---|---|---|---|---|---|---|---|
| Non-CL 1 | 0.881 | 0.562 | 0.310 | 0.224 | 0.168 | 0.141 | 0.084 | 0.081 | 0.080 | 0.084 | 0.087 | 0.088 |
| Non-CL 2 | 0.768 | 0.443 | 0.301 | 0.178 | 0.137 | 0.121 | 0.091 | 0.071 | 0.084 | 0.079 | 0.083 | 0.089 |
| Non-CL 3 | 0.824 | 0.512 | 0.298 | 0.201 | 0.132 | 0.125 | 0.082 | 0.078 | 0.088 | 0.075 | 0.085 | 0.079 |
| Non-CL 4 | 0.781 | 0.412 | 0.224 | 0.154 | 0.124 | 0.118 | 0.082 | 0.077 | 0.086 | 0.073 | 0.084 | 0.078 |
| CL-1 | 2.110 | 2.079 | 2.043 | 1.935 | 1.698 | 1.425 | 0.889 | 0.516 | 0.310 | 0.173 | 0.118 | 0.081 |
| CL-2 | 2.088 | 2.071 | 2.014 | 1.923 | 1.703 | 1.415 | 0.902 | 0.479 | 0.274 | 0.149 | 0.105 | 0.085 |
| CL-3 | 2.015 | 2.011 | 1.985 | 1.779 | 1.535 | 1.247 | 0.769 | 0.385 | 0.2210 | 0.122 | 0.092 | 0.082 |
| CL-4 | 2.210 | 2.105 | 2.036 | 1.956 | 1.702 | 1.433 | 0.921 | 0.526 | 0.342 | 0.182 | 0.121 | 0.077 |

ELISA results for the anti-sera obtained from mice immunized with the cross-linked and non-cross-linked recombinant cellulase were also obtained. The results suggest that the anti-sera obtained from the cross-linked recombinant cellulase will react or bind much stronger to recombinant serum cellulase the anti-sera obtained from the non-cross-linked recombinant cellulose. The resulting $OD_{450}$ value is shown in Table 6 and is about 8:1 or more for cross-linked versus non-cross-linked recombinant cellulose. Significantly, the titer of the anti-sera is calculated to be increased to about 20 fold or more (cross-linked versus non-cross-linked).

EXAMPLE 21

Immunization Using Cross-linked Products of Protein Mixtures as Antigens

Cross-linked protein mixtures, such as cross-linking products of a mixture of two or more proteins, were also used as antigens to immunize mice. ELISA results for the anti-sera

TABLE 6

450 nm absorbance values for various anti-sera from mice immunized with cross-linked and non-cross-linked recombinant cellulase as assayed on ELISA plate coated with cellulase

| Mice | Serum dilution | | | | | | | | | | | |
|---|---|---|---|---|---|---|---|---|---|---|---|---|
| | 1:100 | 1:200 | 1:400 | 1:800 | 1:1600 | 1:3200 | 1:6400 | 1:12800 | 1:25600 | 1:51200 | 1:102400 | Blank |
| Non-CL 1 | 0.621 | 0.302 | 0.146 | 0.112 | 0.089 | 0.082 | 0.085 | 0.076 | 0.086 | 0.075 | 0.087 | 0.078 |
| Non-CL 2 | 0.714 | 0.401 | 0.211 | 0.162 | 0.138 | 0.129 | 0.085 | 0.071 | 0.084 | 0.080 | 0.076 | 0.081 |
| Non-CL 3 | 0.771 | 0.432 | 0.253 | 0.172 | 0.141 | 0.123 | 0.078 | 0.085 | 0.084 | 0.079 | 0.072 | 0.074 |
| Non-CL 4 | 0.811 | 0.481 | 0.289 | 0.201 | 0.151 | 0.141 | 0.096 | 0.084 | 0.076 | 0.081 | 0.077 | 0.084 |
| CL-1 | 1.975 | 1.742 | 1.593 | 1.324 | 1.015 | 0.784 | 0.301 | 0.256 | 0.166 | 0.094 | 0.082 | 0.081 |
| CL-2 | 2.012 | 1.824 | 1.496 | 1.215 | 0.964 | 0.622 | 0.288 | 0.179 | 0.095 | 0.081 | 0.079 | 0.082 |
| CL-3 | 1.894 | 1.642 | 1.356 | 1.112 | 0.812 | 0.405 | 0.197 | 0.102 | 0.084 | 0.078 | 0.075 | 0.077 |
| CL-4 | 1.912 | 1.688 | 1.412 | 1.135 | 0.902 | 0.521 | 0.259 | 0.148 | 0.089 | 0.083 | 0.081 | 0.085 |

EXAMPLE 20

Immunization Using Cross-linked Products of Modified Non-substrate Proteins as Antigens Cross-linked modified non-substrate proteins, such as cross-linked glucose oxidase, were also used as antigens to immunize mice. ELISA results for the anti-sera obtained from mice immunized with modified non-substrate proteins antigens, the cross-linked and non-cross-linked glucose oxidase, were obtained. The results suggest that the anti-sera obtained from the cross-linked glucose oxidase will react or bind much stronger to glucose oxidase than the anti-sera obtained from the non-cross-linked glucose oxidase ($OD_{450}$ value was about 12:1 or more for cross-linked versus non-cross-linked as shown in Table 7). Significantly, the titer of the anti-sera is calculated to be increased to about 64 fold or more (cross-linked versus non-cross-linked).

obtained from mice immunized using cross-linked and non-cross-linked protein mixtures as antigens were obtained. For example, anti-sera against cross-linked products of protein mixture containing β-casein and glucose oxidase (about 200 µg of total protein) were obtained. The anti-sera obtained were assayed on ELISA plate coated with either β-casein or glucose oxidase and the results were plotted. The anti-sera obtained from the cross-linked mixtures reacted or bound much more strongly to β-casein than the anti-sera obtained from the non-cross-linked mixtures. The resulting $OD_{450}$ value is about 10:1 or more for cross-linked versus non-cross-linked as shown in Table 8. Significantly, the titer of the anti-sera is calculated to be increased to about 64 fold or more (cross-linked versus non-cross-linked).

TABLE 7

450 nm absorbance values for various anti-sera from mice immunized with cross-linked and non-cross-linked modified glucose oxidase as assayed on ELISA plate coated with glucose oxidase

| Mice | Serum dilution | | | | | | | | | | | |
|---|---|---|---|---|---|---|---|---|---|---|---|---|
| | 1:100 | 1:200 | 1:400 | 1:800 | 1:1600 | 1:3200 | 1:6400 | 1:12800 | 1:25600 | 1:51200 | 1:102400 | Blank |
| Non-CL 1 | 0.785 | 0.421 | 0.241 | 0.162 | 0.141 | 0.091 | 0.087 | 0.088 | 0.091 | 0.079 | 0.081 | 0.081 |
| Non-CL 2 | 0.912 | 0.524 | 0.321 | 0.242 | 0.153 | 0.137 | 0.086 | 0.091 | 0.087 | 0.082 | 0.086 | 0.079 |
| Non-CL 3 | 0.776 | 0.425 | 0.223 | 0.161 | 0.145 | 0.125 | 0.088 | 0.081 | 0.078 | 0.089 | 0.079 | 0.082 |
| Non-CL 4 | 0.889 | 0.511 | 0.302 | 0.224 | 0.149 | 0.132 | 0.092 | 0.086 | 0.085 | 0.082 | 0.087 | 0.085 |
| CL-1 | 2.252 | 2.241 | 2.125 | 2.013 | 1.921 | 1.598 | 1.241 | 0.779 | 0.354 | 0.21 | 0.145 | 0.086 |
| CL-2 | 2.158 | 2.115 | 2.052 | 2.021 | 1.812 | 1.457 | 1.121 | 0.697 | 0.325 | 0.195 | 0.143 | 0.078 |
| CL-3 | 2.198 | 2.101 | 1.986 | 1.821 | 1.752 | 1.321 | 0.987 | 0.596 | 0.258 | 0.168 | 0.119 | 0.087 |
| CL-4 | 2.168 | 2.116 | 2.032 | 1.925 | 1.798 | 1.465 | 1.028 | 0.621 | 0.305 | 0.175 | 0.126 | 0.085 |

TABLE 8

450 nm absorbance values for various anti-sera from mice immunized
with cross-linked and non-cross-linked β-casein and glucose oxidase mixtures as
assayed on ELISA plate coated with β-casein

| Mice | Serum dilution | | | | | | | | | | | |
|---|---|---|---|---|---|---|---|---|---|---|---|---|
| | 1:100 | 1:200 | 1:400 | 1:800 | 1:1600 | 1:3200 | 1:6400 | 1:12800 | 1:25600 | 1:51200 | 1:102400 | Blank |
| Non-CL 1 | 1.015 | 0.621 | 0.321 | 0.232 | 0.159 | 0.138 | 0.078 | 0.082 | 0.085 | 0.075 | 0.084 | 0.086 |
| Non-CL 2 | 1.211 | 0.691 | 0.381 | 0.263 | 0.192 | 0.175 | 0.095 | 0.086 | 0.081 | 0.086 | 0.080 | 0.084 |
| Non-CL 3 | 0.846 | 0.472 | 0.281 | 0.192 | 0.126 | 0.088 | 0.075 | 0.084 | 0.083 | 0.078 | 0.081 | 0.075 |
| Non-CL 4 | 0.951 | 0.569 | 0.302 | 0.211 | 0.165 | 0.121 | 0.082 | 0.088 | 0.084 | 0.078 | 0.077 | 0.084 |
| CL-1 | 2.088 | 2.021 | 1.892 | 1.745 | 1.378 | 1.026 | 0.785 | 0.511 | 0.281 | 0.124 | 0.095 | 0.078 |
| CL-2 | 2.114 | 2.031 | 2.002 | 1.865 | 1.724 | 1.428 | 0.921 | 0.668 | 0.341 | 0.176 | 0.118 | 0.080 |
| CL-3 | 2.121 | 2.113 | 2.067 | 1.987 | 1.801 | 1.521 | 1.047 | 0.761 | 0.403 | 0.217 | 0.170 | 0.081 |
| CL-4 | 2.085 | 2.005 | 1.881 | 1.798 | 1.354 | 1.102 | 0.742 | 0.477 | 0.259 | 0.106 | 0.087 | 0.089 |

Advantageously, in another ELISA experiment, the same anti-sera also react to glucose oxidate. The resulting $OD_{450}$ value is about 8:1 or more for cross-linked versus non-cross-linked as shown in Table 9 and the titer of the anti-sera is thus calculated to be increased to about 32 fold or more for the cross-linked mixtures versus non-cross linked mixtures.

TABLE 9

450 nm absorbance values for various anti-sera from mice immunized
with cross-linked and non-cross-linked β-casein and glucose oxidase mixtures as
assayed on ELISA plate coated with glucose oxidase

| Mice | Serum dilution | | | | | | | | | | | |
|---|---|---|---|---|---|---|---|---|---|---|---|---|
| | 1:100 | 1:200 | 1:400 | 1:800 | 1:1600 | 1:3200 | 1:6400 | 1:12800 | 1:25600 | 1:51200 | 1:102400 | Blank |
| Non-CL 1 | 0.672 | 0.325 | 0.221 | 0.143 | 0.125 | 0.085 | 0.084 | 0.083 | 0.078 | 0.077 | 0.074 | 0.082 |
| Non-CL 2 | 0.841 | 0.441 | 0.277 | 0.171 | 0.136 | 0.091 | 0.087 | 0.076 | 0.088 | 0.084 | 0.072 | 0.079 |
| Non-CL 3 | 0.669 | 0.345 | 0.237 | 0.142 | 0.129 | 0.089 | 0.085 | 0.081 | 0.073 | 0.082 | 0.083 | 0.077 |
| Non-CL 4 | 0.691 | 0.367 | 0.242 | 0.151 | 0.130 | 0.084 | 0.075 | 0.082 | 0.081 | 0.085 | 0.078 | 0.083 |
| CL-1 | 2.015 | 1.997 | 1.826 | 1.546 | 1.136 | 0.788 | 0.421 | 0.258 | 0.132 | 0.089 | 0.085 | 0.075 |
| CL-2 | 1.985 | 1.846 | 1.528 | 1.102 | 0.779 | 0.441 | 0.236 | 0.168 | 0.091 | 0.079 | 0.082 | 0.083 |
| CL-3 | 2.221 | 2.106 | 1.895 | 1.742 | 1.358 | 1.108 | 0.756 | 0.448 | 0.216 | 0.181 | 0.095 | 0.085 |
| CL-4 | 1.962 | 1.823 | 1.486 | 1.089 | 0.748 | 0.389 | 0.221 | 0.129 | 0.085 | 0.082 | 0.078 | 0.073 |

Figure 8:
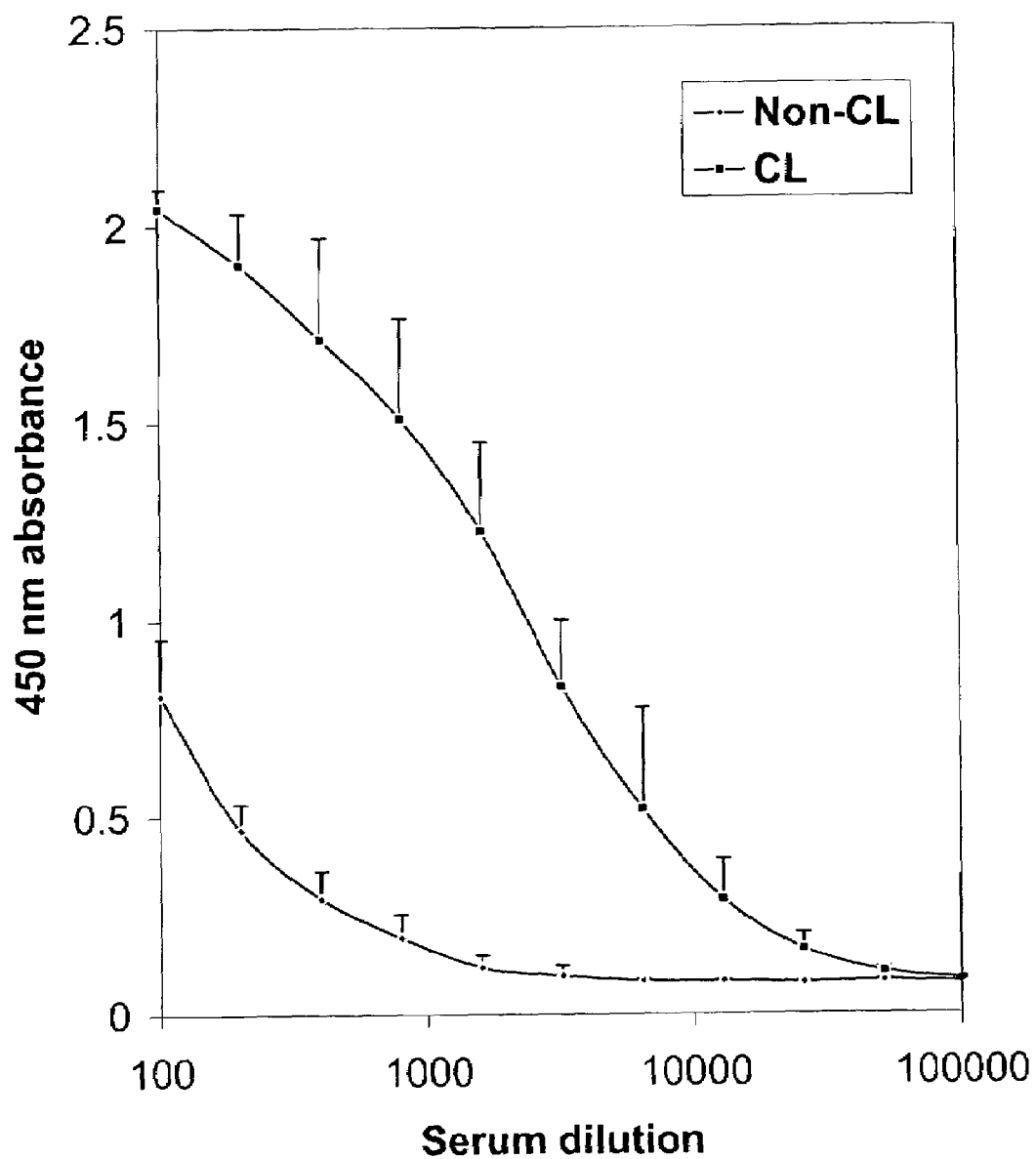
FIG. 8 is a graph of the ELISA results for anti-sera obtained from using cross-linked products of a protein mixture of serum albumin and cellulase as antigens and assayed against serum albumin.
Figure 9:
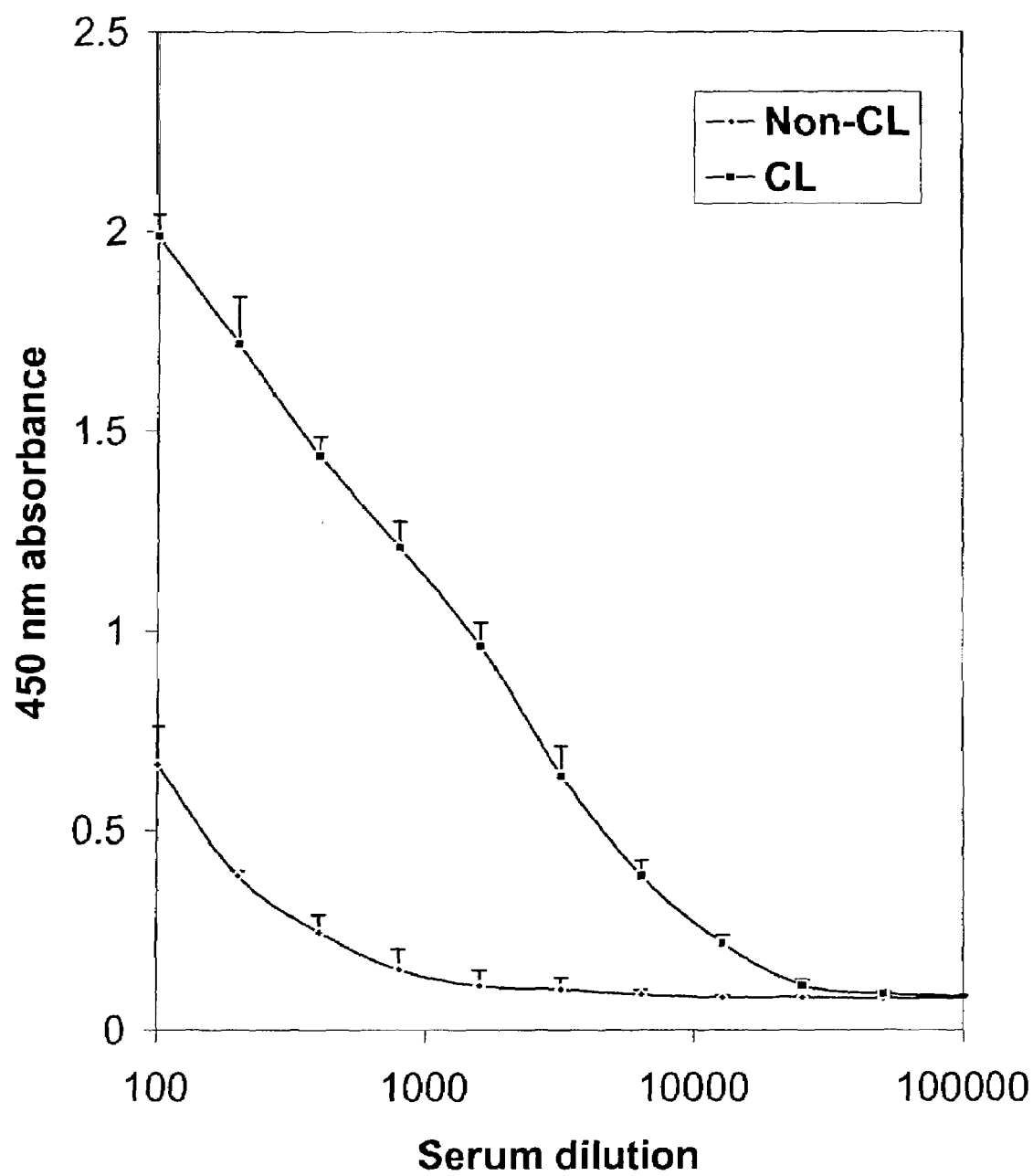
FIG. 9 is a graph of the ELISA results for anti-sera obtained from using cross-linked products of a protein mixture of serum albumin and cellulase as antigens and assayed against cellulase.

FIGS. 8 and 9 showed the ELISA results of cross-linked products of protein mixtures containing serum albumin and cellulase (about 200 μg of total protein). The anti-sera obtained were assayed on ELISA plate coated with either serum albumin or cellulase and the results were plotted in FIGS. 8 and 9, respectively. In FIG. 8, the anti-sera obtained from the cross-linked mixtures reacted or bound much more strongly to serum albumin than the anti-sera obtained from the non-cross-linked mixtures. The resulting $OD_{450}$ value was about 7:1 or more for cross-linked protein mixture versus non-cross-linked protein mixture. Significantly, the titer of the anti-sera is calculated to be increased to about 32 fold or more (cross-linked versus non-cross-linked). Advantageously, in FIG. 9, the same anti-sera also react to cellulose. The resulting $OD_{450}$ value is about 8:1 or more for cross-linked versus non-cross-linked and the titer of the anti-sera is calculated to be increased to about 32 fold or more for the cross-linked mixtures versus non-cross-linked mixtures.

EXAMPLE 22

Immunization Using Cross-linked Products of Peptides as Antigens

Figure 10:
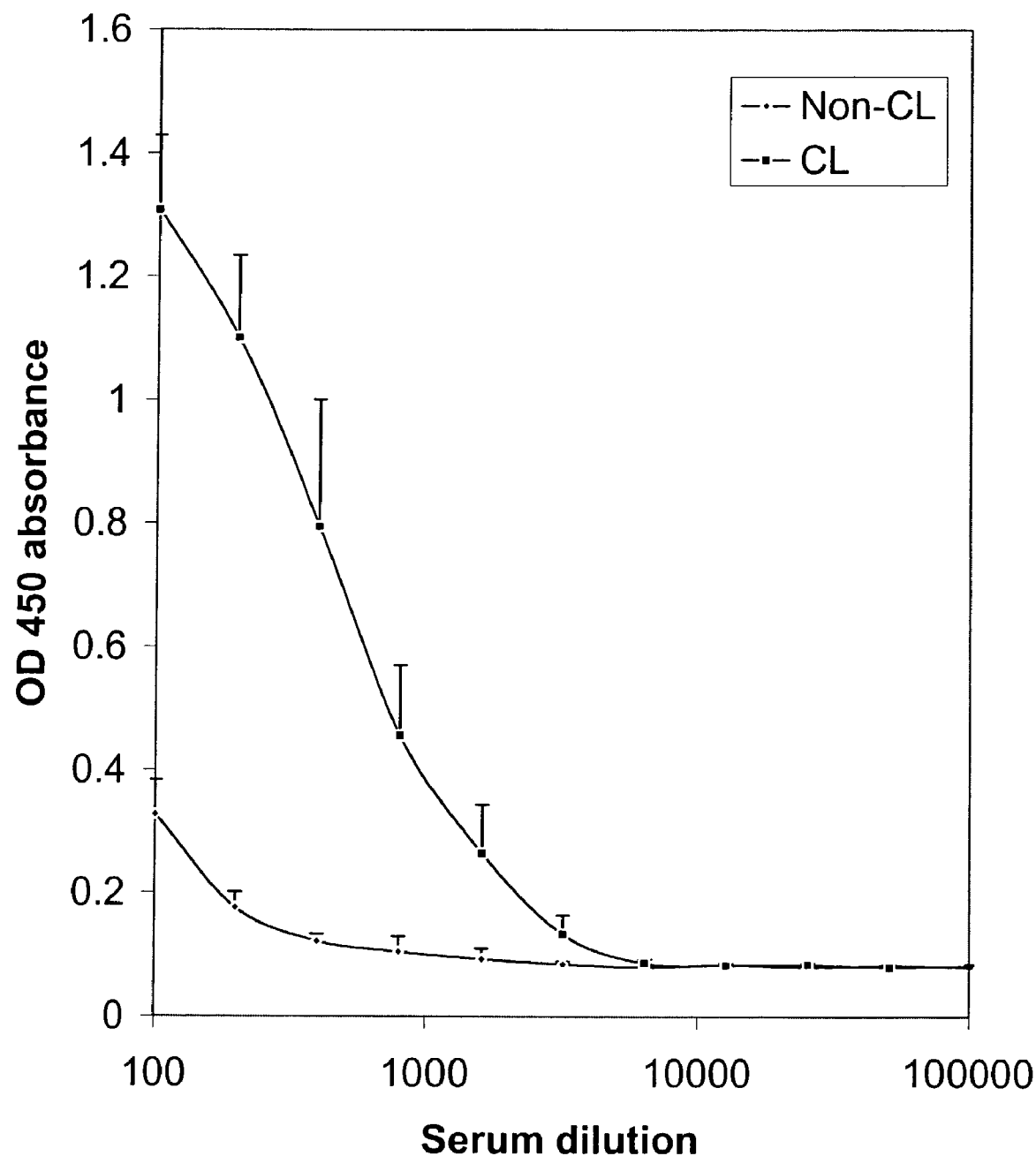
FIG. 10 is a graph of the ELISA results for anti-sera obtained from using cross-linked products of β-amyloid peptide as antigens.
Figure 11:
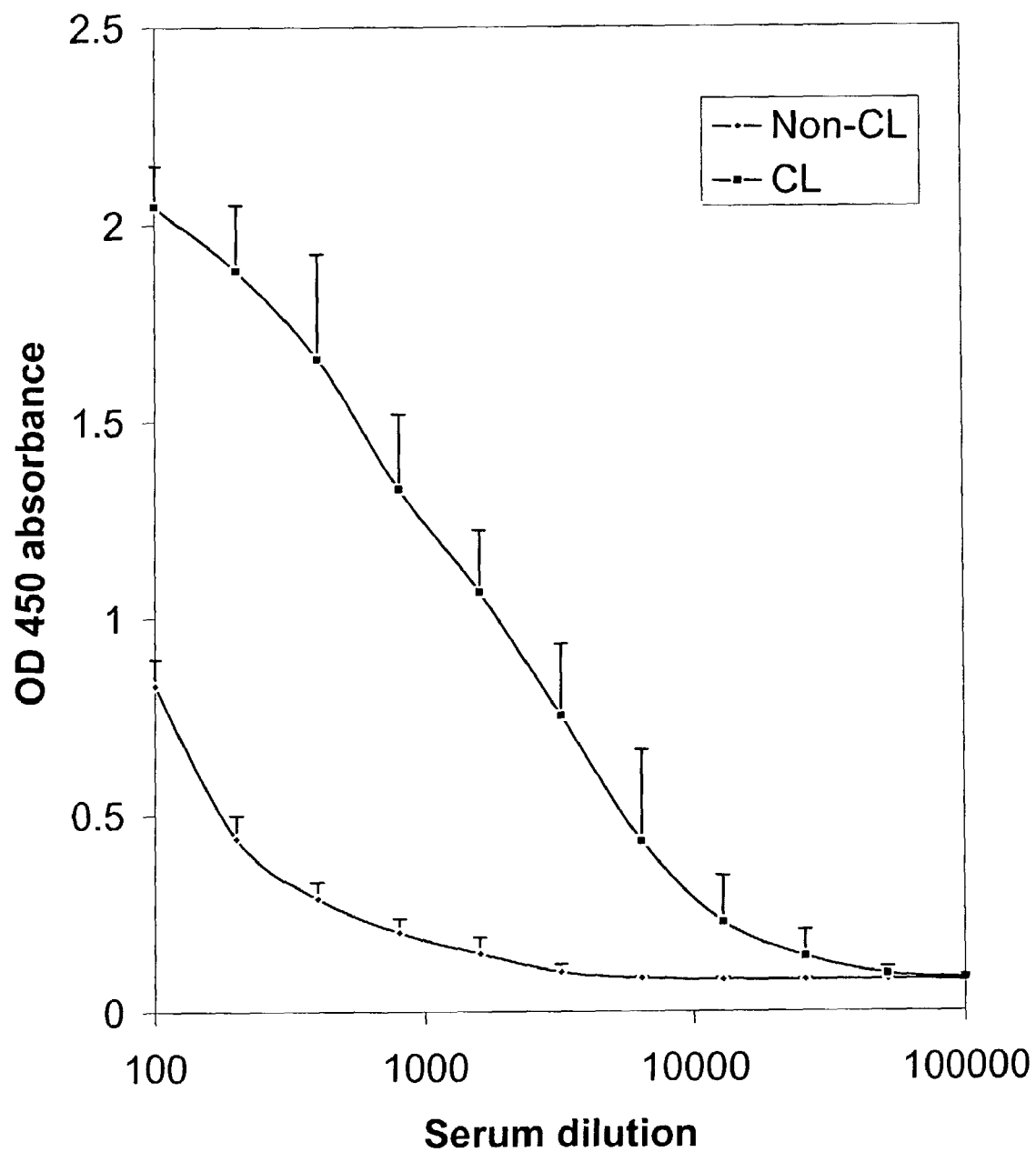
FIG. 11 is a graph of the ELISA results for anti-sera obtained from using cross-linked products of BSA5 peptide as antigens.

Cross-linked peptides, such as cross-linked β-amyloid peptide and cross-linked BSA5 peptide, were also used as antigens to immunize mice and the results are shown in FIGS. 10–11.

FIG. 10 illustrates the ELISA results for the anti-sera obtained from mice immunized with peptide antigens, the cross-linked and non-cross-linked β-amyloid peptide. The results suggest that the anti-sera obtained from the cross-linked β-amyloid peptide reacted or bound much more strongly to β-amyloid peptide than the anti-sera obtained from the non-cross-linked β-amyloid peptide ($OD_{450}$ value was about 6:1 or more for cross-linked versus non-cross-linked). Significantly, the titer of the anti-sera is calculated to be increased to about 10 fold or more (cross-linked versus non-cross-linked).

FIG. 11 illustrates the ELISA results for the anti-sera obtained from mice immunized with peptide antigens, the cross-linked and non-cross-linked BSA5 peptide. The results suggest that the anti-sera obtained from the cross-linked BSA5 peptide reacted or boud much more strongly to BSA5 peptide than the anti-sera obtained from the non-cross-linked BSA5 peptide ($OD_{450}$ value is about 7:1 or more for cross-linked versus non-cross-linked). Significantly, the titer of the anti-sera is calculated to be increased to about 32 fold or more (cross-linked versus non-cross-linked).

While the foregoing is directed to embodiments of the invention, other and further embodiments of the invention may be devised without departing from the basic scope thereof, and the scope thereof is determined by the claims that follow.

What is claimed is:

1. A method of producing a recombinant transglutaminase, comprising:
overexpressing the recombinant transglutaminase in a host cell containing a transglutaminase gene cloned from an organism comprising *Streptomyces* spp. comprising a sequence selected from the group consisting of SEQ ID NO: 6, SEQ ID NO: 8, SEQ ID NO: 10, SEQ ID NO: 12 into an expression vector;
purifying the recombinant transglutaminase;
storing the recombinant transglutaminase in an inactive form under a condition in the absence of dithiothreitol (DTT); and
reactivating the inactive form of the recombinant transglutaminase into an active form by adding DTT.

2. The method of claim 1, wherein the DTT comprises about 0.5 M of dithiothreitol (DTT).

3. The method of claim 2, wherein the DTT comprises from 2 mM to 10 mM of DTT.

4. The method of claim 1, wherein the organism is selected from the group consisting of *Streptomyces mobaraensis*, *Streptomyces cinnamoneus*, and isolates thereof.

5. The method of claim 1, further comprising a color change when the recombinant transglutaminase reactivates from the inactive form into the active form.

6. The method of claim 5, wherein the solution of the active form of the recombinant transglutaminase comprises an absorbance value (OD value) of 0.1 or more at a wavelength from 400 nm to 500 nm.

7. The method of claim 5, wherein the solution of the active form of the recombinant transglutaminase has an absorbance value of 0.2 or more at OD 450 nm.

8. A method of producing a recombinant transglutaminase, comprising:
expressing the recombinant transglutaminase in a host cell from an expression vector having a transglutaminase gene cloned from an organism comprising *Streptomyces* spp. comprising a sequence selected from the group consisting of SEQ ID NO: 6, SEQ ID NO: 8, SEQ ID NO: 10, SEQ ID NO: 12;
purifying the recombinant transglutaminase under denaturing conditions using a denaturant;
refolding the recombinant transglutaminase into a folded structure using a refolding solution;
storing the recombinant transglutaminase in an inactive form under a condition in the absence of dithiothreitol (DTT); and
reactivating the inactive form of the recombinant transglutaminase into an active form by adding DTT.

9. The method of claim 8, further comprising concentrating the purified recombinant transglutaminase.

10. The method of claim 9, wherein concentrating the purified recombinant transglutaminase is carried out by dialyzing the purified recombinant transglutaminase in a storage buffer.

11. The method of claim 10, wherein the storage buffer comprises about 200 mM of a salt, about 5 mM of a metal chelator, about 70% glycerol, and about 200 mM of a pH buffering agent titrated to a pH of 5 to 11.

12. The method of claim 11, wherein the storage buffer is 50 mM of potassium chloride, 0.1 mM EDTA, 50% glycerol, and 50 mM of Tris base titrated with hydrochloric acid to a pH of 5 to 11.

13. The method of claim 8, wherein the DTT comprises about 0.5 M DTT.

14. The method of claim 13, wherein the DTT comprises from 2 mM to 10 mM of DTT.

15. The method of claim 8, further comprising reacting the recombinant transglutaminase with a compound selected from the group consisting of polypeptides, naturally occurring proteins, polyamino acids, cell-membrane-associated proteins, tumor-associated antigens, cytokines, cytokine receptors, bacterial toxins, whole bacterial cells, viral coat proteins, whole viruses, viral glycoproteins, cell wall-derived coat proteins, peptides, synthetic peptides, and modifications and derivatives of the aforementioned compounds, in an activation solution to activate the recombinant transglutaminase.

16. The method of claim 15, wherein the activation solution comprises a reducing agent, deionized water, a pH buffering agent for adjusting the pH of the activation solution.

17. The method of claim 16, wherein the reducing agent comprises about 0.5 M of DTT.

18. The method of claim 17, wherein the reducing agent is from 2 mM to 10 mM of DTT.

19. The method of claim 8, wherein the organism is selected from the group consisting of *Streptomyces mobaraensis*, *Streptomyces cinnamoneus*, and isolates thereof.

20. The method of claim 8, wherein the purifying step is carried out by a technique selected from the group consisting of ligand affinity chromatography, antibody affinity chromatography, ion-exchange chromatography, hydrophobic interaction chromatography, ultrafiltration, automated peptide synthesis, and combinations thereof.

21. The method of claim 8, wherein the denaturant is selected from the group consisting of guanidine, urea, and combinations thereof.

22. The method of claim 21, wherein the denaturant is 6M of guanidine titrated with hydrochloric acid to a pH of 7 to 9.

23. The method of claim 8, wherein refolding the recombinant transglutaminase comprises renaturing the compound through a technique selected from the group consisting of dilution, dialysis, gel filtration, and combinations thereof.

24. The method of claim 8, wherein the refolding solution comprises about 200 mM of a salt, about 5 mM of a metal chelator, and about 200 mM of a pH buffering agent titrated to a pH of 5 to 11.

25. The method of claim 8, wherein the refolding solution comprises 50 mM of potassium chloride, 0.1 mM of EDTA, 750 mM of arginine, and 50 mM of Tris base titrated to a pH of 5 to 11.

26. The method of claim 8, further comprising a color change when the recombinant transglutaminase reactivates from the inactive form into the active form.

27. The method of claim 26, wherein the solution of the active recombinant transglutaminase comprises an absorbance value (OD value) of 0.1 or more at a wavelength from 400 nm to 500 nm.

28. The method of claim 27, wherein the solution of the active recombinant transglutaminase has an absorbance value of about 0.2 or more at OD 450 nm.

29. A method of producing a recombinant transglutaminase, comprising:
preparing a DNA construct having a transglutaminase gene cloned from an organism comprising *Streptomyces* spp. comprising a sequence selected from the group consisting of SEQ ID NO: 6, SEQ ID NO: 8, SEQ ID NO: 10, SEQ ID NO: 12;
subcloning the DNA construct having the cloned transglutaminase gene into an expression vector;
transforming a host cell and culturing the host cell comprising the expression vector having the subcloned transglutaminase gene;
expressing the recombinant transglutaminase into insoluble inclusion bodies;
disrupting the host cell using a denaturant;
purifying the recombinant transglutaminase;
refolding the recombinant transglutaminase into folded structure using a refolding solution;
storing the recombinant transglutaminase in an inactive form under a condition in the absence of dithiothreitol (DTT); and
reactivating the inactive form of the recombinant transglutaminase into an active form by adding DTT.

30. The method of claim 29, further comprising concentrating the purified recombinant transglutaminase.

31. The method of claim 30, wherein concentrating the purified recombinant transglutaminase is carried out by dialyzing the purified recombinant transglutaminase in a storage buffer.

32. The method of claim 31, wherein the storage buffer comprises about 200 mM of a salt, about 5 mM of a metal chelator, about 70% glycerol, and about 200 mM of a pH buffering agent titrated to a pH of 5 to 11.

33. The method of claim 32, wherein the storage buffer is 50 mM of potassium chloride, 0.1 mM EDTA, 50% glycerol, and 50 mM of Tris base titrated to a pH of 5 to 11.

34. The method of claim 29, wherein the DTT comprises about 0.5 M of DTT.

35. The method of claim 34, wherein the DTT comprises from 2 mM to 10 mM of DTT.

36. The method of claim 29, further comprising reacting the recombinant transglutaminase with a compound selected from the group consisting of polypeptides, naturally occurring proteins, polyamino acids, cell-membrane-associated proteins, tumor-associated antigens, cytokines, cytokine receptors, bacterial toxins, whole bacterial cells, viral coat proteins, whole viruses, viral glycoproteins, cell wall-derived coat proteins, peptides, synthetic peptides, and modifications and derivatives of the aforementioned compounds, in an activating solution to activate the recombinant transglutaminase.

37. The method of claim 36, wherein the activating solution comprises a reducing agent, deionized water, a pH-buffering agent for adjusting the pH of the activation solution.

38. The method of claim 37, wherein the reducing agent comprises about 0.5 M of DTT.

39. The method of claim 38, wherein the reducing agent comprises from 2 mM to 10 mM of DTT.

40. The method of claim 29, wherein the organism is selected from the group consisting of *Streptomyces mobaraensis*, *Streptomyces cinnamoneus*, and isolates thereof.

41. The method of claim 29, wherein the purifying step is carried out by a technique selected from the group consisting of ligand affinity chromatography, antibody affinity chromatography, ion-exchange chromatography, hydrophobic interaction chromatography, ultrafiltration, automated peptide synthesis, and combinations thereof.

42. The method of claim 29, wherein the denaturant is selected from the group consisting of guanidine, urea, and combinations thereof.

43. The method of claim 42, wherein the denaturant is 6M of guanidine titrated with hydrochloric acid to a pH of 6 to 9.

44. The method of claim 29, wherein refolding the recombinant transglutaminase comprises renaturing the recombinant transglutaminase through a technique selected from the group consisting of dilution, dialysis, gel filtration, and combinations thereof.

45. The method of claim 29, wherein the refolding solution comprises about 200 mM of a salt, about 5 mM of a metal chelator, and about 200 mM of a pH buffering agent titrated to a pH of 5 to 11.

46. The method of claim 29, wherein the refolding solution comprises 50 mM of potassium chloride, 0.1 mM of EDTA, and 750 mM of arginine, 50 mM of Tris titrated to pH of 5 to 11.

47. The method of claim 29, further comprising a color change when the recombinant transglutaminase reactivates from the inactive form into the active form.

48. The method of claim 47, wherein the solution of the active recombinant transglutaminase comprises an absorbance value (OD value) of 0.1 or more at a wavelength from 400 nm to 500 nm.

49. The method of claim 47, wherein the solution of the active recombinant transglutaminase has an absorbance value of 0.2 or more at OD 450 nm.

50. The method of claim 29, further comprising catalyzing an acyl transfer of the γ-carboxyamide group of a glutamine residue in a compound selected from the group consisting of polypeptides, naturally occurring proteins, polyamino acids, cell-membrane-associated proteins, tumor-associated antigens, cytokines, cytokine receptors, bacterial toxins, whole bacterial cells, viral coat proteins, whole viruses, viral glycoproteins, cell wall-derived coat proteins, peptides, synthetic peptides, and modifications and derivatives of the aforementioned compounds, by the active form of recombinant transglutaminase.

51. The method of claim 50, wherein the catalyzing step is carried out in the presence of a reducing agent.

* * * * *